(12) United States Patent
Ding et al.

(10) Patent No.: US 7,211,576 B2
(45) Date of Patent: May 1, 2007

(54) DIAMINOTHIAZOLES

(75) Inventors: Qingjie Ding, Bridgewater, NJ (US);
Nan Jiang, Fairfield, NJ (US);
Kyungjin Kim, Livingston, NJ (US);
Allen John Lovey, North Caldwell, NJ (US); Warren William McComas, Denville, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 199 days.

(21) Appl. No.: 11/098,563

(22) Filed: Apr. 4, 2005

(65) Prior Publication Data

US 2005/0239843 A1  Oct. 27, 2005

Related U.S. Application Data

(60) Provisional application No. 60/563,712, filed on Apr. 20, 2004.

(51) Int. Cl.
*A61K 31/5355* (2006.01)
*A61K 31/4468* (2006.01)
*A61K 31/427* (2006.01)
*C07D 413/14* (2006.01)
*C07D 277/40* (2006.01)
*C07D 417/02* (2006.01)

(52) U.S. Cl. .................. 514/231.5; 514/326; 514/370; 544/129; 546/209; 548/190

(58) Field of Classification Search ............ 514/326, 514/370, 231.5; 544/129; 546/209; 548/190
See application file for complete search history.

(56) References Cited

U.S. PATENT DOCUMENTS

| 6,569,878 B1 | 5/2003 | Chong et al. |
| 6,818,663 B2 | 11/2004 | Chu et al. |
| 2002/0151554 A1 | 10/2002 | Chen et al. |
| 2004/0006058 A1 | 1/2004 | Chu et al. |
| 2004/0082595 A1 | 4/2004 | Ding et al. |
| 2004/0087594 A1 | 5/2004 | Ding et al. |
| 2004/0162303 A1 | 8/2004 | Bartkovitz et al. |

FOREIGN PATENT DOCUMENTS

| WO | WO 97/16447 | 5/1997 |
| WO | WO 98/33798 | 8/1998 |
| WO | WO 99/09030 | 2/1999 |
| WO | WO 99/21845 | 5/1999 |
| WO | WO 99/24416 | 5/1999 |
| WO | WO 99/43675 | 9/1999 |
| WO | WO 99/43676 | 9/1999 |
| WO | WO 00/12485 | 3/2000 |
| WO | WO 00/26202 | 5/2000 |
| WO | WO 00/39101 | 7/2000 |
| WO | WO 00/75120 | 12/2000 |
| WO | WO 01/056567 | 8/2001 |
| WO | WO 01/60816 | 8/2001 |
| WO | WO 01/79198 | 10/2001 |
| WO | WO 02/12250 A2 | 2/2002 |
| WO | WO 04/014904 | 2/2004 |

OTHER PUBLICATIONS

Rosania, G. R. et al., Exp. Opin. Ther. Patents 2000, vol. 10, pp. 215-230.
Senderowicz, A. M. et al., J. Natl. Cancer Inst. 2000, vol. 92, pp. 376-387.

*Primary Examiner*—Kamal A. Saeed
(74) *Attorney, Agent, or Firm*—George W. Johnston; Patricia S. Rocha-Tramaloni

(57) ABSTRACT

Novel diaminothiazoles of formula (I):

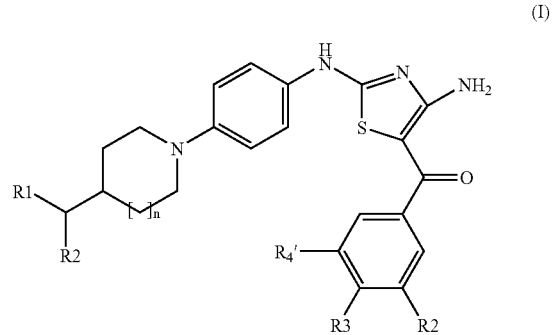

are discussed. These compounds selectively inhibit the activity of Cdk4 and are thus useful in the treatment or control of cancer, in particular, the treatment or control of solid tumors. This invention also provides pharmaceutical compositions containing such compounds and methods of treating or controlling cancer, most particularly, the treatment or control of breast, lung, colon, and prostate tumors.

27 Claims, No Drawings

DIAMINOTHIAZOLES

PRIORITY TO RELATED APPLICATIONS

This application claims the benefit of Provisional Application Ser. No. 60/563,712, filed Apr. 20, 2004.

FIELD OF THE INVENTION

The present invention provides novel diaminothiazoles of formula (I):

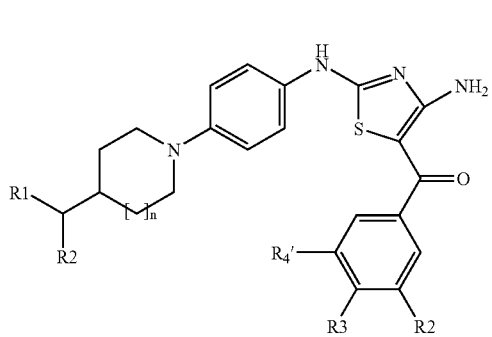

The novel diaminothiazoles are capable of selectively inhibiting the activity of Cdk4. These compounds are useful in the treatment or control of cancer, in particular, the treatment or control of solid tumors. This invention also provides pharmaceutical compositions containing such compounds and methods of treating or controlling cancer, most particularly, the treatment or control of breast, lung, colon, and prostate tumors.

BACKGROUND OF THE INVENTION

Uncontrolled cell proliferation is the hallmark of cancer. Cancerous tumor cells typically have some form of damage to the genes that directly or indirectly regulate the cell-division cycle.

The progression of cells through the various phases of the cell cycle is regulated by a series of multienzyme complexes consisting of a regulatory protein, a cyclin, and a kinase. These kinases are called cyclin-dependent kinases (Cdks). The Cdks are expressed throughout the cell cycle, while the levels of the cyclins vary depending on the stage of the cell cycle.

The transition from $G_1$ phase into S phase is regulated by the complex of Cdk4 with cyclin D. This complex phosphorylates the tumor suppressor protein Retinoblastoma (pRb), releasing the transcription factor E2F and allowing the expression of genes required in S phase (Nevins, J. R. Science 1992, 258, 424–429). Blocking the activity of the Cdk4/cyclin D complex arrests the cell cycle in $G_1$ phase. For example, the proteins of the INK4 family, including p16$^{INK4a}$, which block the kinase activity of the Cdk4/cyclin D complex, cause arrest in $G_1$ (Sherr, C. J. Science 1996, 274, 1672–1677).

Recent experiments show that the complex of Cdk4 with cyclin D3 also plays a role in cell cycle progression through $G_2$ phase. Inhibition of this complex, either by p16 or using a dominant negative Cdk4, results in arrest in $G_2$ phase in cells that do not express pRb (Gabrielli B. G. et al. *J. Biol. Chem.* 1999, 274, 13961–13969).

Numerous defects in the pRb pathway have been shown to be involved in various cancers. For example, overexpression of Cdk4 has been observed in cases of hereditary melanoma (Webster, K. R. *Exp. Opin. Invest. Drugs* 1998, 7, 865–887); cyclin D is overexpressed in many human cancers (Sherr, C. J. *Science* 1996, 274, 1672–1677); p16 is mutated or deleted in many tumors (Webster, K. R. *Exp. Opin. Invest. Drugs* 1998, 7, 865–887); and pRb function is lost through mutation or deletion in many human cancers (Weinberg, R. A. *Cell* 1995, 81, 323–330). Defects in this pathway have also been shown to have an effect on prognosis. For example, loss of p16 is correlated with poor prognosis in non-small-cell lung carcinoma (NSCLC) and malignant melanoma (Tsihlias, J. et al. *Annu. Rev. Med.* 1999, 50, 401–423).

Because of the involvement of the Cdk4/cyclin D/pRb pathway in human cancer through its role in regulating progression of the cell cycle from $G_1$ to S phase, and the potential therapeutic benefit from modulating this pathway, there has been considerable interest in agents that inhibit or promote elements of this pathway. For example, effects on cancer cells have been shown using antibodies, antisense oligonucleotides and overexpression or addition of proteins involved in the pathway. See, e.g., Lukas, J. et al. *Nature* 1995, 79, 573–582; Nevins, J. R. *Science* 1992, 258, 424–429; Lim, I. K. et al. *Molecular Carcinogenesis* 1998, 23, 25–35; Tam, S. W. et al. *Oncogene* 1994, 9, 2663–2674; Driscoll, B. et al. *Am. J. Physiol.* 1997, 273 (*Lung Cell. Mol. Physiol.*), L941–L949; and Sang, J. et al. *Chin. Sci. Bull.* 1999, 44, 541–544). There is thus an extensive body of literature validating the use of compounds inhibiting targets in the Cdk4 pathway as anti-proliferative therapeutic agents.

Several small molecules have been identified as Cdk inhibitors and have been the subject of recent reviews (Webster, Exp. Opin. Invest. Drugs, Vol. 7, pp. 865–887 (1988), Stover, et al., Curr. Opin. In Drug Discov. and Devel., vol. 2, pp. 274–285 (1999) and Toogood, Med. Res. Rev., vol. 6, pp 487–498 (2001).

It is thus desirable to identify chemical inhibitors of Cdk4 kinase activity. It is particularly desirable to identify small molecule compounds that may be readily synthesized and are effective in inhibiting Cdk4 or Cdk4/cyclin complexes, for treating one or more types of tumors.

There are several examples of small molecule inhibitors of the cyclin-dependent kinases, including Cdk4 (Rosania, G. R. et al. *Exp. Opin. Ther. Patents* 2000, 10, 215–230). Several of these compounds inhibit multiple targets.

For example, Flavopiridol (Aventis)

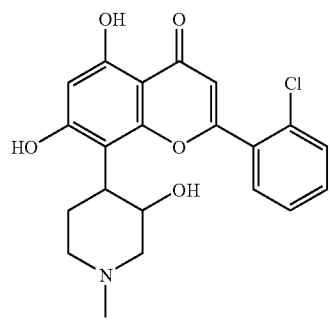

is in Phase II clinical trials for lymphoma and multiple myeloma and also for the treatment of solid tumors. It is said to inhibit Cdk1, Cdk2 and Cdk4 and block cells in both G1 and G2 phases. It is also a weaker inhibitor of PKC and EGFR (Senderowicz, A. M. et al. *J. Natl. Cancer Inst* 2000, 92, 376–387).

WO9716447 (Mitotix) discloses the following compounds related to flavopiridol

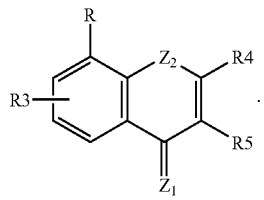

Some of these compounds are stated to inhibit Cdk4.

WO9943675 and WO9943676 (Hoechst) disclose the following purine derivatives

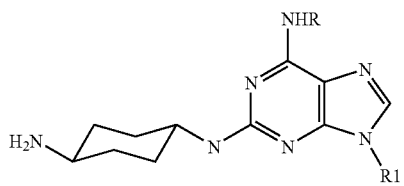

which are stated to inhibit Cdk2 and Cdk4.

WO9833798 (Warner-Lambert) discloses the following pyridopyrimidines

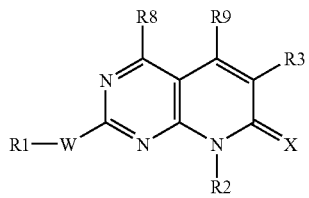

These compounds are stated to inhibit the cyclin dependent kinases Cdk1, Cdk2, and Cdk4. Some of these compounds also inhibit the receptor tyrosine kinases PDGFR and EGFR, and the cellular Src protein kinase, c-Src.

WO9909030 (Warner-Lambert) discloses naphthyridinones

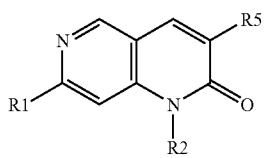

that inhibit PDGFR, FGFR, c-Src, and the cyclin dependent kinases Cdk1, Cdk2, and Cdk4.

WO0039101 (AstraZeneca) discloses diaminopyrimidines

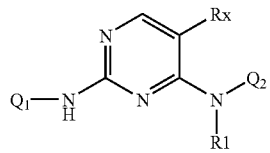

that inhibit Cdk4 and FAK3.

WO0012485 (Zeneca) discloses diaminopyrimidines

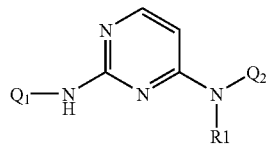

that inhibit Cdk4 and FAK3.

WO9924416 (Bristol-Myers Squibb) discloses aminothiazole inhibitors of formula

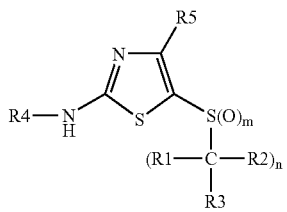

The compounds inhibit Cdk1, Cdk2 and Cdk4.

WO9921845 (Agouron) discloses diaminothiazole inhibitors of Cdk1, Cdk2 and Cdk4, having the following structure

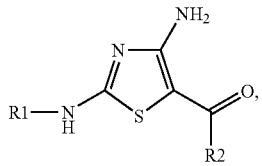

where R1 and R2 are ring systems. This patent application states that when the $R^2$ ring system does not bear an ortho substituent, the compounds lack potency and selectivity as inhibitors of Cdk4.

WO0075120 (Agouron) discloses diaminothiazole inhibitors of protein kinases including VEGF-R, FGF-R, CDK complexes, TEK, CHK1, LCK, and FAK, having the following structure

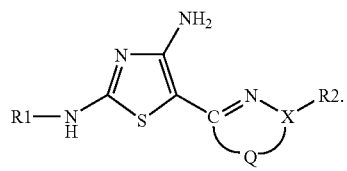

WO0026202 (Pharmacia & Upjohn S.p.A., Italy) discloses 2-amino-thiazole derivatives of formula

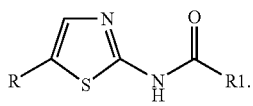

These compounds are asserted to be antitumor agents operating by a kinase dependent mechanism.

WO1056567 (Novo Nordisk) discloses diaminothiazoles of formula

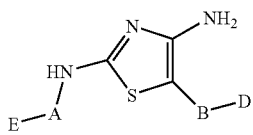

as GSK-3 inhibitors. These compounds are stated to be useful in treating type 2 diabetes.

WO0160816 (Amgen) discloses pyrimidines of formula

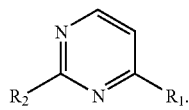

These compounds are asserted to modulate kinase activity.

WO0179198 (Agouron) discloses amino-pyrazoles of formula

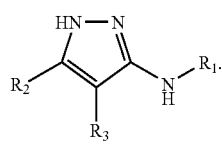

These compounds are asserted to mediate/inhibit Cdks, VEGF, and CHK1, and to be useful in treating cancer.

WO 02/12250 A2 (Agouron) discloses pyrazole-thiazole compounds of

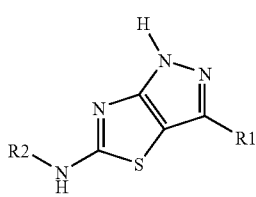

These compounds are inserted to be Cdk4/Cdk2 inhibitors.

WO 2004/014904 (Agouron) discloses compounds of formula

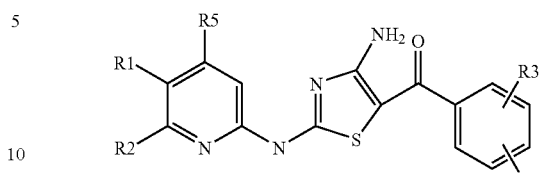

The compounds are said to be protein kinase inhibitors, particularly for Cdk2 and Cdk4.

WO 03/097048 (F. Hoffmann-LaRoche AG) discloses compounds of formula:

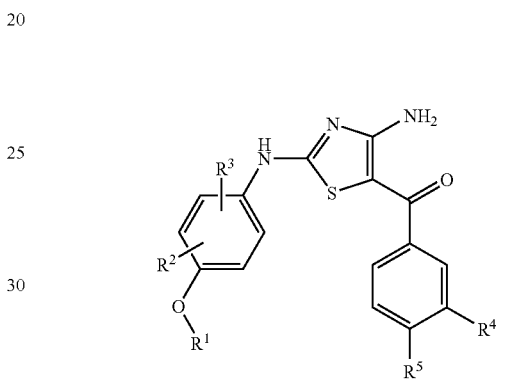

These compounds are said to inhibit cyclin-dependent kinase 4 (Cdk4) and to be selective against Cdk2 and Cdk1

It is thus desirable to provide small molecule inhibitors of Cdk4 that preferably are selective against other Cdks. That is, the small molecule preferably is selectively more inhibitory of Cdk4 than Cdk1 or Cdk2, most preferably selectively more inhibitory of Cdk4 than Cdk1 and Cdk2. In a preferred embodiment, the compounds of the invention are at least five times more inhibitory of Cdk4 than Cdk1 or Cdk2, most preferably five times more inhibitory of Cdk4 than Cdk1 and Cdk2. Selectivity is desirable because of the potential concomitant toxicity and other undesirable complications that may follow from inhibiting multiple targets. Thus, a compound that exhibits selectivity against Cdk2 and Cdk1 is expected to have a better safety profile than a compound that is not selective between Cdk4, Cdk2 and Cdk1. The present invention provides such compounds, compositions containing such compounds, and methods of using such compounds in the treatment or control of breast, colon, lung, and prostate tumors.

SUMMARY OF THE INVENTION

The present invention provides novel diaminothiazoles capable of selectively inhibiting the activity of Cdk4. These compounds are useful in the treatment or control of cancer, in particular the treatment or control of solid tumors. In particular this invention provides a compound of formula (I):

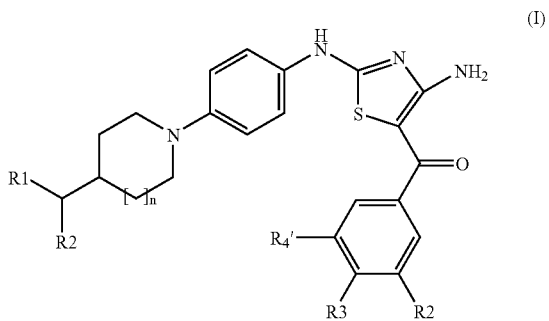

(I)

wherein, n is 0 or 1;

$R^1$ and $R^2$ are each independently selected from the group consisting of H, lower alkyl, $CO_2R^5$, $SO_2R^6$, and $COR^6$;

or alternatively, $R^1$ and $R^2$ can form a ring having a total of 5–7 ring atoms, said ring comprising carbon atoms, said carbon atoms optionally being replaced by one or two heteroatoms, and said ring atoms optionally being substituted by $OR^6$;

$R^3$ is selected from the group consisting of H, lower alkyl, O-lower alkyl, halogen, OH, CN, $NO_2$, and COOH;

$R^4$ is selected from the group consisting of H, lower alkyl, cycloalkyl, O-lower alkyl, halogen, $NO_2$, S-lower alkyl, $CF_3$, $NR^5R^6$, $CONR^7R^8$, $CO_2R^6$, OH, and CN;

or alternatively, $R^3$ and $R^4$, together with the two carbon atoms and bond between them from the benzene ring to which $R^3$ and $R^4$ are attached, can form a ring having 5–7 ring atoms, said 5–7 atom ring comprising carbon atoms, said carbon atoms optionally being replaced by one or two heteroatoms, and said ring atoms optionally being substituted by $C_1$–$C_4$ alkyl and $CO_2R^6$;

$R^{4'}$ is H or halogen;

$R^5$ and $R^6$ are each independently selected from the group consisting of H, lower alkyl, cycloalkyl, heterocycle, aryl, and aryl substituted by lower alkoxy, halogen, or CN;

$R^7$ and $R^8$ are each independently selected from the group consisting of H, lower alkyl, lower alkyl substituted by $OR^5$, and $NR^5R^6$;

or alternatively, the group $NR^7R^8$ can form a ring having a total of 5–7 ring atoms, said ring atoms comprising in addition to the nitrogen to which $R^7$ and $R^8$ are bonded, carbon ring atoms, said carbon ring atoms optionally being replaced by one or two heteroatoms, and said ring atoms being optionally substituted by $C_1$–$C_4$ alkyl, $COR^6$, $CONR^5R^6$, or $CO_2R^6$; or a pharmaceutically acceptable salt or ester thereof.

The present invention also provides pharmaceutical compositions comprising a therapeutically effective amount of one or more compounds of formula (I) and a pharmaceutically acceptable carrier or excipient. Specifically, the invention provides a pharmaceutical composition which is suitable for parenteral administration.

The present invention further provides a method for treating a solid breast or colon, tumor comprising administering to a subject in need thereof a therapeutically effective amount of a compound of formula (I), its salt and/or ester.

The present invention further provides novel intermediate compounds useful in the preparation of compounds of formula (I).

DETAILED DESCRIPTION OF THE INVENTION

Definitions

As used herein, the following terms shall have the following definitions.

"Aryl" means a monovalent, monocyclic or bicyclic, aromatic carbocyclic hydrocarbon group, preferably a 6–10 membered aromatic system. Preferred aryl groups include, but are not limited to, phenyl, naphthyl, and tolyl.

"Cycloalkyl" means a non-aromatic, partially or completely saturated cyclic aliphatic hydrocarbon group containing 3 to 8 atoms, preferably 3 to 6 atoms. Examples of cycloalkyl groups include cyclopropyl, cyclopentyl and cyclohexyl.

"Effective amount" means an amount that is effective to prevent, alleviate or ameliorate symptoms of disease or prolong the survival of the subject being treated.

"Halogen" means fluorine, chlorine, bromine or iodine. Preferably, the halogen is fluorine.

"Heteroatom" means an atom selected from N, O and S. Preferred heteroatoms are N and O.

"Heterocycle" means a saturated or partially unsaturated, nonaromatic cyclic radical having a total of 3–8 ring atoms in which 1–3 atoms may be heteroatoms independently selected from N, O, and S, the remaining ring atoms being C. Examples of preferred heterocycles are piperidine, piperazine, pyrrolidine, morpholine, indoline, tetrahydropyranyl, thiomorpholine, pentamethylene sulfide, and pentamethylene sulfone.

"$IC_{50}$" refers to the concentration of a particular compound according to the invention required to inhibit 50% of a specific measured activity. $IC_{50}$ can be measured, inter alia, as described in the Examples.

"Lower alkyl" denotes a straight-chain or branched saturated aliphatic hydrocarbon having 1 to 6 carbon atoms, preferably 1 to 4 carbon atoms. Typical lower alkyl groups include methyl, ethyl, propyl, isopropyl, butyl, t-butyl, 2-butyl, pentyl, hexyl, and the like.

"Pharmaceutically acceptable ester" refers to a conventionally esterified compound of formula (I) having a carboxyl group, which ester retains the biological effectiveness and properties of the compounds of formula (I) and is cleaved in vivo (in the organism) to the corresponding active carboxylic acid.

Examples of lower alkyl esters are the methyl, ethyl, and n-propyl esters, and the like. Examples of lower alkyl substituted esters are the diethylaminoethyl, 2-(4-morpholinyl)ethyl, 2-(4-methylpiperazin-1-yl)ethyl esters, and the like. Examples of acyloxyalkyl esters are the pivaloxymethyl, 1-acetoxyethyl, and acetoxymethyl esters. Examples of carbonate esters are the 1-(ethoxycarbonyloxy)ethyl and 1-(cyclohexyloxycarbonyloxy)ethyl esters. Examples of aminocarbonylmethyl esters are the N,N-dimethylcarbamoylmethyl and carbamoylmethyl esters.

Further information concerning examples of and the use of esters for the delivery of pharmaceutical compounds is available in Design of Prodrugs, Bundgaard H. ed. (Elsevier, 1985). See also, H. Ansel et. al., Pharmaceutical Dosage Forms and Drug Delivery Systems (6th Ed. 1995) at pp. 108–109; Krogsgaard-Larsen, et. al., Textbook of Drug Design and Development (2d Ed. 1996) at pp. 152–191.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

"Pharmaceutically acceptable," such as pharmaceutically acceptable carrier, excipient, etc., means pharmacologically acceptable and substantially non-toxic to the subject to which the particular compound is administered.

"Ring", when describing a chemical ring, unless otherwise indicated, may be saturated or unsaturated.

"Substituted," as in "lower alkyl substituted by" means that the substitution can occur at one or more positions and, unless otherwise indicated, that the substituents at each substitution site are independently selected from the specified options.

"Therapeutically effective amount" means an amount of at least one compound of Formula I, or a pharmaceutically acceptable salt or ester thereof, that significantly inhibits proliferation and/or prevents differentiation of a human tumor cell, including human tumor cell lines.

In accordance with the present invention, a compound of formula (I) is provided

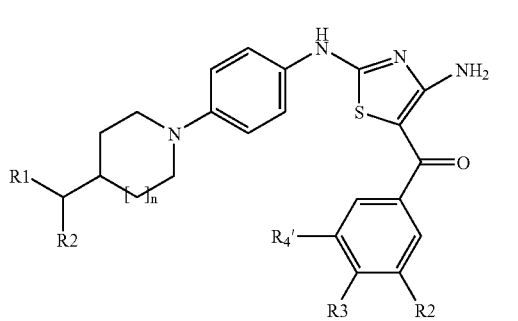

wherein, n is 0 or 1;

$R^1$ and $R^2$ are each independently selected from the group consisting of H, lower alkyl, $CO_2R^5$, $SO_2R^6$, and $COR^6$;

or alternatively, $R^1$ and $R^2$ can form a ring having a total of 5–7 ring atoms, said ring comprising carbon atoms, said carbon atoms optionally being replaced by one or two heteroatoms, and said ring atoms optionally being substituted by $OR^6$;

$R^3$ is selected from the group consisting of H, lower alkyl, O-lower alkyl, halogen, OH, CN, $NO_2$, and COOH;

$R^4$ is selected from the group consisting of H, lower alkyl, cycloalkyl, O-lower alkyl, halogen, $NO_2$, S-lower alkyl, $CF_3$, $NR^5R^6$, $CONR^7R^8$, $CO_2R^6$, OH, and CN;

or alternatively, $R^3$ and $R^4$, together with the two carbon atoms and bond between them from the benzene ring to which $R^3$ and $R^4$ are attached, can form a ring having 5–7 ring atoms, said 5–7 atom ring comprising carbon atoms, said carbon atoms optionally being replaced by one or two heteroatoms, and said ring atoms optionally being substituted by $C_1$–$C_4$ alkyl and $CO_2R^6$;

$R^{4'}$ is H or halogen;

$R^5$ and $R^6$ are each independently selected from the group consisting of H, lower alkyl, cycloalkyl, heterocycle, aryl, and aryl substituted by lower alkoxy, halogen, or CN;

$R^7$ and $R^8$ are each independently selected from the group consisting of H, lower alkyl, lower alkyl substituted by $OR^5$, and $NR^5R^6$;

or alternatively, the group $NR^7R^8$ can form a ring having a total of 5–7 ring atoms, said ring atoms comprising in addition to the nitrogen to which $R^7$ and $R^8$ are bonded, carbon ring atoms, said carbon ring atoms optionally being replaced by one or two heteroatoms, and said ring atoms being optionally substituted by $C_1$–$C_4$ alkyl, $COR^6$, $CONR^5R^6$, or $CO_2R^6$; or a pharmaceutically acceptable salt or ester thereof.

In Formula (I), n is 0 or 1, preferably, n is 1.

$R^1$ and $R^2$ are each independently selected from the group consisting of H, lower alkyl, $CO_2R^5$, $SO_2R^6$, and $COR^6$. Preferably, $R^1$ and $R^2$ are independently selected from the group consisting of H, lower alkyl, and $CO_2R^5$. Alternatively, $R^1$ and $R^2$ may form a ring having a total of 5 to 7 ring atoms, said ring comprising carbon atoms, said carbon atoms optionally being replaced by up to two heteroatoms, and said ring atoms optionally being substituted by $OR^6$. Preferably, $R^1$ and $R^2$ form a ring having 5–6 ring atoms.

$R^3$ is selected from the group consisting of H, lower alkyl, O-lower alkyl, halogen, OH, CN, $NO_2$, and COOH. Preferably, $R^3$ is selected from the group consisting of H, lower alkyl, and O-lower alkyl.

$R^4$ is selected from the group consisting of H, lower alkyl, cycloalkyl, O-lower alkyl, halogen, $NO_2$, S-lower alkyl, $CF_3$, $NR^5R^6$, $CONR^7R^8$, $CO_2R^6$, OH, and CN. Preferably, $R^4$ is selected from the group consisting of H, lower alkyl, halogen and O-lower alkyl.

Alternatively, $R^3$ and $R^4$, together with the two carbon atoms and bond between them from the benzene ring to which $R^3$ and $R^4$ are attached, can form a ring having 5–7 ring atoms, said 5–7 atom ring comprising carbon atoms, said carbon atoms optionally being replaced by one or two heteroatoms, and said ring atoms optionally being substituted by $C_1$–$C_4$ alkyl and $CO_2R^6$ Preferably, $R^3$ and $R^4$ form a ring having 5–6 ring atoms.

$R^{4'}$ is H or halogen. Preferably, $R^{4'}$ is H.

$R^5$ and $R^6$ are each independently selected from the group consisting of H, lower alkyl, cycloalkyl, heterocycle, aryl, and aryl substituted by lower alkoxy, halogen, or CN. Preferably, $R^5$ and $R^6$ are independently selected from the group consisting of H, lower alkyl, and cycloalkyl.

$R^7$ and $R^8$ are each independently selected from the group consisting of H, lower alkyl, lower alkyl substituted by $OR^5$, and $NR^5R^6$. Preferably, $R^7$ and $R^8$ are independently selected from H and lower alkyl.

Alternatively, the group $NR^7R^8$ can form a ring having a total of 5–7 ring atoms, said ring atoms comprising in addition to the nitrogen to which $R^7$ and $R^8$ are bonded, carbon ring atoms, said carbon ring atoms optionally being replaced by one or two heteroatoms, and said ring atoms being optionally substituted by $C_1$–$C_4$ alkyl, $COR^6$, $CONR^5R^6$, or $CO_2R^6$ Preferably, the group $NR^7R^8$ can form a ring having a total of 5–6 ring atoms.

Examples of compounds of Formula (1) include:
{2-Amino-5-[4-(4-pyrrolidin-1-yl-piperidin-1-yl)-phenylamino]-4H-pyrrol-3-yl}-(3-fluoro-4-methoxy-phenyl)-methanone (Example 23)
{4-Amino-2-[4-(4-pyrrolidin-1-yl-piperidin-1-yl)-phenylamino]-thiazol-5-yl}-(3-fluoro-phenyl)-methanone (Example 24)
{4-Amino-2-[4-(4-pyrrolidin-1-yl-piperidin-1-yl)-phenylamino]-thiazol-5-yl}-benzo[1,3]dioxol-5-yl-methanone (Example 25)
{4-Amino-2-[4-(4-pyrrolidin-1-yl-piperidin-1-yl)-phenylamino]-thiazol-5-yl}-(2,3-dihydro-benzo[1,4]dioxin-6-yl)-methanone (Example 26)
{{4-Amino-2-[4-(4-pyrrolidin-1-yl-piperidin-1-yl)-phenylamino]-thiazol-5-yl}-(3-methoxy-phenyl)-methanone (Example 27)
{4-Amino-2-[4-(4-pyrrolidin-1-yl-piperidin-1-yl)-phenylamino]-thiazol-5-yl}-(4-hydroxy-phenyl)-methanone (Example 28)
[4-Amino-2-(4-[1,4']bipiperidinyl-1'-yl-phenylamino)-thiazol-5-yl]-(4-hydroxy-phenyl)-methanone (Example 29)
[4-Amino-2-(4-[1,4']bipiperidinyl-1'-yl-phenylamino)-thiazol-5-yl]-(3-fluoro-phenyl)-methanone (Example 30)
[4-Amino-2-(4-[1,4']bipiperidinyl-1'-yl-phenylamino)-thiazol-5-yl]-(3-fluoro-4-methoxy-phenyl)-methanone (Example 31)
[4-Amino-2-(4-[1,4']bipiperidinyl-1'-yl-phenylamino)-thiazol-5-yl]-benzo[1,3]dioxol-5-yl-methanone (Example 32)
[4-Amino-2-(4-[1,4']bipiperidinyl-1'-yl-phenylamino)-thiazol-5-yl]-(2,3-dihydro-benzo[1,4]dioxin-6-yl)-methanone (Example 33)
[4-Amino-2-(4-[1,4']bipiperidinyl-1'-yl-phenylamino)-thiazol-5-yl]-(3-methoxy-phenyl)-methanone (Example 34)
{4-Amino-2-[4-(3-hydroxy-[1,4']bipiperidinyl-1'-yl)-phenylamino]-thiazol-5-yl}-(3-fluoro-phenyl)-methanone (Example 35)
{4-Amino-2-[4-(3-hydroxy-[1,4']bipiperidinyl-1'-yl)-phenylamino]-thiazol-5-yl}-(3-fluoro-4-methoxy-phenyl)-methanone (Example 36)
{4-Amino-2-[4-(3-hydroxy-[1,4']bipiperidinyl-1'-yl)-phenylamino]-thiazol-5-yl}-benzo[1,3]dioxol-5-yl-methanone (Example 37)
{4-Amino-2-[4-(3-hydroxy-[1,4']bipiperidinyl-1'-yl)-phenylamino]-thiazol-5-yl}-(2,3-dihydro-benzo[1,4]dioxin-6-yl)-methanone (Example 38)
{4-Amino-2-[4-(3-hydroxy-[1,4']bipiperidinyl-1'-yl)-phenylamino]-thiazol-5-yl}-(2,3-dihydro-benzo[1,4]dioxin-6-yl)-methanone (Example 39)
{4-Amino-2-[4-(3-hydroxy-[1,4']bipiperidinyl-1'-yl)-phenylamino]-thiazol-5-yl}-(4-hydroxy-phenyl)-methanone (Example 40)
{4-Amino-2-[4-(4-dimethylamino-piperidin-1-yl)-phenylamino]-thiazol-5-yl}-(3-fluoro-phenyl)-methanone (Example 41)
{4-Amino-2-[4-(4-dimethylamino-piperidin-1-yl)-phenylamino]-thiazol-5-yl}-(3-fluoro-4-methoxy-phenyl)-methanone (Example 42)
{4-Amino-2-[4-(4-dimethylamino-piperidin-1-yl)-phenylamino]-thiazol-5-yl}-benzo[1,3]dioxol-5-yl-methanone (Example 43)
{4-Amino-2-[4-(4-dimethylamino-piperidin-1-yl)-phenylamino]-thiazol-5-yl}-(2,3-dihydro-benzo[1,4]dioxin-6-yl)-methanone (Example 44)
{4-Amino-2-[4-(4-dimethylamino-piperidin-1-yl)-phenylamino]-thiazol-5-yl}-(3-methoxy-phenyl)-methanone (Example 45)
{4-Amino-2-[4-(4-dimethylamino-piperidin-1-yl)-phenylamino]-thiazol-5-yl}-(4-hydroxy-phenyl)-methanone (Example 46)
4-{4-Amino-2-[4-(4-dimethylamino-piperidin-1-yl)-phenylamino]-thiazole-5-carbonyl}-benzonitrile (Example 47)
{4-Amino-2-[4-(4-dimethylamino-piperidin-1-yl)-phenylamino]-thiazol-5-yl}-(4-nitro-phenyl)-methanone (Example 48)
{4-Amino-2-[4-(4-dimethylamino-piperidin-1-yl)-phenylamino]-thiazol-5-yl}-(3-hydroxy-phenyl)-methanone (Example 50)
4-{4-Amino-2-[4-(3-hydroxy-[1,4']bipiperidinyl-1'-yl)-phenylamino]-thiazole-5-carbonyl}-benzonitrile (Example 51)
{4-Amino-2-[4-(3-hydroxy-[1,4']bipiperidinyl-1'-yl)-phenylamino]-thiazol-5-yl}-(4-nitro-phenyl)-methanone (Example 52)
{4-Amino-2-[4-(4-pyrrolidin-1-yl-piperidin-1-yl)-phenylamino]-thiazol-5-yl}-(4-nitro-phenyl)-methanone (Example 53)
4-{4-Amino-2-[4-(4-pyrrolidin-1-yl-piperidin-1-yl)-phenylamino]-thiazole-5-carbonyl}-benzonitrile (Example 54)
4-[4-Amino-2-(4-[1,4']bipiperidinyl-1'-yl-phenylamino)-thiazole-5-carbonyl]-benzonitrile (Example 55)
[4-Amino-2-(4-[1,4']bipiperidinyl-1'-yl-phenylamino)-thiazol-5-yl]-(4-nitro-phenyl)-methanone (Example 56)
[4-Amino-2-(4-[1,4']bipiperidinyl-1'-yl-phenylamino)-thiazol-5-yl]-(3,5-difluoro-phenyl)-methanone (Example 57)
[4-Amino-2-(4-[1,4']bipiperidinyl-1'-yl-phenylamino)-thiazol-5-yl]-(4-chloro-phenyl)-methanone (Example 58)
[4-Amino-2-(4-[1,4']bipiperidinyl-1'-yl-phenylamino)-thiazol-5-yl]-(3,4-difluoro-phenyl)-methanone (Example 59)
[4-Amino-2-(4-[1,4']bipiperidinyl-1'-yl-phenylamino)-thiazol-5-yl]-(3,4-dichloro-phenyl)-methanone (Example 60)
[4-Amino-2-(4-[1,4']bipiperidinyl-1'-yl-phenylamino)-thiazol-5-yl]-(4-fluoro-phenyl)-methanone (Example 61)
[4-Amino-2-(4-[1,4']bipiperidinyl-1'-yl-phenylamino)-thiazol-5-yl]-(4-chloro-3-nitro-phenyl)-methanone (Example 62)
4-[4-Amino-2-(4-[1,4']bipiperidinyl-1'-yl-phenylamino)-thiazole-5-carbonyl]-benzoic acid (Example 63)
3-[4-Amino-2-(4-[1,4']bipiperidinyl-1'-yl-phenylamino)-thiazole-5-carbonyl]-benzonitrile (Example 64)
[4-Amino-2-(4-[1,4']bipiperidinyl-1'-yl-phenylamino)-thiazol-5-yl]-(3-hydroxy-phenyl)-methanone (Example 65)
{4-Amino-2-[4-(4-pyrrolidin-1-yl-piperidin-1-yl)-phenylamino]-thiazol-5-yl}-(3,5-difluoro-phenyl)-methanone (Example 66)
{4-Amino-2-[4-(4-pyrrolidin-1-yl-piperidin-1-yl)-phenylamino]-thiazol-5-yl}-(4-chloro-phenyl)-methanone (Example 67)
{4-Amino-2-[4-(4-pyrrolidin-1-yl-piperidin-1-yl)-phenylamino]-thiazol-5-yl}-(3,4-difluoro-phenyl)-methanone (Example 68)
[{4-Amino-2-[4-(4-pyrrolidin-1-yl-piperidin-1-yl)-phenylamino]-thiazol-5-yl}-(3,4-dichloro-phenyl)-methanone (Example 69)
{4-Amino-2-[4-(4-pyrrolidin-1-yl-piperidin-1-yl)-phenylamino]-thiazol-5-yl}-(4-fluoro-phenyl)-methanone (Example 70)
{4-Amino-2-[4-(4-pyrrolidin-1-yl-piperidin-1-yl)-phenylamino]-thiazol-5-yl}-(4-chloro-3-nitro-phenyl)-methanone (Example 71)
3-{4-Amino-2-[4-(4-pyrrolidin-1-yl-piperidin-1-yl)-phenylamino]-thiazole-5-carbonyl}-benzonitrile (Example 72)

{4-Amino-2-[4-(3-hydroxy-[1,4']bipiperidinyl-1'-yl)-phenylamino]-thiazol-5-yl}-(3,5-difluoro-phenyl)-methanone (Example 73)

{4-Amino-2-[4-(3-hydroxy-[1,4']bipiperidinyl-1'-yl)-phenylamino]-thiazol-5-yl}-4-chloro-phenyl)-methanone (Example 74)

{4-Amino-2-[4-(3-hydroxy-[1,4']bipiperidinyl-1'-yl)-phenylamino]-thiazol-5-yl}-(3,4-difluoro-phenyl)-methanone (Example 75)

{4-Amino-2-[4-(3-hydroxy-[1,4']bipiperidinyl-1'-yl)-phenylamino]-thiazol-5-yl}-(3,4-dichloro-phenyl)-methanone (Example 76)

{4-Amino-2-[4-(3-hydroxy-[1,4']bipiperidinyl-1'-yl)-phenylamino]-thiazol-5-yl}-(4-fluoro-phenyl)-methanone (Example 77)

{4-Amino-2-[4-(3-hydroxy-[1,4']bipiperidinyl-1'-yl)-phenylamino]-thiazol-5-yl}-(4-chloro-3nitro-phenyl)-methanone (Example 78)

4-{4-Amino-2-[4-(3-hydroxy-[1,4']bipiperidinyl-1'-yl)-phenylamino]-thiazole-5-carbonyl}-benzoic acid (Example 79)

3-{4-Amino-2-[4-(3-hydroxy-[1,4']bipiperidinyl-1'-yl)-phenylamino]-thiazole-5-carbonyl}-benzonitrile (Example 80)

{4-Amino-2-[4-(3-hydroxy-[1,4']bipiperidinyl-1'-yl)-phenylamino]-thiazol-5-yl}-(3-hydroxy-phenyl)-methanone (Example 81)

{4-Amino-2-[4-(4-dimethylamino-piperidin-1-yl)-phenylamino]-thiazol-5-yl}-(3,5-difluoro-phenyl)-methanone (Example 82)

{4-Amino-2-[4-(4-dimethylamino-piperidin-1-yl)-phenylamino]-thiazol-5-yl}-(4-chloro-phenyl)-methanone (Example 83)

{4-Amino-2-[4-(4-dimethylamino-piperidin-1-yl)-phenylamino]-thiazol-5-yl}-(3,4-difluoro-phenyl)-methanone (Example 84)

{4-Amino-2-[4-(4-dimethylamino-piperidin-1-yl)-phenylamino]-thiazol-5-yl}-(3,4-dichloro-phenyl)-methanone (Example 85)

{4-Amino-2-[4-(4-dimethylamino-piperidin-1-yl)-phenylamino]-thiazol-5-yl}-(4-fluoro-phenyl)-methanone (Example 86)

{4-Amino-2-[4-(4-dimethylamino-piperidin-1-yl)-phenylamino]-thiazol-5-yl}-(4-chloro-3-nitro-phenyl)-methanone (Example 87)

3-{4-Amino-2-[4-(4-dimethylamino-piperidin-1-yl)-phenylamino]-thiazole-5-carbonyl}-benzonitrile (Example 88)

[4-Amino-2-(4-[1,4']bipiperidinyl-1'-yl-phenylamino)-thiazol-5-yl]-(3-nitro-phenyl)-methanone (Example 89)

{4-Amino-2-[4-(4-pyrrolidin-1-yl-piperidin-1-yl)-phenylamino]-thiazol-5-yl}-(3-nitro-phenyl)-methanone (Example 90)

{4-Amino-2-[4-(3-hydroxy-[1,4']bipiperidinyl-1'-yl)-phenylamino]-thiazol-5-yl}-(3-nitro-phenyl)-methanone (Example 91)

{4-Amino-2-[4-(4-dimethylamino-piperidin-1-yl)-phenylamino]-thiazol-5-yl}-(3-nitro-phenyl)-methanone (Example 92)

5-{4-Amino-2-[4-(4-dimethylamino-piperidin-1-yl)-phenylamino]-thiazole-5-carbonyl}-2-hydroxy-benzamide (Example 93)

5-{4-Amino-2-[4-(4-pyrrolidin-1-yl-piperidin-1-yl)-phenylamino]-thiazole-5-carbonyl}-2-hydroxy-benzamide (Example 94)

{4-Amino-2-[4-(4-pyrrolidin-1-yl-piperidin-1-yl)-phenylamino]-thiazol-5-yl}-(3-hydroxy-phenyl)-methanone (Example 96)

{4-Amino-2-[4-(4-pyrrolidin-1-yl-piperidin-1-yl)-phenylamino]-thiazol-5-yl}-(3-hydroxy-phenyl)-methanone (Example 97)

{4-Amino-2-[4-(4-morpholin4-yl-piperidin-1-yl)-phenylamino]-thiazol-5-yl}-(2,3-dihydro-benzo[1,4]dioxin-6yl)-methanone (Example 98)

{4-Amino-2-[4-(4-morpholin4-yl-piperidin-1-yl)-phenylamino]-thiazol-5-yl}-(3-fluoro-phenyl)-methanone (Example 99)

{4-Amino-2-[4-(4-morpholin4-yl-piperidin-1-yl)-phenylamino]-thiazol-5-yl}-(3-fluoro-4-methoxy-phenyl)-methanone (Example 100)

{4-Amino-2-[4-(4-morpholin-4-yl-piperidin-1-yl)-phenylamino]-thiazol-5-yl}-benzo[1,3]dioxol-5-yl-methanone (Example 101)

{4-Amino-2-[4-(4-morpholin-4-yl-piperidin-1-yl)-phenylamino]-thiazol-5-yl}-(3-methoxy-phenyl)-methanone (Example 102)

{4-Amino-2-[4-(4-morpholin-4-yl-piperidin-1-yl)-phenylamino]-thiazol-5-yl}-(3-hydroxy-phenyl)-methanone (Example 103)

3-{4-Amino-2-[4-(4-morpholin4-yl-piperidin-1-yl)-phenylamino]-thiazole-5-carbonyl}-benzonitrile (Example 104)

{4-Amino-2-[4-(4-morpholin-4-yl-piperidin-1-yl)-phenylamino]-thiazol-5-yl}-(3-nitro-phenyl)-methanone (Example 105)

{4-Amino-2-[4-(4-morpholin-4-yl-piperidin-1-yl)-phenylamino]-thiazol-5-yl}-(4-methoxy-3-nitro-phenyl)-methanone (Example 106)

{4-Amino-2-[4-(4-pyrrolidin-1-yl-piperidin-1-yl)-phenylamino]-thiazol-5-yl}-(4-methoxy-3-nitro-phenyl)-methanone (Example 107)

[4-Amino-2-(4-[1,4']bipiperidinyl-1'-yl-phenylamino)-thiazol-5-yl]-(4-methoxy-3-nitro-phenyl)-methanone (Example 108)

{4-Amino-2-[4-(4-pyrrolidin-1-yl-piperidin-1-yl)-phenylamino]-thiazol-5-yl}-tolyl-methanone (Example 109)

{4-Amino-2-[4-(4-dimethylamino-piperidin-1-yl)-phenylamino]-thiazol-5-yl}-tolyl-methanone (Example 110)

[4-Amino-2-(4-[1,4']bipiperidinyl-1'-yl-phenylamino)-thiazol-5-yl]-tolyl-methanone (Example 111)

{4-Amino-2-[4-(4-morpholin-4-yl-piperidin-1-yl)-phenylamino]-thiazol-5-yl}-tolyl-methanone, compound with hydrobromide (Example 112)

{4-Amino-2-[4-(4-dimethylamino-piperidin-1-yl)-phenylamino]-thiazol-5-yl}-(4-methoxy-3-nitro-phenyl)-methanone (Example 113)

{4-Amino-2-[4-(4-pyrrolidin-1-yl-piperidin-1-yl)-phenylamino]-thiazol-5-yl}-(3-ethyl-phenyl)-methanone (Example 114)

{4-Amino-2-[4-(4-dimethylamino-piperidin-1-yl)-phenylamino]-thiazol-5-yl}-(3-ethyl-phenyl)-methanone (Example 115)

{4-Amino-2-[4-(4-morpholin-4-yl-piperidin-1-yl)-phenylamino]-thiazol-5-yl}-(3-ethyl-phenyl)-methanone (Example 116)

[4-Amino-2-(4-[1,4']bipiperidinyl-1'-yl-phenylamino)-thiazol-5-yl]-(3-ethyl-phenyl)-methanone (Example 117)

{4-Amino-2-[4-(4-pyrrolidin-1-yl-piperidin-1-yl)-phenylamino]-thiazol-5-yl}-(3-ethoxy-phenyl)-methanone (Example 118)

{4-Amino-2-[4-(4-pyrrolidin-1-yl-piperidin-1-yl)-phenylamino]-thiazol-5-yl}-(3-cyclopropul-phenyl)-methanone (Example 119)

{4-Amino-2-[4-(4-dimethylamino-piperidin-1-yl)-phenylamino]-thiazol-5-yl}-(3-cyclopropyl-phenyl)-methanone (Example 120)

{4-Amino-2-[4-(4-pyrrolidin-1-yl-piperidin-1-yl)-phenylamino]-thiazol-5-yl}-(3-fluoro-4-methyl-phenyl)-methanone (Example 121)
{4-Amino-2-[4-(4-pyrrolidin-1-yl-piperidin-1-yl)-phenylamino]-thiazol-5-yl}-(3-ethyl-4-fluoro-phenyl)-methanone (Example 122)
{4-Amino-2-[4-(4-pyrrolidin-1-yl-piperidin-1-yl)-phenylamino]-thiazol-5-yl}-(4-hydroxy-3-propyl-phenyl)-methanone (Example 123)
6-(4-Amino-2-{4-[ethyl-(3-pyrrolidin-1-yl-propyl)-amino]-phenylamino}-thiazole-5-carbonyl)-1-H-indole-2-carboxylic acid ethyl ester (Example 124)
{4-Amino-2-[4-(3-ethylamino-pyrrolidin-1-yl)-phenylamino]-thiazol-5-yl}-(3-fluoro-phenyl)-methanone (Example 132)
{4-Amino-2-[4-(3-ethylamino-pyrrolidin-1-yl)-phenylamino]-thiazol-5-yl}-(3-fluoro-4-methoxy-phenyl)-methanone (Example 133)
{4-Amino-2-[4-(3-ethylamino-pyrrolidin-1-yl)-phenylamino]-thiazol-5-yl}-(3-methoxy-phenyl)-methanone (Example 134)
{4-Amino-2-[4-(4-ethylamino-piperidin-1-yl)-phenylamino]-thiazol-5-yl}-(3-methoxy-phenyl)-methanone (Example 135)
{4-Amino-2-[4-(4-ethylamino-piperidin-1-yl)-phenylamino]-thiazol-5-yl}-(3-fluoro-4-methoxy-phenyl)-methanone (Example 136)
{4-Amino-2-[4-(4-ethylamino-piperidin-1-yl)-phenylamino]-thiazol-5-yl}-(3-fluoro-phenyl)-methanone (Example 137)

Preferred compounds of Formula (1) include:
{2-Amino-5-[4-(4-pyrrolidin-1-yl-piperidin-1-yl)-phenylamino]-4H-pyrrol-3-yl-}-(3-fluoro-4-methoxy-phenyl)-methanone (Example 23)
{4-Amino-2-[4-(4-pyrrolidin-1-yl-piperidin-1-yl)-phenylamino]-thiazol-5-yl}-(2,3-dihydro-benzo[1,4]dioxin-6-yl)-methanone (Example 26)
[4-Amino-2-(4-[1,4']bipiperidinyl-1'-yl-phenylamino)-thiazol-5-yl]-(3-fluoro-phenyl)-methanone (Example 30)
[4-Amino-2-(4-[1,4']bipiperid inyl-1'-yl-phenylamino)-thiazol-5-yl]-(2,3-dihydro-benzo[1,4]dioxin-6-yl)-methanone (Example 33)
[4-Amino-2-(4-[1,4']bipiperid inyl-1'-yl-phenylamino)-thiazol-5-yl]-(3-methoxy-phenyl)-methanone (Example 34)
{4-Amino-2-[4-(3-hydroxy-[1,4']bipiperidinyl-1'-yl)-phenylamino]-thiazol-5-yl}-(3-fluoro-4-methoxy-phenyl)-methanone (Example 36)
{4-Amino-2-[4-(4-dimethylamino-piperidin-1-yl)-phenylamino]-thiazol-5-yl}-benzo[1,3]dioxol-5-yl-methanone (Example 43)
{4-Amino-2-[4-(4-dimethylamino-piperidin-1-yl)-phenylamino]-thiazol-5-yl}-(3-methoxy-phenyl)-methanone (Example 45)
{4-Amino-2-[4-(4-dimethylamino-piperidin-1-yl)-phenylamino]-thiazol-5-yl}-(3-hydroxy-phenyl)-methanone (Example 50)
{4-Amino-2-[4-(4-pyrrolidin-1-yl-piperidin-1-yl)-phenylamino]-thiazol-5-yl}-(3-nitro-phenyl)-methanone (Example 90)
{4-Amino-2-[4-(3-hydroxy-[1,4']bipiperidinyl-1'-yl)-phenylamino]-thiazol-5-yl}-(3-nitro-phenyl)-methanone (Example 91)
[4-Amino-2-(4-[1,4']bipiperid inyl-1'-yl-phenylamino)-thiazol-5-yl]-(3-ethyl-phenyl)-methanone (Example 117)
{4-Amino-2-[4-(3-ethylamino-pyrrolidin-1-yl)-phenylamino]-thiazol-5-yl}-(3-fluoro-phenyl)-methanone (Example 132)

The compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formula above.

General Synthesis of Compounds According to the Invention

The compounds of the present invention can be prepared by any conventional means. Suitable processes for synthesizing these compounds are provided in the examples. Generally, compounds of formula I can be prepared according to one of the below described synthetic routes.

A. Ring Formation

Compounds of the invention can be prepared by the alkylation and cyclization of a number of thiourea derivatives, as shown in Scheme I, using reactions that are known. Among the thiourea derivatives that can be used are nitroamidinothioureas (Binu, R. et al. Org. Prep. Proced. Int. 1998, 30, 93–96); 1-[(arylthiocarbamoyl)amino]-3,5-dimethylpyrazoles (Jenardanan, G. C. et al. Synth. Commun. 1997, 27, 3457–3462); and N-(aminoiminomethyl)-N'-phenylthioureas (Rajasekharan, K. N. et al. Synthesis 1986, 353–355).

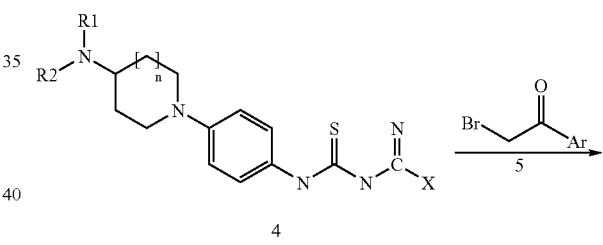

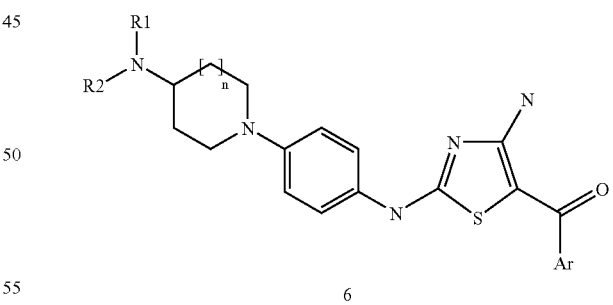

Another thiourea derivative that can be used for the preparation of compounds of the invention by alkylation and cyclization is N-cyanothiourea (Gewald, K. et al. J. Prakt. Chem. 1967, 97–104). For example, pursuant to Scheme IA below, an N-cyanothiourea of formula 4A can be reacted with a halomethylketone, such as a bromomethylketone of formula 5, at a temperature between around room temperature and around 65° C., to yield a compound of formula 6.

Scheme IA
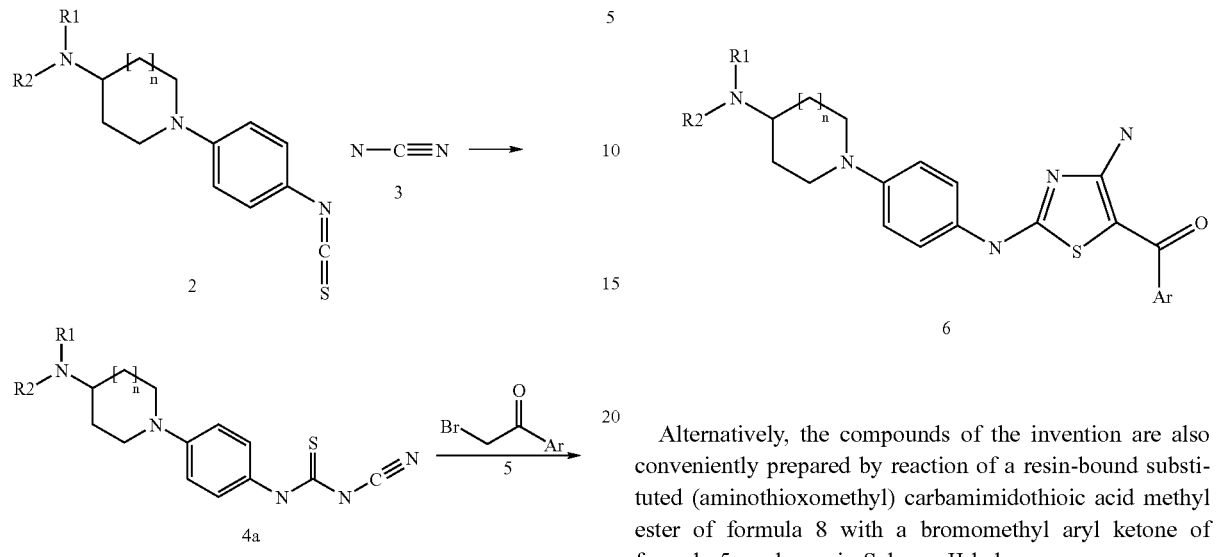
Alternatively, the compounds of the invention are also conveniently prepared by reaction of a resin-bound substituted (aminothioxomethyl) carbamimidothioic acid methyl ester of formula 8 with a bromomethyl aryl ketone of formula 5 as shown in Scheme II below.
Scheme II
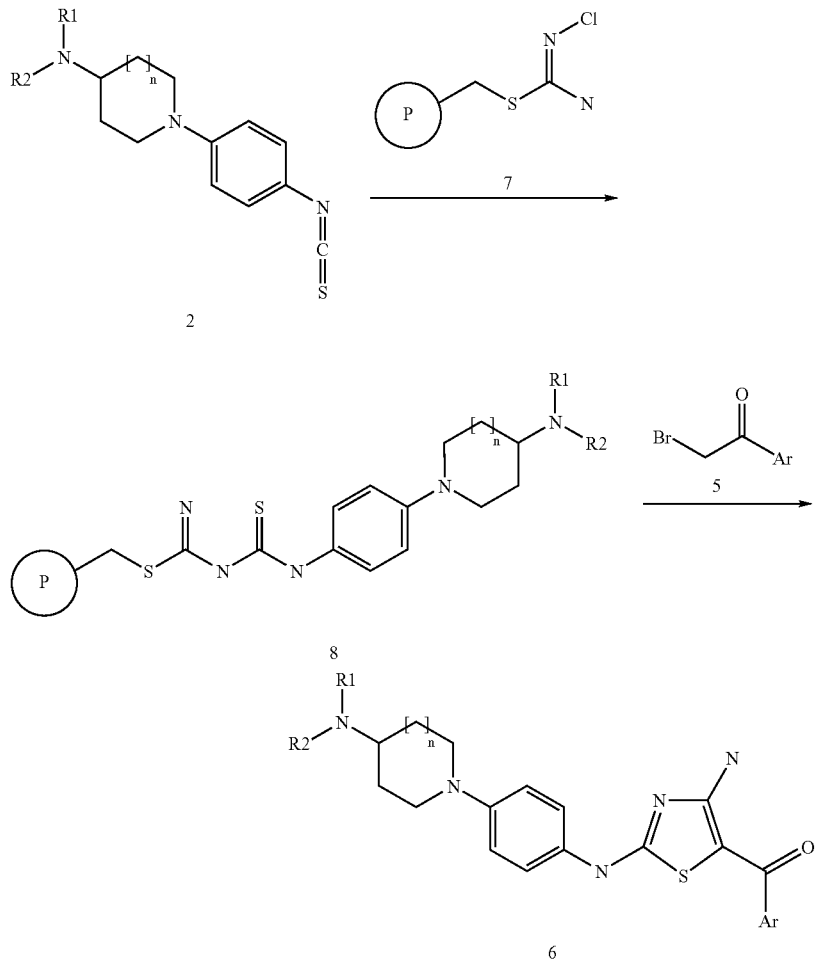

The resin-bound thiourea derivative of formula 8 can be made by any conventional procedure known to one skilled in the art of organic synthesis. For example, it can be conveniently prepared by the reaction of a resin-bound thiouronium salt of formula 7 with an isothiocyanate of formula 2 in the presence of a base, such as a tertiary amine (e.g., triethylamine or diisopropylethylamine) in an inert solvent, such as a polar aprotic solvent (e.g., N,N-dimethylformamide). The reaction is conveniently carried out around room temperature. The resin-bound thiourea derivative of formula 8 is then converted to the product of formula 6 by treatment with a halomethylketone (for example, a bromomethylketone of formula 5) in a suitable inert solvent such as a polar aprotic solvent (e.g., N,N-dimethylformamide) at around room temperature.

B. Separating a Mixture of Stereoisomers into the Optically Pure Stereoisomers (When Compound of Formula I is Chiral)

The optional separation of isomeric structures of formula I can be carried out according to known methods such as for example resolution or chiral high pressure liquid chromatography (also known as chiral HPLC). Resolution methods are well known, and are summarized in "Enantiomers, Racemates, and Resolutions" (Jacques, J. et al. John Wiley and Sons, NY, 1981). Methods for chiral HPLC are also well known, and are summarized in "Separation of Enantiomers by Liquid Chromatographic Methods" (Pirkle, W. H. and Finn, J. in "Asymmetric Synthesis", Vol. 1, Morrison, J. D., Ed., Academic Press, Inc., NY 1983, pp. 87–124).

C. Converting a Compound of Formula I that Bears a Basic Nitrogen into a Pharmaceutically Acceptable Acid Addition Salt The optional conversion of a compound of formula I that bears a basic nitrogen into a pharmaceutically acceptable acid addition salt can be effected by conventional means. For example, the compound can be treated with an inorganic acid such as for example hydrochloric acid, hydrobromic acid, sulfuric acid, nitric acid, phosphoric acid, or with an appropriate organic acid such as acetic acid, citric acid, tartaric acid, methanesulfonic acid, p-toluenesulfonic acid, or the like.

D. Converting a Compound of Formula I that Bears a Carboxylic Acid Group into a Pharmaceutically Acceptable Alkali Metal Salt The optional conversion of a compound of formula I that bears a carboxylic acid group into a pharmaceutically acceptable alkali metal salt can be effected by conventional means. For example, the compound can be treated with an inorganic base such as lithium hydroxide, sodium hydroxide, potassium hydroxide, or the like.

E. Converting a Compound of Formula I that Bears a Carboxylic Acid Group into a Pharmaceutically Acceptable Ester The optional conversion of a compound of formula I that bears a carboxylic acid group into a pharmaceutically acceptable ester can be effected by conventional means. The conditions for the formation of the ester will depend on the stability of the other functional groups in the molecule to the reaction conditions. If the other moieties in the molecule are stable to acidic conditions, the ester may be conveniently prepared by heating in a solution of a mineral acid (e.g., sulfuric acid) in an alcohol. Other methods of preparing the ester, which may be convenient if the molecule is not stable to acidic conditions include treating the compound with an alcohol in the presence of a coupling agent and in the optional presence of additional agents that may accelerate the reaction. Many such coupling agents are known to one skilled in the art of organic chemistry. Two examples are dicyclohexylcarbodiimide and triphenylphosphine/diethyl azodicarboxylate. In the case where dicyclohexylcarbodiimide is used as the coupling agent, the reaction is conveniently carried out by treating the acid with the alcohol, dicyclohexylcarbodiimide, and the optional presence of a catalytic amount (0–10 mole %) of N,N-dimethylaminopyridine, in an inert solvent such as a halogenated hydrocarbon (e.g., dichloromethane) at a temperature between about 0° C. and about room temperature, preferably at about room temperature. In the case where triphenylphosphine/diethyl azodicarboxylate is used as the coupling agent, the reaction is conveniently carried out by treating the acid with the alcohol, triphenylphosphine and diethyl azodicarboxylate, in an inert solvent such as an ether (e.g., tetrahydrofuran) or an aromatic hydrocarbon (e.g., benzene) at a temperature between about 0° C. and about room temperature, preferably at about 0° C.

The isothiocyanate intermediates of formula 2, used to make compounds of the invention, can be made by any conventional means. For example, they may be made by the route shown in Scheme V below.

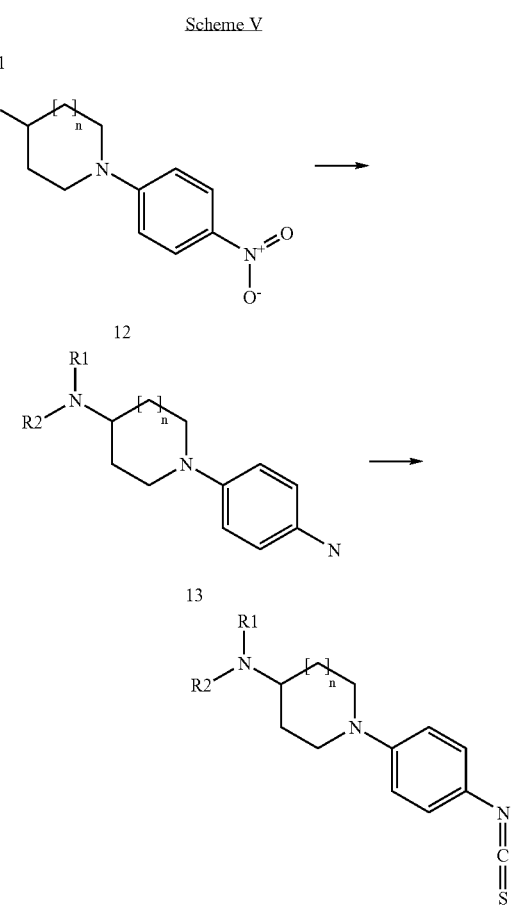

The nitro group in a compound of formula 12 can be reduced to give an aniline of formula 13 using a number of methods familiar to one skilled in the art. These methods include (1) treatment of the nitro compound of formula 12 with iron/acetic acid, with tin(II) chloride/hydrochloric acid, or with zinc and ammonium chloride; and (2) hydrogenation in the presence of a noble metal catalyst such as palladium-on-carbon.

The isothiocyanates of formula 2 may be made from anilines of formula 13 using any one of a number of reagents known to those skilled in organic synthesis to be useful for the transformation of an aniline of formula 13 into an isothiocyanate of formula 2. Among these reagents are carbon disulfide, thiophosgene, 1,1'-thiocarbonylbis(2-pyridone), and thiocarbonyl diimidazole. The reaction can be carried out by treating an aniline of formula 13 with thiocarbonyl diimidazole in a suitable inert solvent such as a polar aprotic solvent (e.g., N,N-dimethylformamide) at a temperature between about −20° C. and about 0° C., preferably at about −15° C.

Nitro compounds of formula 12 can be made by a variety of methods that are known in the field of organic synthesis. For example, they may be made by the nucleophilic substitution of a nitrobenzene derivative that bears a leaving group at the position para to the nitro group in accordance with Scheme VI below:

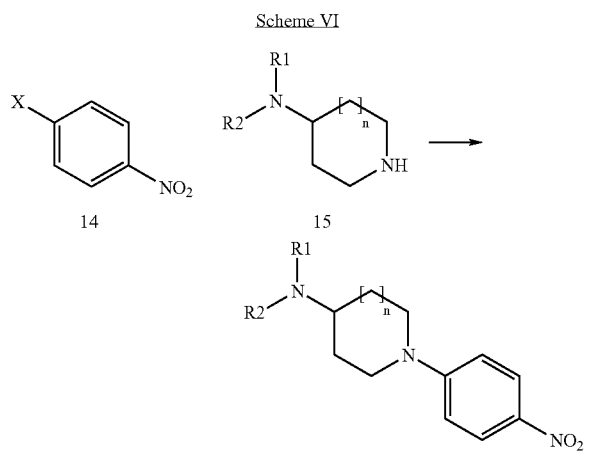

The nucleophilic substitution reaction between an amine of formula 15 and a nitrobenzene of formula 14 (wherein X is a leaving group) to give the substituted product of formula 12 can be conveniently carried out by heating these materials together at a temperature between about 50 and about 100° C., preferably at about 80° C., in the optional presence of an inert solvent such as acetonitrile (Scheme VI). Suitable leaving groups of formula X include chloride and fluoride.

Bromomethylketone intermediates 5 used to make compounds of the invention are available commercially or can be made using one of a number of methods known to those skilled in the art of organic synthesis, for example: Friedel-Crafts reactions of an arene with bromoacetyl bromide or bromoacetyl chloride; oxidation of a 2-bromo-1-phenethyl alcohol; reaction of a diazomethyl ketone with HBr; reduction of a dibromomethyl ketone (see Scheme VIII) below; or reaction of a methyl ketone with a brominating agent (see Scheme IX) such as bromine, copper(II) bromide, tetrabutylammonium tribromide, or 5,5-dibromobarbituric acid.

According to the method of Diwu et al. (Tetrahedron Lett. 1998, 39, 4987–4990), methyl ketones of formula 19 can be converted into the corresponding dibromomethyl ketones of formula 20 by treatment with bromine in neat sulfuric acid. The dibromomethyl ketones of formula 20 can then be converted into the desired bromomethyl ketones of formula 5 by reduction with diethylphosphite.

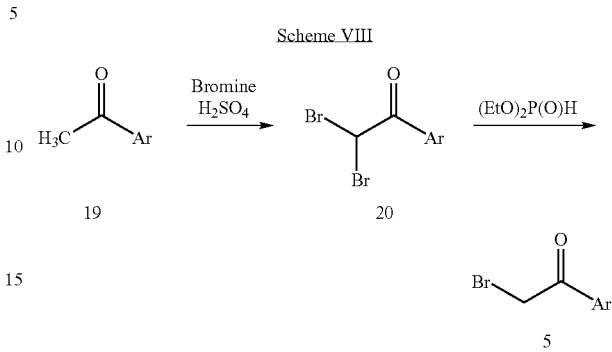

Bromomethyl ketones of formula 5 can also be prepared directly from methyl ketones of formula 19 using a variety of reagents well known to those of ordinary skill in the art of organic synthesis, such as those mentioned above. For example, the reaction may be conveniently carried out by treating the methyl ketone of formula 19 with bromine in a suitable inert solvent such as a halogenated hydrocarbon (e.g., carbon tetrachloride) in the optional presence of other agents that facilitate the reaction, such as a Bronsted or Lewis acid catalyst (e.g., aluminum chloride or acetic acid). The optimal reaction temperature depends on whether or not a catalyst is used. In the case where aluminum chloride is used, the reaction is conveniently carried out at about 0° C. In the cases where acetic acid is added, or where no catalyst is used, the reaction is conveniently carried out at a temperature between about room temperature and about 80° C., preferably at about room temperature. Alternatively, a methyl ketone of formula 19 may be converted to a bromomethylketone of formula 5 by treatment with copper (II) bromide in a suitable unreactive solvent such as ethyl acetate, preferably at the reflux temperature.

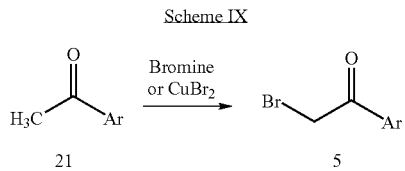

Compositions/Formulations

In an alternative embodiment, the present invention is directed to pharmaceutical compositions comprising at least one compound of formula I, or a pharmaceutically acceptable salt or ester thereof.

These pharmaceutical compositions can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, and/or the salts or esters thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerin, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

Dosages

As mentioned above, the compounds of the present invention are useful in the treatment or control of cell proliferative disorders, in particular oncological disorders. These compounds and formulations containing the compounds are particularly useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

EXAMPLES

The following examples illustrate preferred methods for synthesizing the compounds and formulations of the present invention.

Example 1

Dimethyl-[1-(4-nitro-phenyl)-piperidin-4-yl]-amine

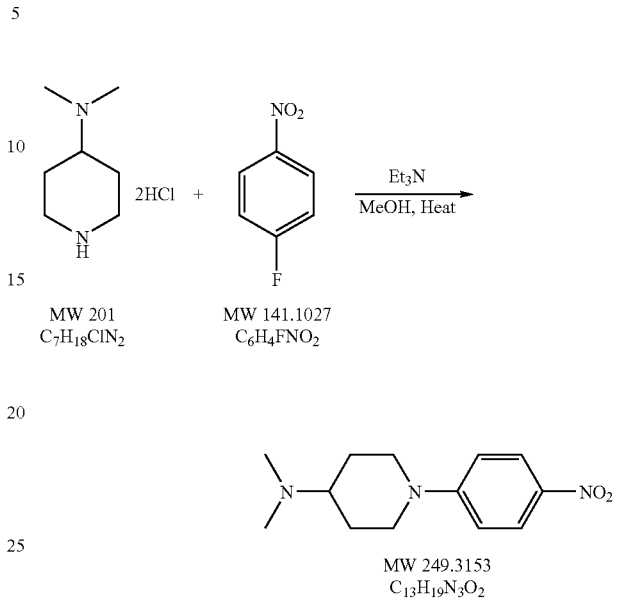

Dimethyl-piperidin-4-yl-amine dihydrochloride (Aldrich, 2.0 g, 9.95 mmol) and 4-fluoro-nitrobenzene (Aldrich, 2.5 g, 17.7 mmol) were added to methanol (30 mL). The mixture was heated to 90° C. and stirred for 3.5 hours. The mixture was treated with 1 N HCl to pH=1 and then extracted with diethyl ether (2×10 mL). The aqueous layer was treated with saturated sodium carbonate to pH=10 and then extracted with methylene chloride (2×20 mL). The organic layer was dried with sodium sulfate and the solvent was removed to give the desired product. 1.25 g, 50%. MS (m+H)$^+$: 250.

Example 2

Dimethyl-[1-(4-nitro-phenyl)-piperidin-4-yl]-amine

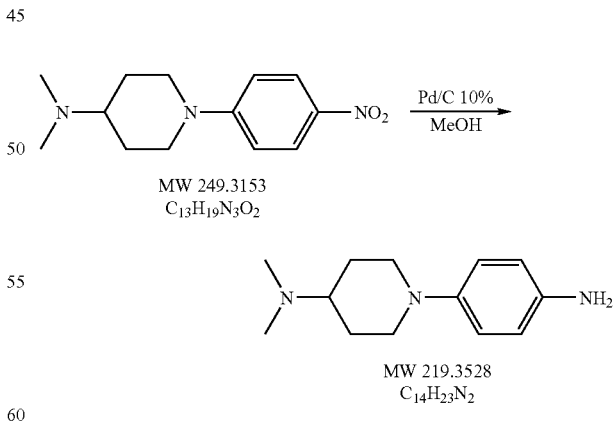

Dimethyl-[1-(4-nitro-phenyl)-piperidin-4-yl]-amine (Example 1, 1.25 g, 5.02 mmol) was dissolved in methanol. Pd/C (10%, Aldrich, 250 mg) was added and the mixture was hydrogenated under 30 psi for 2 hours and filtered through a pad of ceilite to give a clear solution. Removal of solvent gave a brown solid. 1.18 g, 97%. MS (m+H)$^+$: 220.

Example 3

[1-(4-Isothiocyanato-phenyl)-piperidin-4-yl]-dimethyl-amine

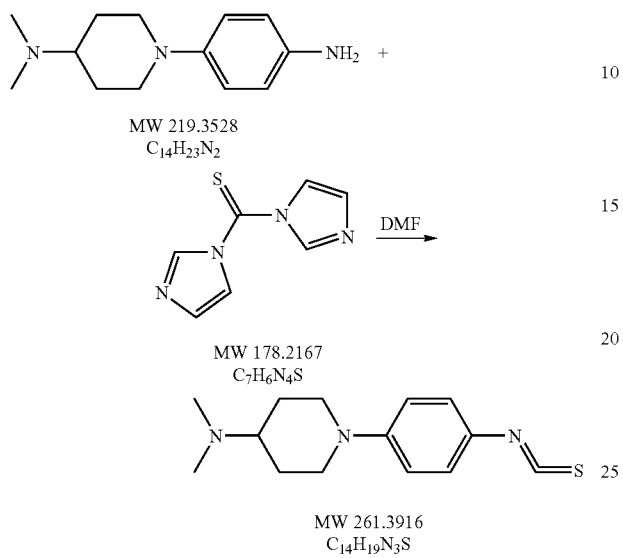

Dimethyl-[1-(4-nitro-phenyl)-piperidin-4-yl]-amine (Example 2, 1.1 g, 5.0 mmol) was dissolved in DMF (5 mL). To the stirred solution, thiocarbonyl diimidazole (Aldrich, 1.18 g, 90%, 6 mmol) was added and the solution was stirred at room temperature for 80 minutes. The mixture was poured into water and extracted with diethyl ether. The extract was dried with sodium sulfate and concentrated to give a pale yellow solid. 1.12 g, 85%. MS (m+H)$^+$: 262.

Example 4

4-Piperidin-4-yl-morpholine

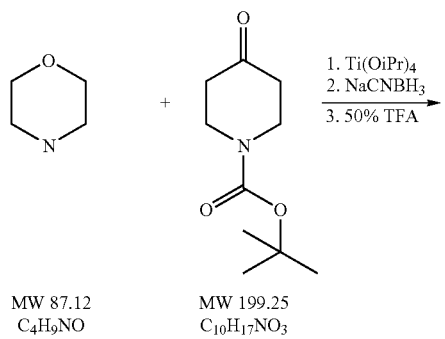

To a stirred solution of 4-oxo-piperidine-1-carboxylic acid tert-butyl ester (Aldrich, 3.0 g, 15 mmol) in THF (25 mL), morpholine (Aldrich, 1.56 g, 18 mmol) and Ti(OiPr)4 (Aldrich, 5.58 mL) were added successively and the mixture was stirred at room temperature for 1 hour. Then, 15 mL of ethanol was added and followed by sodium cyanoborohydride (0.63 g, 10.05 mmol). The resulting mixture was stirred at room temperature over night and the reaction was quenched with addition of water (4 mL). The mixture was stirred for 30 minutes and the white solid was filtered out and the filtrate was evaporated. The residue was partitioned between ether and water and the organic layer was separated and dried with sodium sulfate. Removal of solvent gave a white solid which was treated with 40 mL of 50% TFA in methylene chloride. The solution was stirred at room temperature for 1 hour and the solvent was removed. The residue was lyophilized to give a white solid. 5.48 g, 98%. MS (m+H)$^+$: 171.

Example 5

4-[1-(4-Nitro-phenyl)-piperidin-4-yl]-morpholine

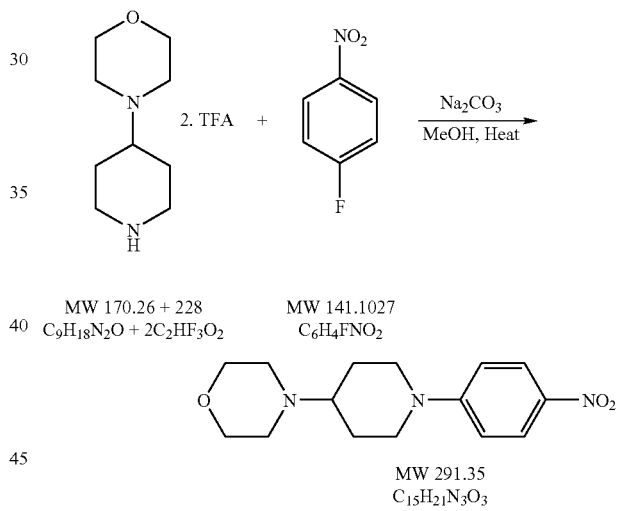

The compound was prepared from 4-piperidin-4-yl-morpholine (Example 4) and 4-fluoro-nitrobenzene (Aldrich) following the procedure used in Example 1. MS (m+H)$^+$: 292.

Example 6

4-(4-Morpholin-4-yl-piperidin-1-yl)-phenylamine

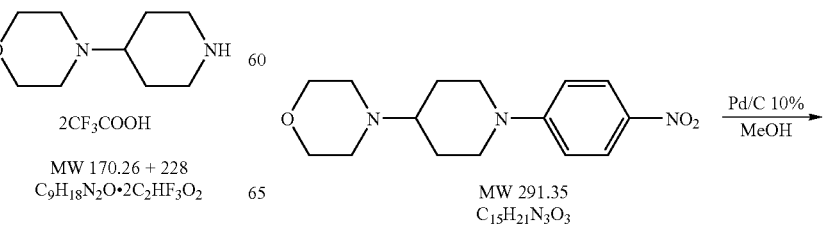

-continued

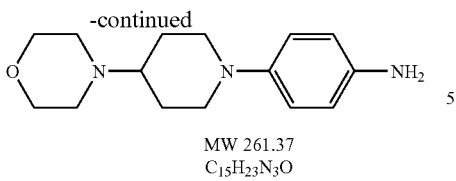

MW 261.37
C₁₅H₂₃N₃O

The compound was prepared from 4-[1-(4-Nitro-phenyl)-piperidin-4-yl]-morpholine (Example 5) following the procedure used in Example 2. MS (m+H)⁺: 262.

Example 7

4-[1-(4-Isothiocyanato-phenyl)-piperidin-4-yl]-morpholine

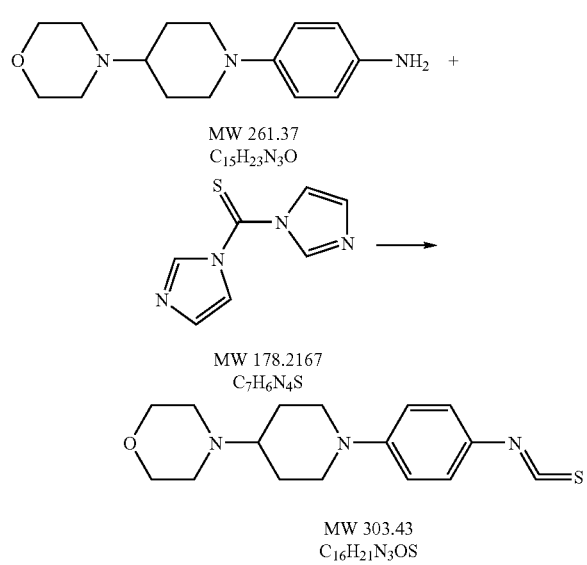

The compound was prepared from 4-(4-morpholin-4-yl-piperidin-1-yl)-phenylamine (Example 6) following the procedure used in Example 3. MS (m+H)⁺: 304.

Example 8

1'-(4-Nitro-phenyl)-[1,4']bipiperidinyl

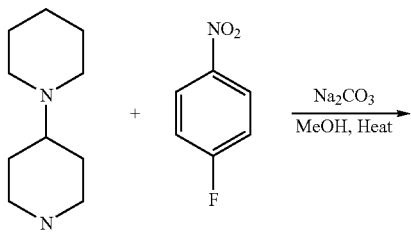

MW 168.28
C₁₀H₂₀N₂

MW 141.1027
C₆H₄FNO₂

-continued

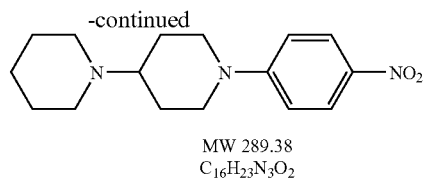

MW 289.38
C₁₆H₂₃N₃O₂

The compound was prepared from 4-piperidin-4-yl-piperidine (Aldrich) and 4-fluoro-nitrobenzene (Aldrich) following the procedure used in Example 1. MS (m+H)⁺: 290.

Example 9

4-[1,4']Bipiperidinyl-1'-yl-phenylamine

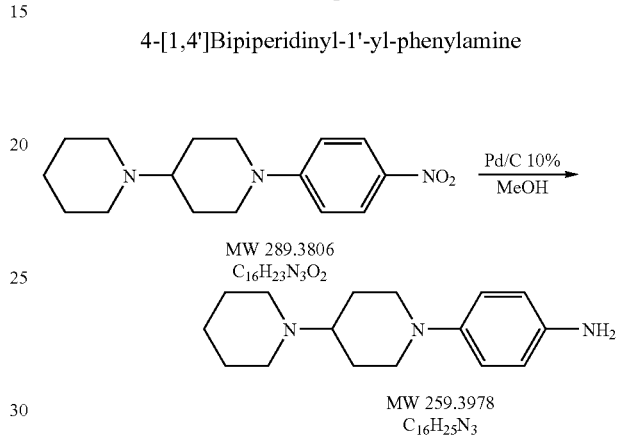

The compound was prepared from 1'-(4-nitro-phenyl)-[1,4']bipiperidinyl (Example 8) following the procedure used in Example 2. MS (m+H)⁺: 260.

Example 10

1'-(4-Isothiocyanato-phenyl)-[1,4']bipiperidinyl

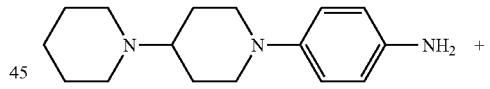

The compound was prepared from dimethyl-[1-(4-nitro-phenyl)-piperidin-4-yl]-amine (Example 9) following the procedure used in Example 3. MS (m+H)⁺: 302.

Example 11

1-(4-Nitro-phenyl)-4-pyrrolidin-1-yl-piperidine

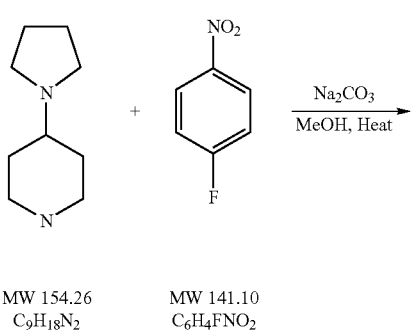

The compound was prepared from 4-pyrrolidin-1-yl-piperidine (Aldrich) and 4-fluoro-nitrobenzene (Aldrich) following the procedure used in Example 1. MS (m+H)+: 276.

Example 12

4-(4-Pyrrolidin-1-yl-piperidin-1-yl)-phenylamine

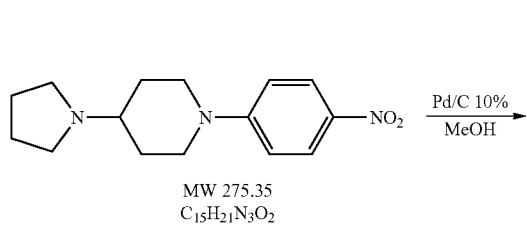

The compound was prepared from 1-(4-nitro-phenyl)-4-pyrrolidin-1-yl-piperidine (Example 11) following the procedure used in Example 2. MS (m+H)+: 246.

Example 13

1'-(4-Isothiocyanato-phenyl)-[1,4']bipiperidinyl

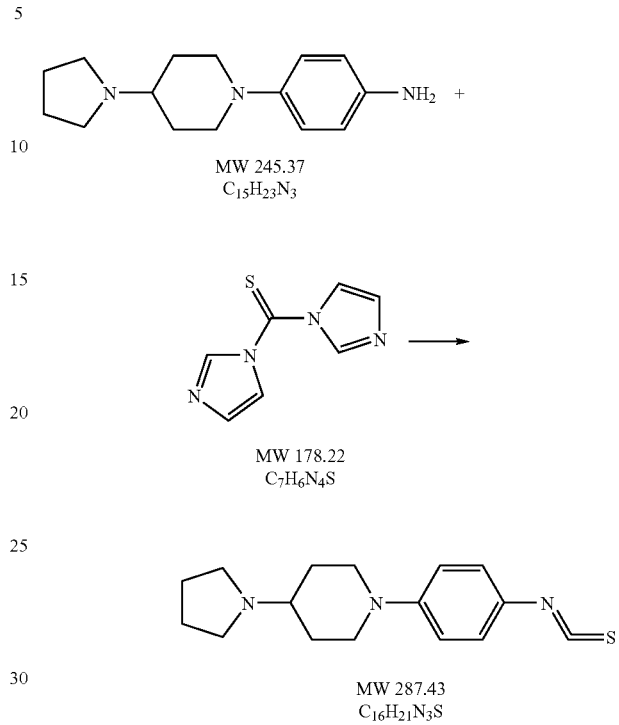

The compound was prepared from 4-(4-pyrrolidin-1-yl-piperidin-1-yl)-phenylamine (Example 12) following the procedure used in Example 3. MS (m+H)+: 288.

Example 14

1'-(4-Nitro-phenyl)-[1,4']bipiperidinyl-3-ol

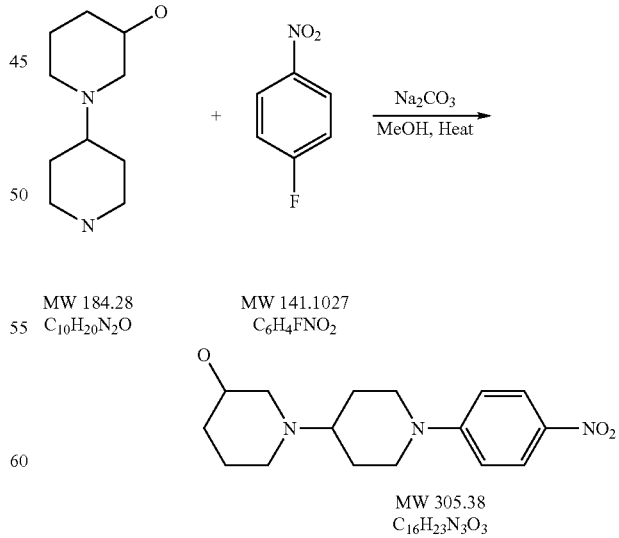

The compound was prepared from [1,4']bipiperidinyl-3-ol (ChemBridge) and 4-fluoro-nitrobenzene (Aldrich) following the procedure used in Example 1. MS (m+H)+: 306.

Example 15

1'-(4-Amino-phenyl)-[1,4']bipiperidinyl-3-ol

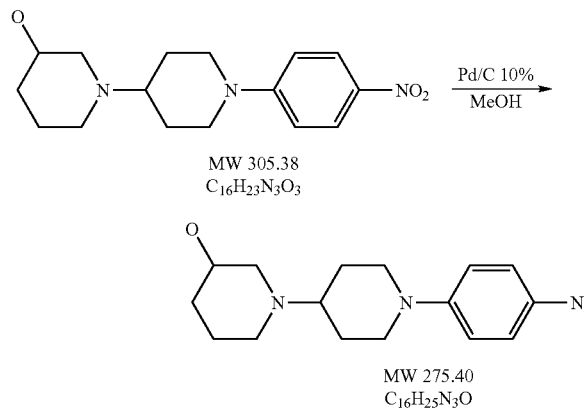

The compound was prepared from 1'-(4-nitro-phenyl)-[1,4']bipiperidinyl-3-ol (Example 14) following the procedure used in Example 2. MS (m+H)$^+$: 276.

Example 16

1'-(4-Isothiocyanato-phenyl)-[1,4']bipiperidinyl-3-ol

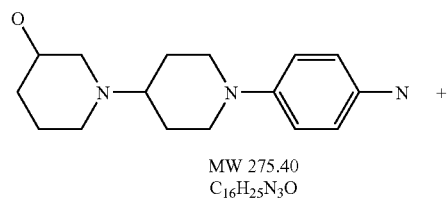

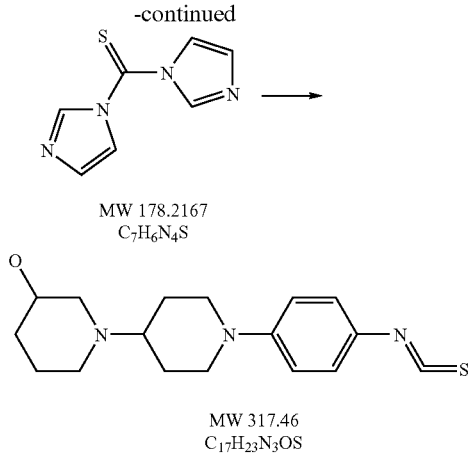

The compound was prepared from 1'-(4-amino-phenyl)-[1,4']bipiperidinyl-3-ol (Example 15) following the procedure used in Example 3. MS (m+H)$^+$: 318.

Example 17

Resin-bound Thiourea: General Procedure

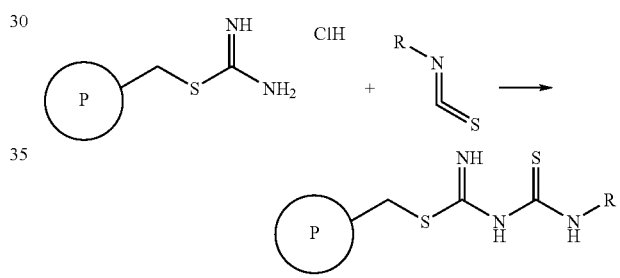

Following the procedure of Chu et al. (WO 2003097048), the resin-bound thiourea was made.

The following resin-bound thioureas were prepared from indicated isothiocyanates using the general procedure described in Example 17.

| Starting materials: Isothiocyanate | Products: Resin-bound thioureas |
|---|---|
| 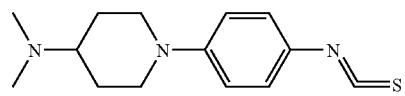 <br> Example 3 | 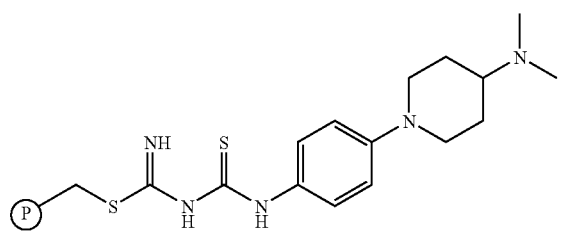 <br> Example 18 |

| Starting materials: Isothiocyanate | Products: Resin-bound thioureas |
|---|---|
| 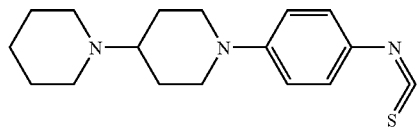
Example 10 | 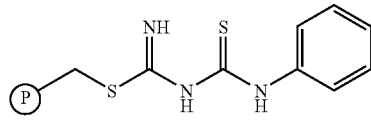
Example 19 |
| 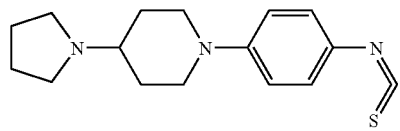
Example 13 | 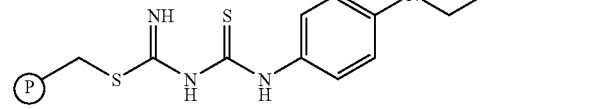
Example 20 |
| 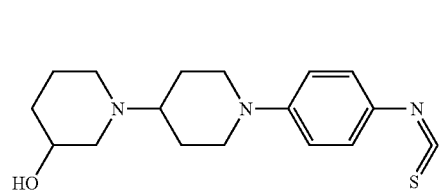
Example 16 | 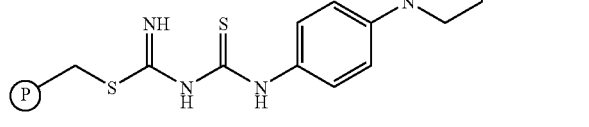
Example 21 |
| 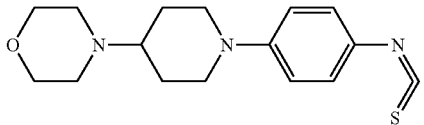
Example 7 | 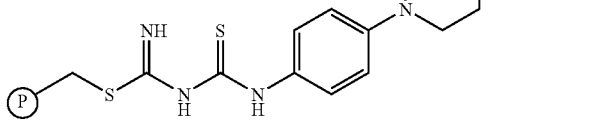
Example 22 |

Example 23

{2-Amino-5-[4-(4-pyrrolidin-1-yl-piperidin-1-yl)-phenylamino]-4H-pyrrol-3-yl}-(3-fluoro-4-methoxy-phenyl)-methanone

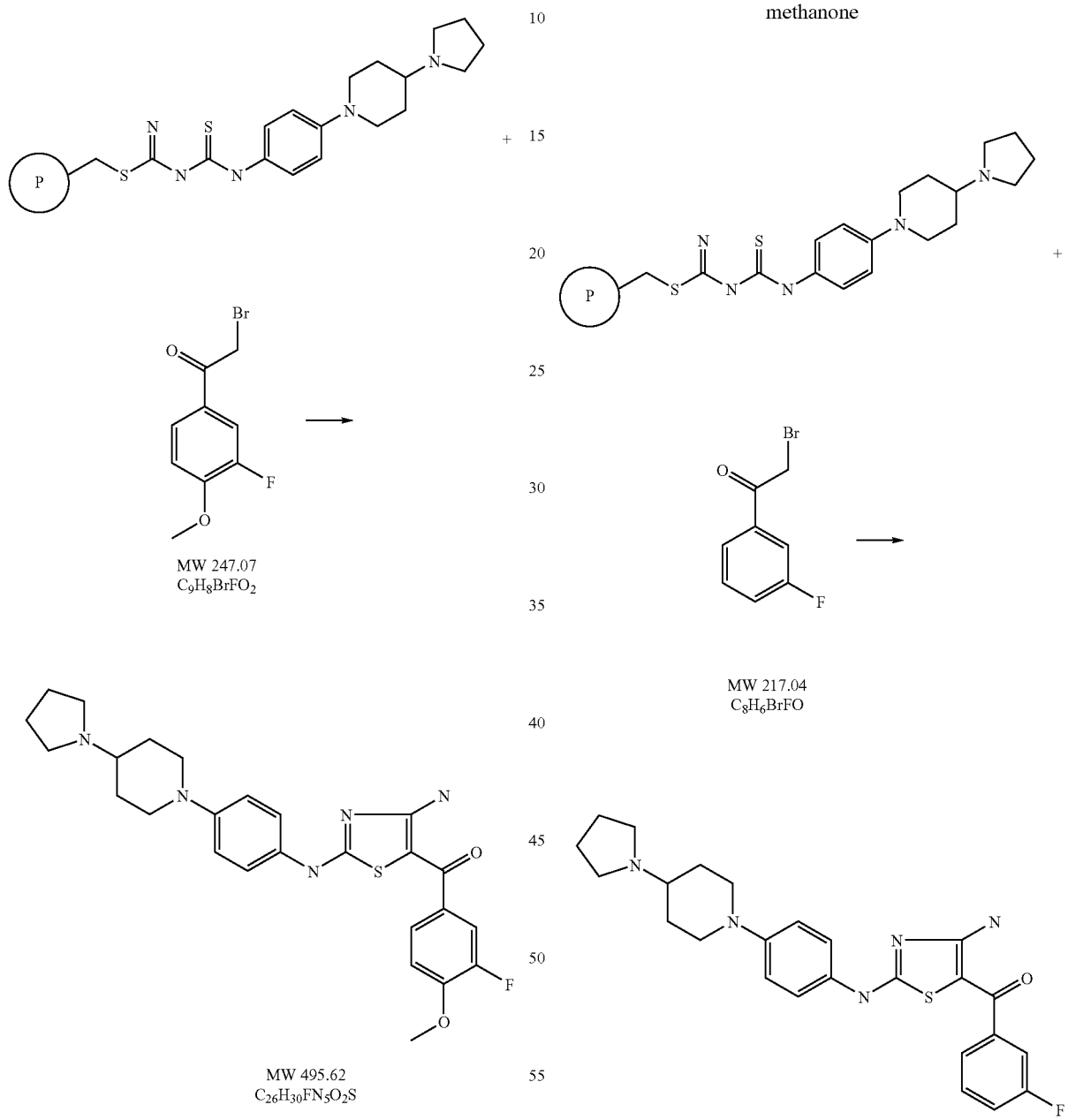

MW 247.07
C$_9$H$_8$BrFO$_2$

MW 495.62
C$_{26}$H$_{30}$FN$_5$O$_2$S

The resin-bound thiourea of Example 20 (65 mg, 0.1 mmol, 1.6 mmol/g) was suspended in DMF (5 mL). To the shaking suspension, 1'-bromo-3-fluoro-4-methoxy acetophenone (Chu et al. WO2003097048; 49 mg, 0.2 mmol) was added and the mixture was shaken over a shaker overnight at room temperature. Polymer bounded trisamine (Argonaut Technologies) was added and the mixture was shaken for 3.5 hours and filtered. The filtrate was concentrated under reduced pressure to give the crude which was purified by reverse phase HPLC to yield a pale yellow solid. 20.4 mg, 43%. MS (m+H)$^+$: 496.

Example 24

{4-Amino-2-[4-(4-pyrrolidin-1-yl-piperidin-1-yl)-phenylamino]-thiazol-5-yl}-(3-fluoro-phenyl)-methanone MW 217.04
C$_8$H$_6$BrFO

MW 465.60
C$_{23}$H$_{28}$FN$_5$OS

The compound was prepared from 3-fluorophenylacyl bromide (Maybridge International) and the resin-bound thiourea of Example 20 following the procedure used in Example 23. MS (m+H)$^+$: 466.

Example 25

{4-Amino-2-[4-(4-pyrrolidin-1-yl-piperidin-1-yl)-phenylamino]-thiazol-5-yl}-benzo[1,3]dioxol-5-yl-methanone

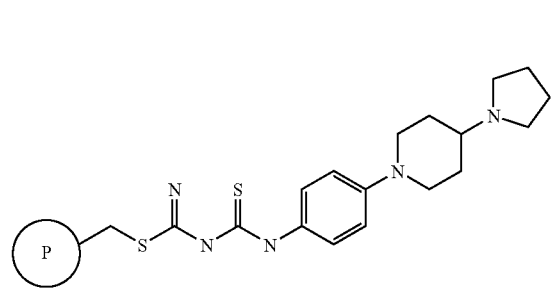

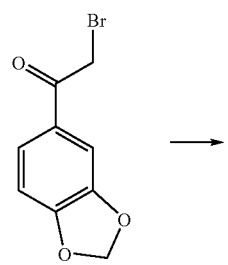

MW 243.06
C$_9$H$_7$BrO$_3$

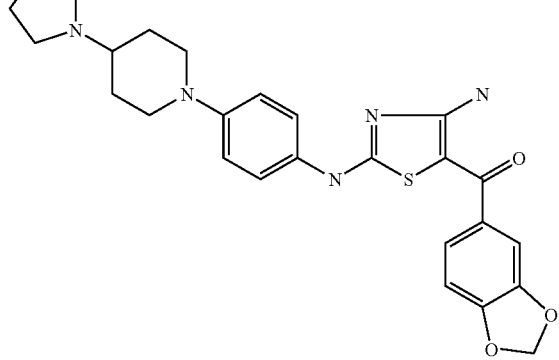

MW 491.62
C$_{26}$H$_{29}$N$_5$O$_3$S

The compound was prepared from 1-benzo[1,3]dioxol-5-yl-2-bromo-ethanone (Maybridge International) and the resin-bound thiourea of Example 20 following the procedure used in Example 23. MS (m+H)$^+$: 492.

Example 26

{4-Amino-2-[4-(4-pyrrolidin-1-yl-piperidin-1-yl)-phenylamino]-thiazol-5-yl}-(2,3-dihydro-benzo[1,4]dioxin-6-yl)-methanone

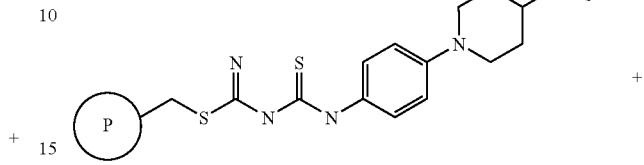

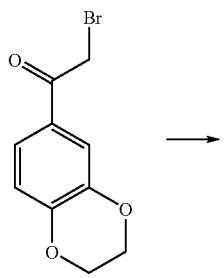

MW 257.09
C$_{10}$H$_9$BrO$_3$

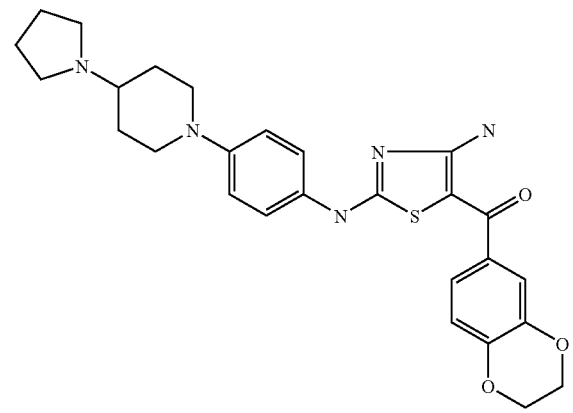

MW 505.64
C$_{23}$H$_{31}$N$_5$O$_3$S

The compound was prepared from 2-bromo-1-(2,3-dihydro-benzo[1,4]dioxin-6-yl)-ethanone (Maybridge International) and the resin-bound thiourea of Example 20 following the procedure used in Example 23. MS (m+H)$^+$: 506.

Example 27

{{4-Amino-2-[4-(4-pyrrolidin-1-yl-piperidin-1-yl)-phenylamino]-thiazol-5-yl}-(3-methoxy-phenyl)-methanone

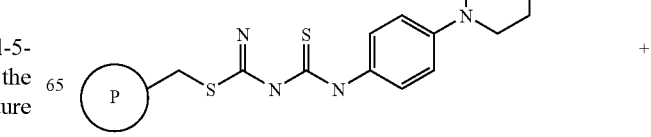

-continued

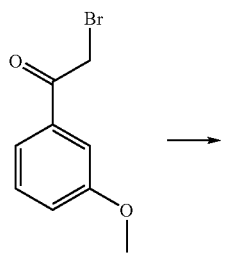

MW 229.07
C9H9BrO2

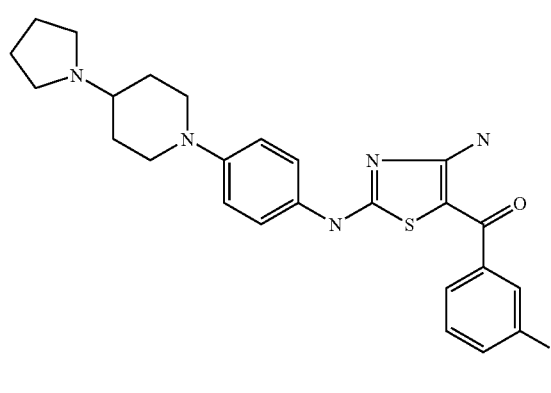

MW477.63
C26H31N5O2S

The compound was prepared from 2-bromo-1-(3-methoxy-phenyl)-ethanone (Maybridge International) and the resin-bound thiourea of Example 20 following the procedure used in Example 23. MS (m+H)+: 478.

Example 28

{4-Amino-2-[4-(4-pyrrolidin-1-yl-piperidin-1-yl)-phenylamino]-thiazol-5-yl}-(4-hydroxy-phenyl)-methanone -continued

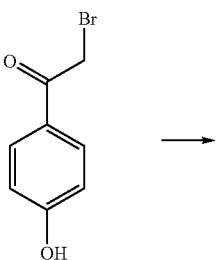

MW 215.05
C8H7BrO2

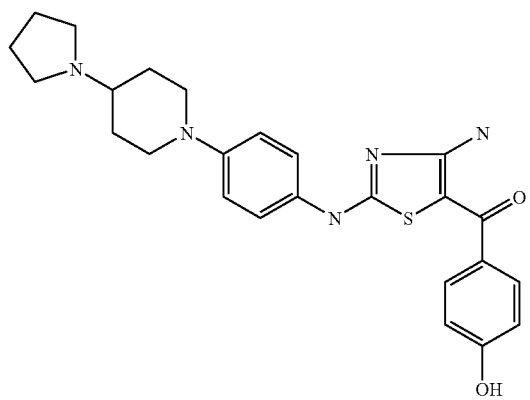

MW 463.61
C25H29N5O2S

The compound was prepared from 2-bromo-1-(4-hydroxy-phenyl)-ethanone (ChonTech) and the resin-bound thiourea of Example 20 following the procedure used in Example 23. MS (m+H)+: 464.

Example 29

[4-Amino-2-(4-[1,4']bipiperidinyl-1'-yl-phenylamino)-thiazol-5-yl]-(4-hydroxy-phenyl)-methanone

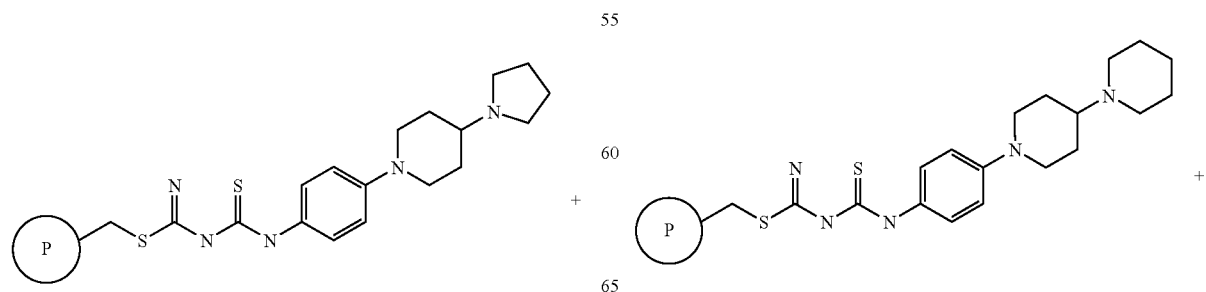

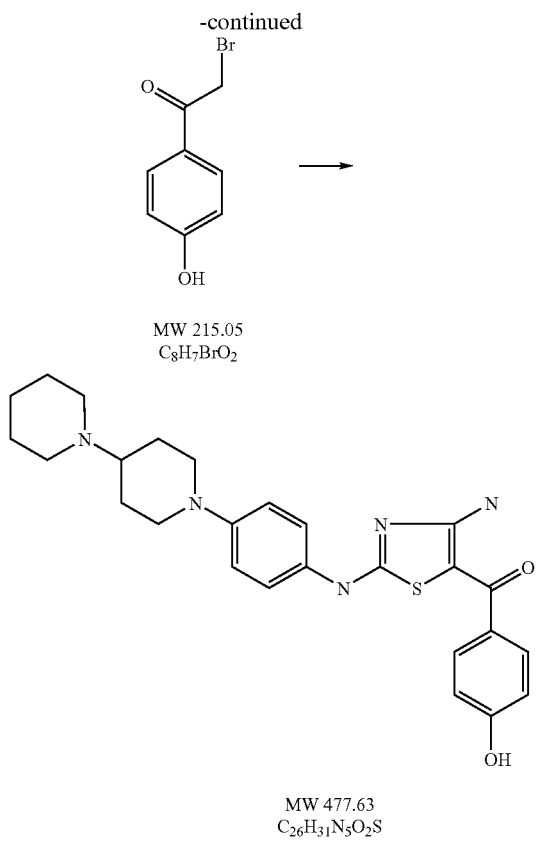

The compound was prepared from 2-bromo-1-(4-hydroxy-phenyl)-ethanone (ChonTech) and the resin-bound thiourea of Example 19 following the procedure used in Example 23. MS (m+H)⁺: 478.

Example 30

[4-Amino-2-(4-[1,4']bipiperidinyl-1'-yl-phenylamino)-thiazol-5-yl]-(3-fluoro-phenyl)-methanone

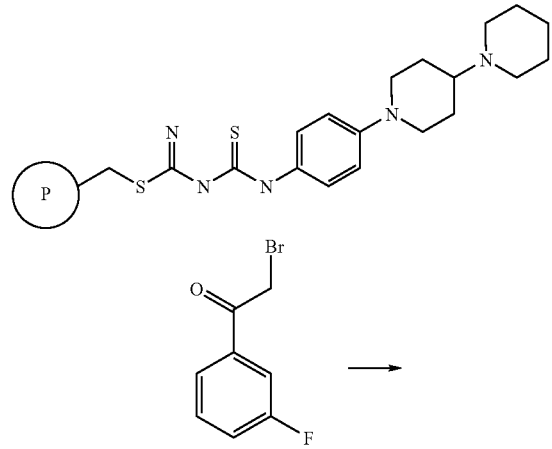

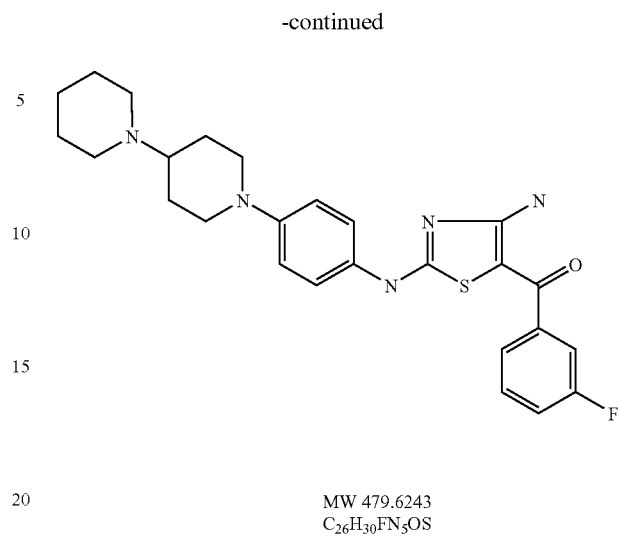

The compound was prepared from 3-fluorophenylacyl bromide (Maybridge International) and the resin-bound thiourea of Example 19 following the procedure used in Example 23. MS (m+H)⁺: 480.

Example 31

[4-Amino-2-(4-[1,4']bipiperidinyl-1'-yl-phenylamino)-thiazol-5-yl]-(3-fluoro-4-methoxy-phenyl)-methanone

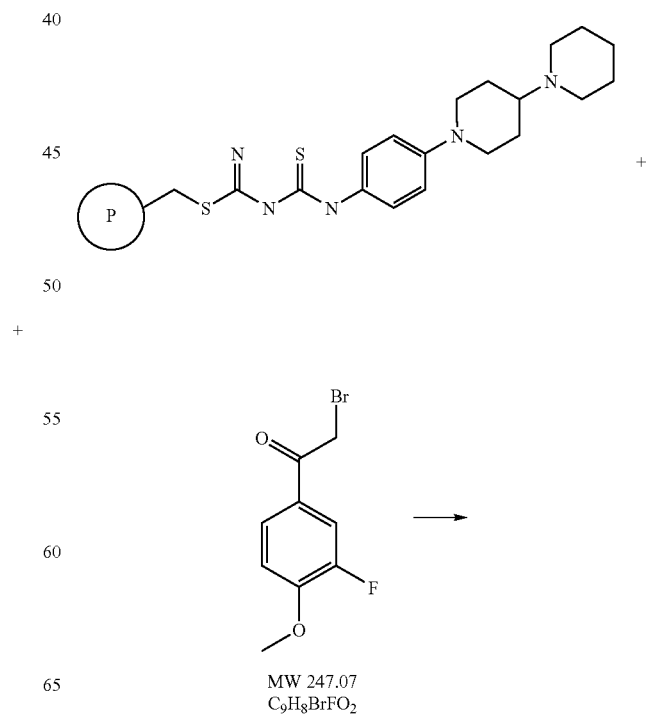

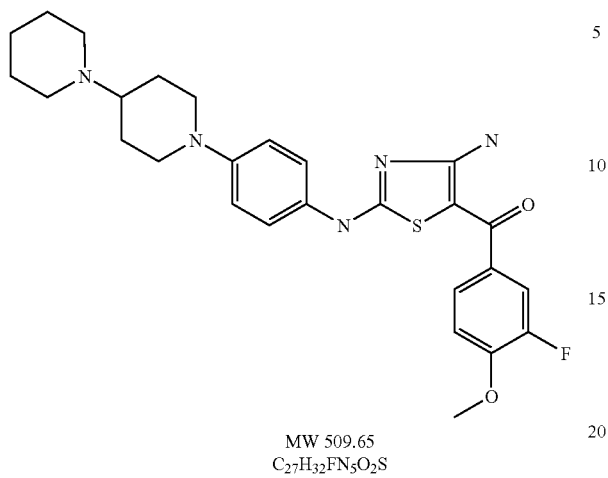

MW 509.65
C$_{27}$H$_{32}$FN$_5$O$_2$S

MW 505.64
C$_{27}$H$_{31}$N$_5$O$_3$S

The compound was prepared from 1'-bromo-3-fluoro-4-methoxy acetophenone (Chu et al. WO2003097048) and the resin-bound thiourea of Example 19 following the procedure used in Example 23. MS (m+H)$^+$: 510.

The compound was prepared from 1-benzo[1,3]dioxol-5-yl-2-bromo-ethanone (Maybridge International) and the resin-bound thiourea of Example 19 following the procedure used in Example 23. MS (m+H)$^+$: 506.

Example 32

[4-Amino-2-(4-[1,4']bipiperidinyl-1'-yl-phenylamino)-thiazol-5-yl]-benzo[1,3]dioxol-5-yl-methanone Example 33

[4-Amino-2-(4-[1,4']bipiperidinyl-1'-yl-phenylamino)-thiazol-5-yl]-(2,3-dihydro-benzo[1,4]dioxin-6-yl)-methanone

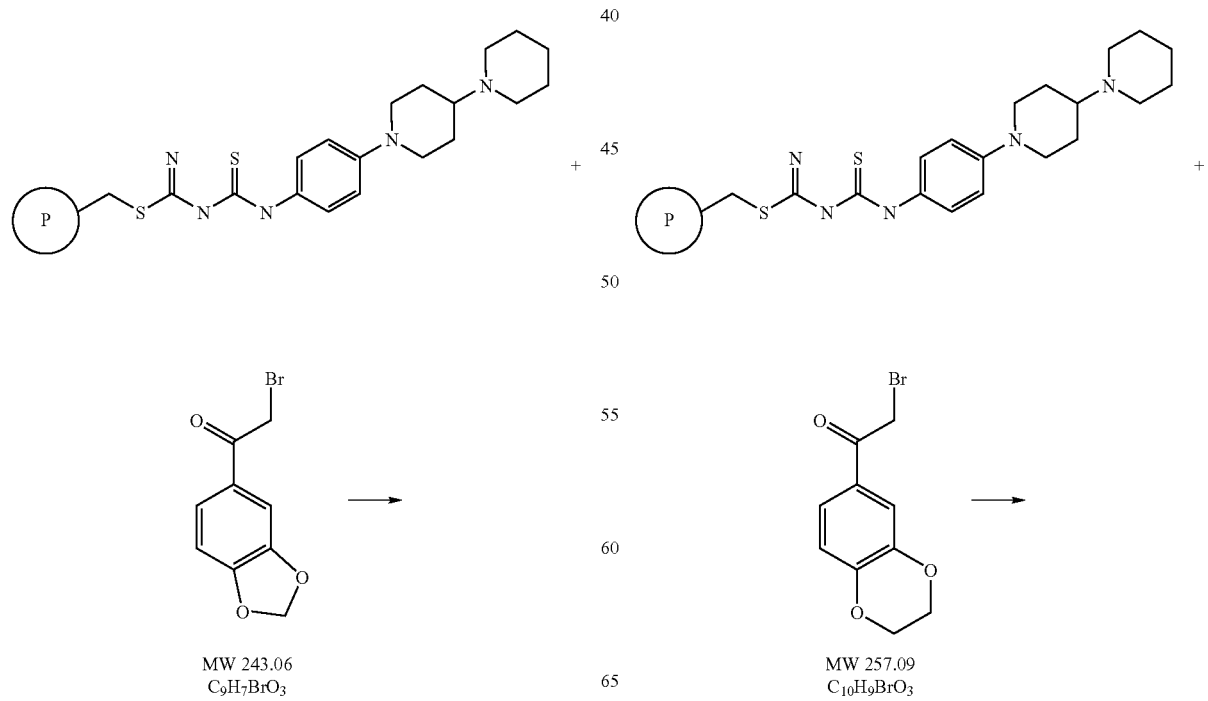

MW 243.06
C$_9$H$_7$BrO$_3$

MW 257.09
C$_{10}$H$_9$BrO$_3$

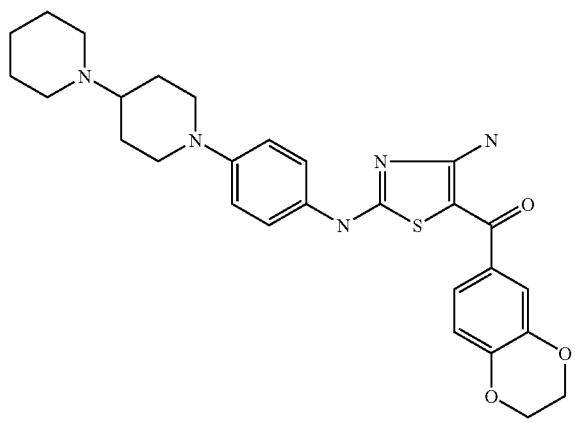

MW 519.67
C28H33N5O3S

The compound was prepared from 2-bromo-1-(2,3-dihydro-benzo[1,4]dioxin-6-yl)-ethanone (Maybridge International) and the resin-bound thiourea of Example 19 following the procedure used in Example 23. MS (m+H)+: 520.

Example 34

[4-Amino-2-(4-[1,4']bipiperidinyl-1'-yl-phenylamino)-thiazol-5-yl]-(3-methoxy-phenyl)-methanone

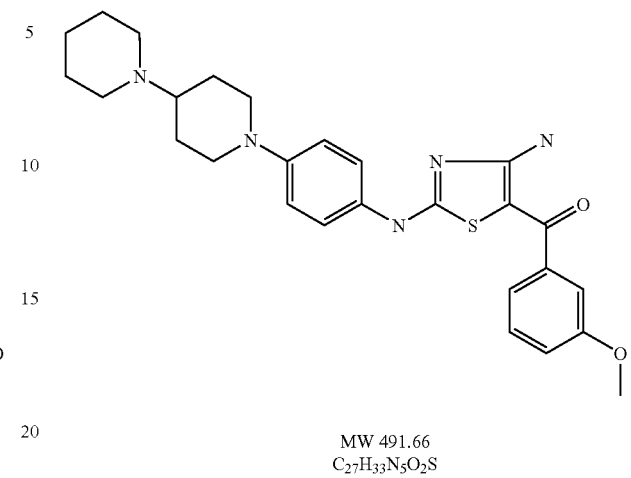

MW 491.66
C27H33N5O2S

The compound was prepared from 2-bromo-1-(3-methoxy-phenyl)-ethanone (Maybridge International) and the resin-bound thiourea of Example 19 following the procedure used in Example 23. MS (m+H)+: 492.

Example 35

{4-Amino-2-[4-(3-hydroxy-[1,4']bipiperidinyl-1'-yl)-phenylamino]-thiazol-5-yl}-(3-fluoro-phenyl)-methanone

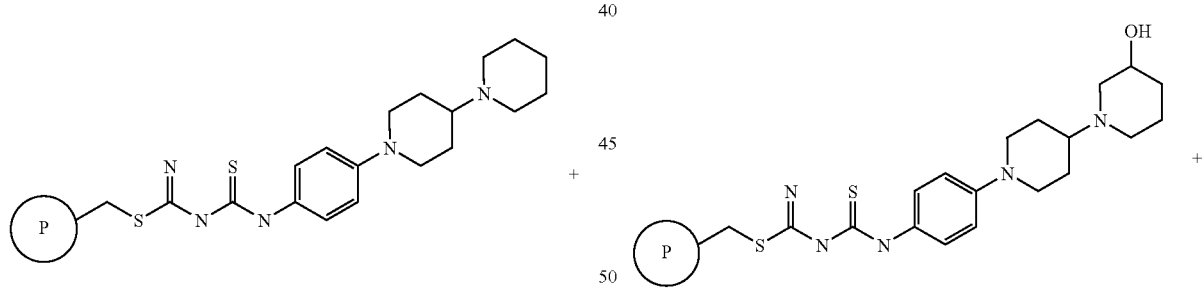

MW 229.07
C9H9BrO2

MW 217.04
C8H6BrFO

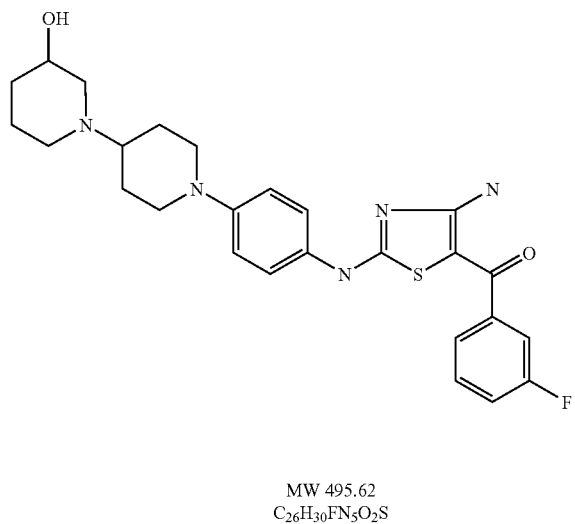

MW 495.62
C26H30FN5O2S

The compound was prepared from 3-fluorophenylacyl bromide (Maybridge International) and the resin-bound thiourea of Example 21 following the procedure used in Example 23. MS (m+H)+: 496.

Example 36

{4-Amino-2-[4-(3-hydroxy-[1,4']bipiperidinyl-1'-yl)-phenylamino]-thiazol-5-yl}-(3-fluoro-4-methoxy-phenyl)-methanone

MW 525.65
C27H32FN5O3S

The compound was prepared from 1'-bromo 3-fluoro-4-methoxy acetophenone (Chu et al. WO2003097048) and the resin-bound thiourea of Example 21 following the procedure used in Example 23. MS (m+H)+: 526.

Example 37

{4-Amino-2-[4-(3-hydroxy-[1,4']bipiperidinyl-1'-yl)-phenylamino]-thiazol-5-yl}-benzo[1,3]dioxol-5-yl-methanone

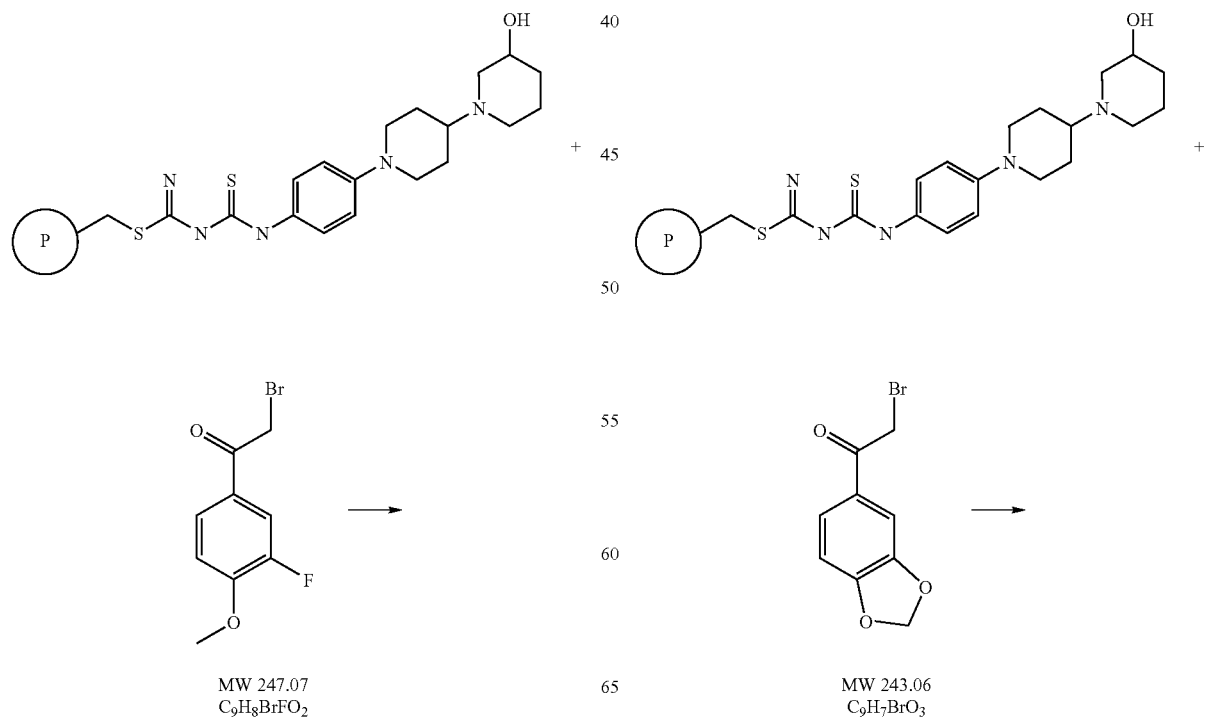

MW 247.07
C9H8BrFO2

MW 243.06
C9H7BrO3

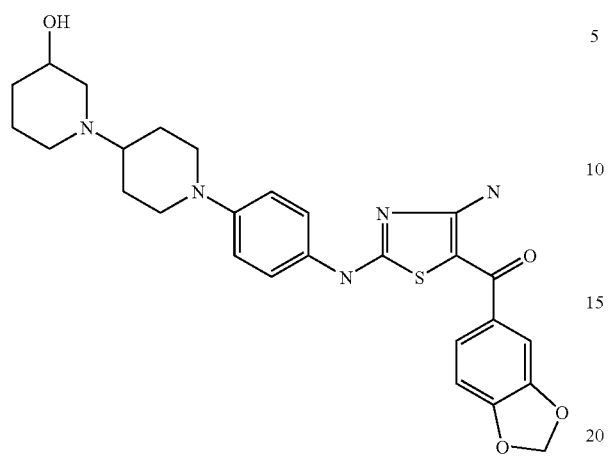

MW 521.64
$C_{27}H_{31}FN_5O_4S$

MW 521.66
$C_{28}H_{33}N_4O_4S$

The compound was prepared from 1-benzo[1,3]dioxol-5-yl-2-bromo-ethanone (Maybridge International) and the resin-bound thiourea of Example 21, following the procedure used in Example 23. MS (m+H)$^+$: 522.

The compound was prepared from 2-bromo-1-(2,3-dihydro-benzo[1,4]dioxin-6-yl)-ethanone (Maybridge International) and example 21 following the procedure used in Example 23. MS (m+H)$^+$: 522.

Example 38

{4-Amino-2-[4-(3-hydroxy-[1,4']bipiperidinyl-1'-yl)-phenylamino]-thiazol-5-yl}-(2,3-dihydro-benzo[1,4]dioxin-6-yl)-methanone Example 39

{4-Amino-2-[4-(3-hydroxy-[1,4']bipiperidinyl-1'-yl)-phenylamino]-thiazol-5-yl}-(2,3-dihydro-benzo[1,4]dioxin-6-yl)-methanone

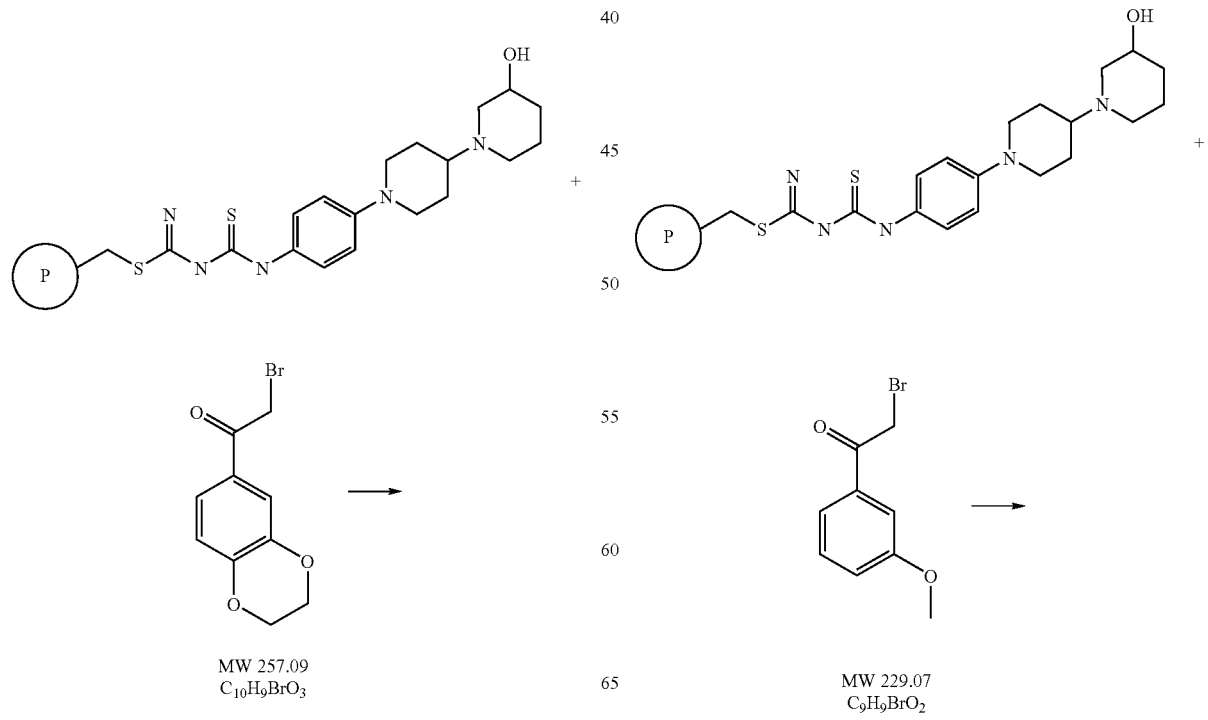

MW 257.09
$C_{10}H_9BrO_3$

MW 229.07
$C_9H_9BrO_2$

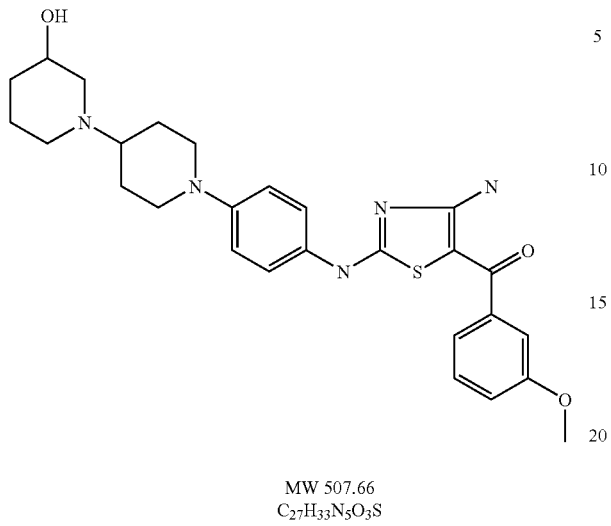

MW 507.66
C₂₇H₃₃N₅O₃S

The compound was prepared from 2-bromo-1-(3-methoxy-phenyl)-ethanone (Maybridge International) and the resin-bound thiourea of Example 21 following the procedure used in Example 23. MS (m+H)⁺: 508.

Example 40

{4-Amino-2-[4-(3-hydroxy-[1,4']bipiperidinyl-1'-yl)-phenylamino]-thiazol-5-yl}-(4-hydroxy-phenyl)-methanone

MW 493.63
C₂₆H₃₁N₅O₃S

The compound was prepared from 2-bromo-1-(4-hydroxy-phenyl)-ethanone (ChonTech) and the resin-bound thiourea of Example 21 following the procedure used in Example 23. MS (m+H)⁺: 494.

Example 41

{4-Amino-2-[4-(4-dimethylamino-piperidin-1-yl)-phenylamino]-thiazol-5-yl}-(3-fluoro-phenyl)-methanone

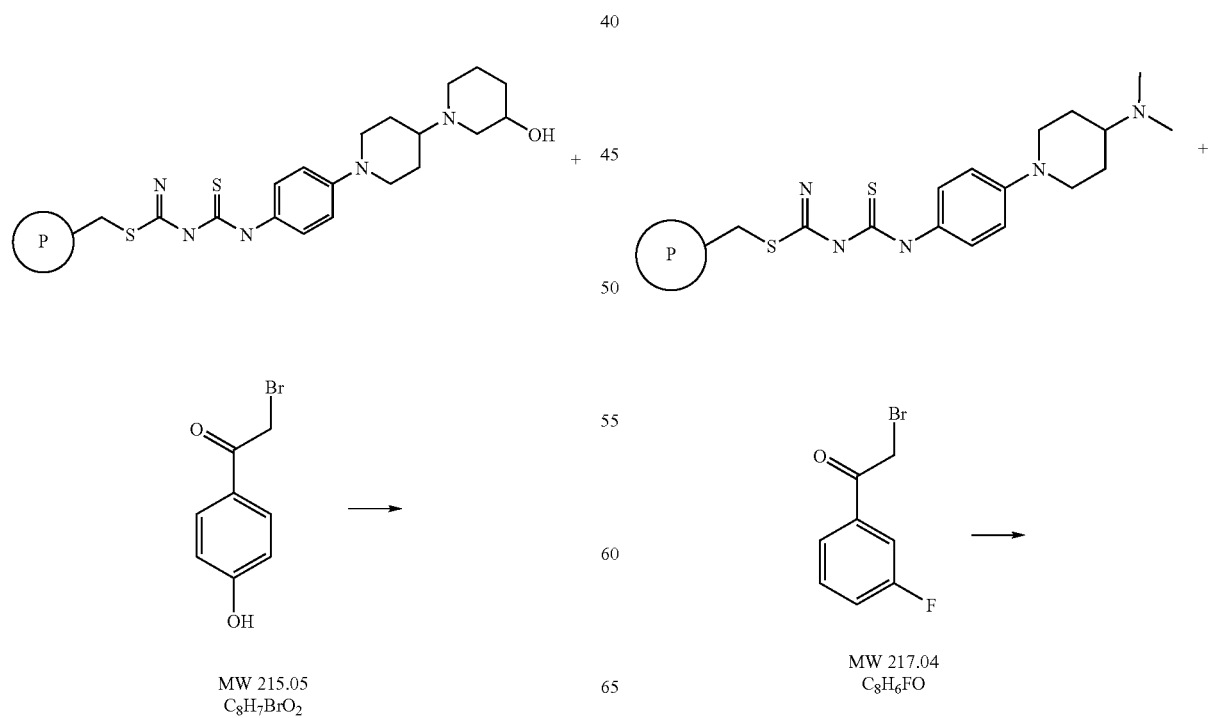

MW 215.05
C₈H₇BrO₂

MW 217.04
C₈H₆FO

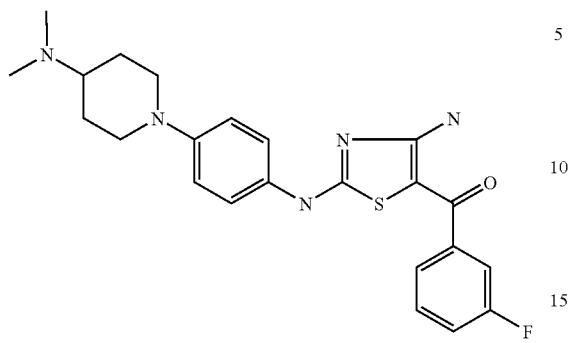

MW 493.56
$C_{23}H_{29}FN_5OS$

The compound was prepared from 3-fluorophenylacyl bromide (Maybridge International) and the resin-bound thiourea of Example 18 following the procedure used in Example 23. MS (m+H)$^+$: 440.

Example 42

{4-Amino-2-[4-(4-dimethylamino-piperidin-1-yl)-phenylamino]-thiazol-5-yl}-(3-fluoro-4-methoxy-phenyl)-methanone

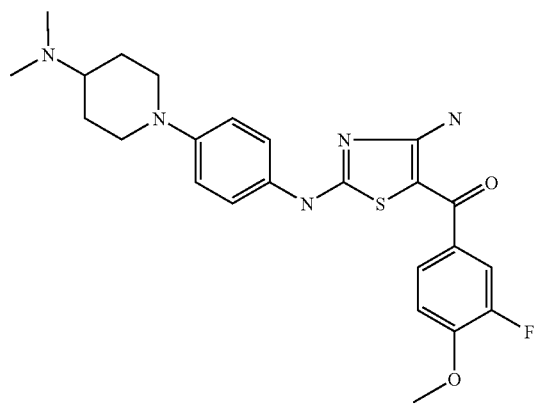

MW 469.59
$C_{24}H_{28}FN_5O_2S$

The compound was prepared from 1'-bromo 3-fluoro4-methoxy acetophenone (Chu et al. WO2003097048) and the resin-bound thiourea of Example 18 following the procedure used in Example 23. MS (m+H)$^+$: 470.

Example 43

{4-Amino-2-[4-(4-dimethylamino-piperidin-1-yl)-phenylamino]-thiazol-5-yl}-benzo[1,3]dioxol-5-yl-methanone

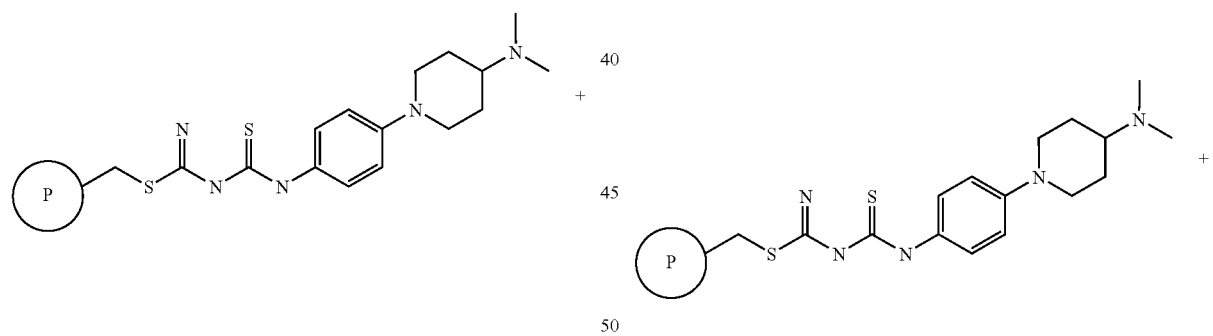

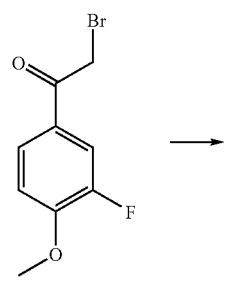

MW 247.07
$C_9H_6BrFO_2$

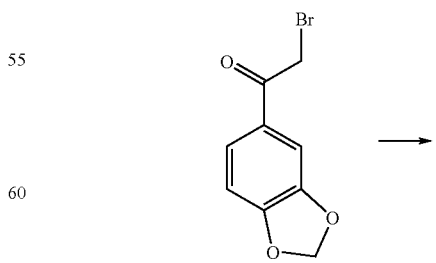

MW 243.06
$C_9H_7BrO_3$

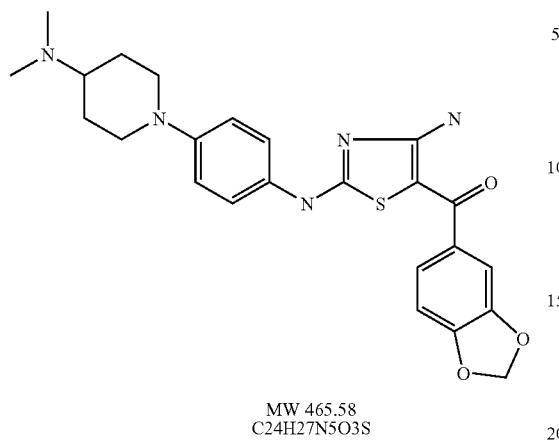

MW 465.58
C24H27N5O3S

The compound was prepared from 1-benzo[1,3]dioxol-5-yl-2-bromo-ethanone (Maybridge International) and the resin-bound thiourea of Example 18 following the procedure used in Example 23. MS (m+H)+: 466.

Example 44

{4-Amino-2-[4-(4-dimethylamino-piperidin-1-yl)-phenylamino]-thiazol-5-yl}-(2,3-dihydro-benzo[1,4]dioxin-6-yl)-methanone

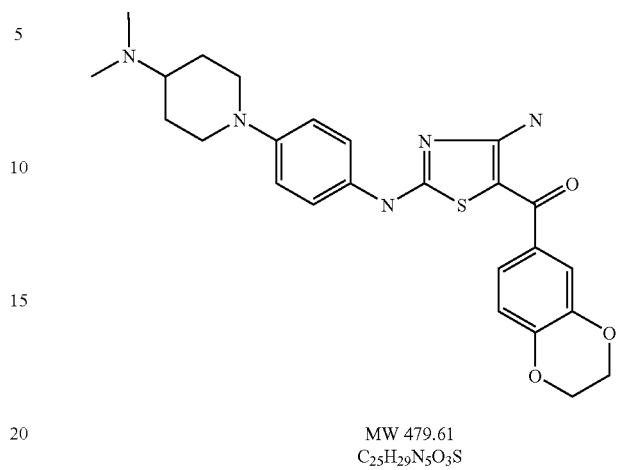

MW 479.61
C25H29N5O3S

The compound was prepared from 2-bromo-1-(2,3-dihydro-benzo[1,4]dioxin-6-yl)-ethanone (Maybridge International) and the resin-bound thiourea of Example 18 following the procedure used in Example 23. MS (m+H)+: 480.

Example 45

{4-Amino-2-[4-(4-dimethylamino-piperidin-1-yl)-phenylamino]-thiazol-5-yl}-(3-methoxy-phenyl)-methanone

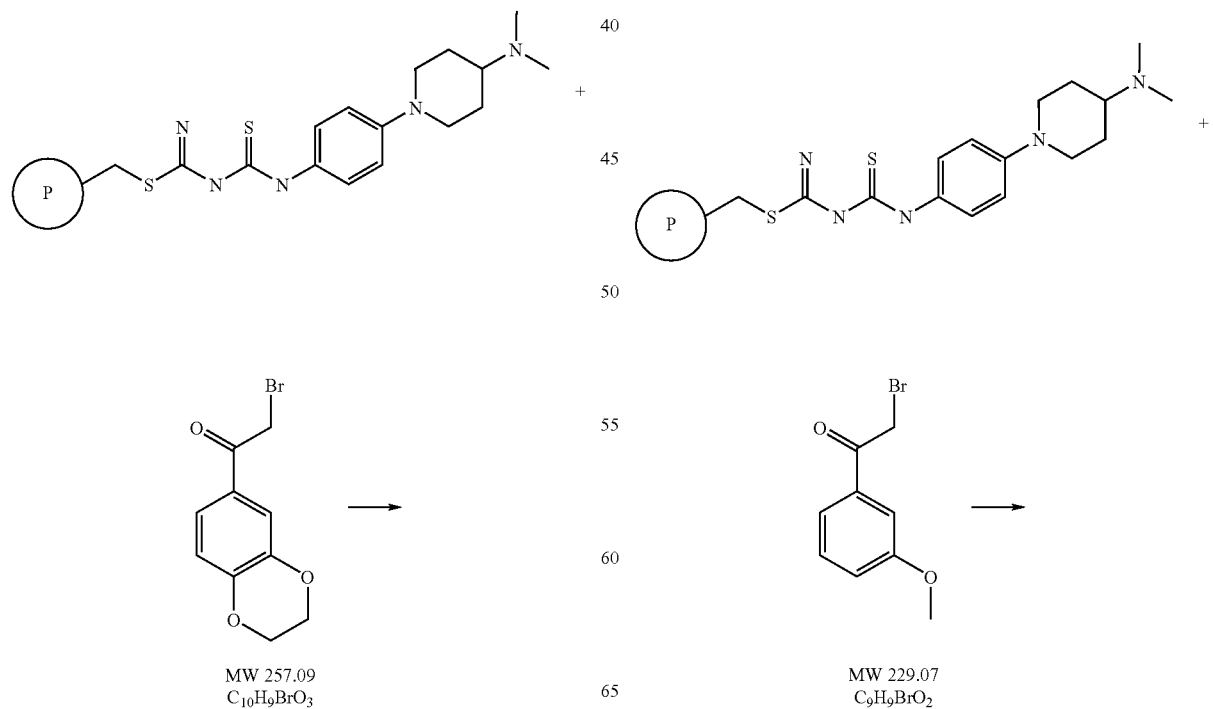

MW 257.09
C10H9BrO3

MW 229.07
C9H9BrO2

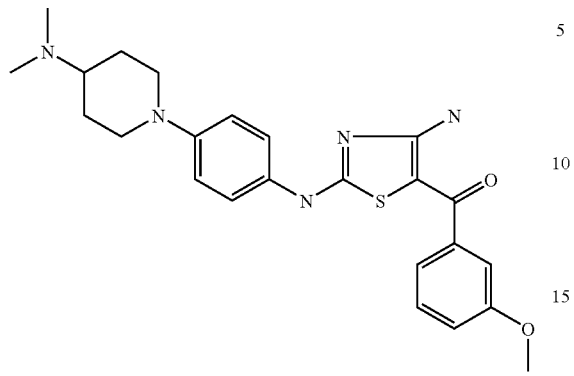

MW 451.60
C24H29N5O2S

The compound was prepared from 2-bromo-1-(3-methoxy-phenyl)-ethanone (Maybridge International) and the resin-bound thiourea of Example 18 following the procedure used in Example 23. MS (m+H)+: 452.

Example 46

{4-Amino-2-[4-(4-dimethylamino-piperidin-1-yl)-phenylamino]-thiazol-5-yl}-(4-hydroxy-phenyl)-methanone

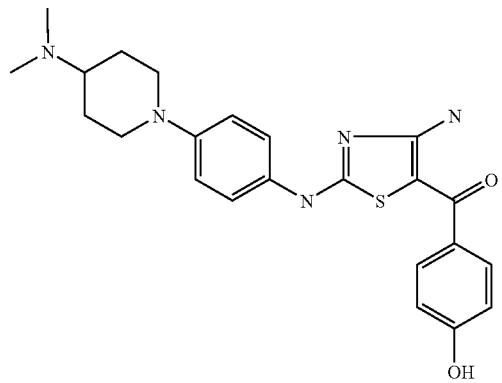

MW 437.5679
C23H27N5O2S

The compound was prepared from 2-bromo-1-(4-hydroxy-phenyl)-ethanone (ChonTech) and the resin-bound thiourea of Example 18 following the procedure used in Example 23. MS (m+H)+: 438.

Example 47

4-{4-Amino-2-[4-(4-dimethylamino-piperidin-1-yl)-phenylamino]-thiazole-5-carbonyl}-benzonitrile

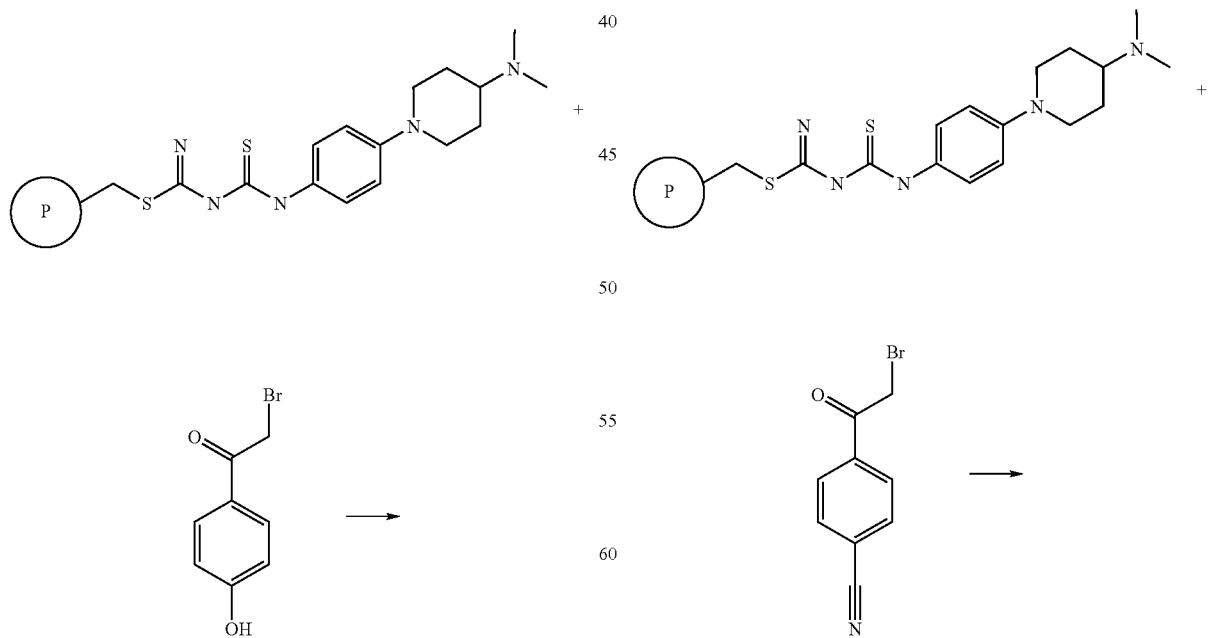

MW 215.05
C8H7BrO2

MW 224.06
C9H6BrNO

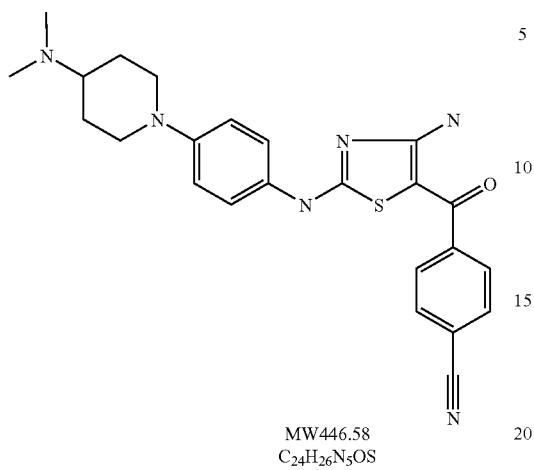

MW446.58
C$_{24}$H$_{26}$N$_5$OS

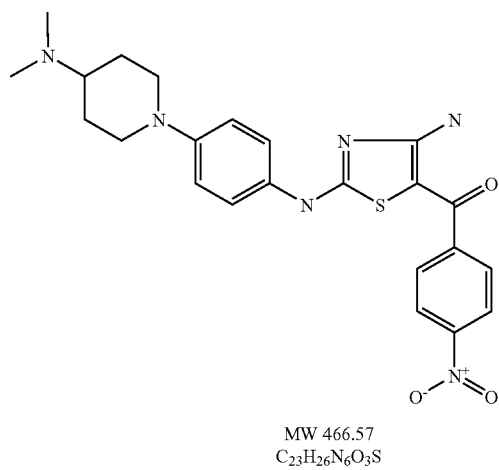

MW 466.57
C$_{23}$H$_{26}$N$_6$O$_3$S

The compound was prepared from 4-(2-bromo-acetyl)-benzonitrile (Aldrich) and the resin-bound thiourea of Example 18 following the procedure used in Example 23. MS (m+H)$^+$: 447.

Example 48

{4-Amino-2-[4-(4-dimethylamino-piperidin-1-yl)-phenylamino]-thiazol-5-yl}-(4-nitro-phenyl)-methanone The compound was prepared from 2-bromo-1-(4-nitro-phenyl)-ethanone (Aldrich) and the resin-bound thiourea of Example 18 following the procedure used in Example 23. MS (m+H)$^+$: 467.

Example 49

{4-Amino-2-[4-(4-dimethylamino-piperidin-1-yl)-phenylamino]-thiazol-5-yl}-(3-methoxy-2-nitro-phenyl)-methanone

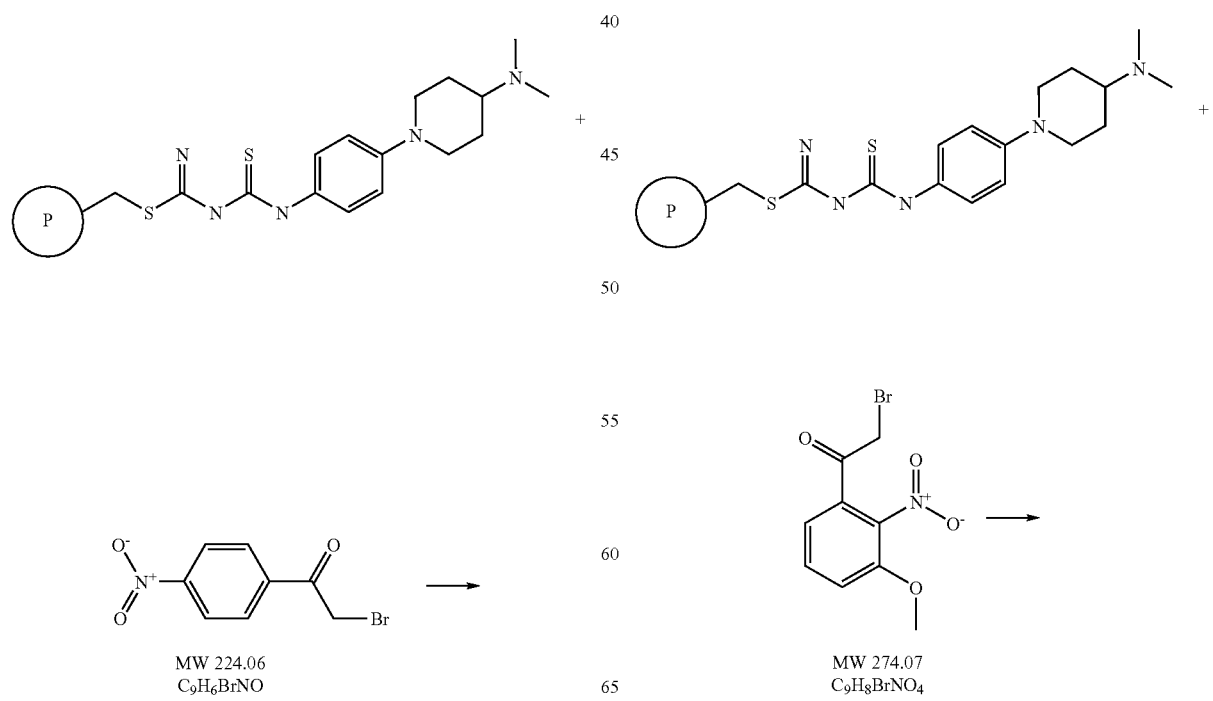

MW 224.06
C$_9$H$_6$BrNO

MW 274.07
C$_9$H$_8$BrNO$_4$

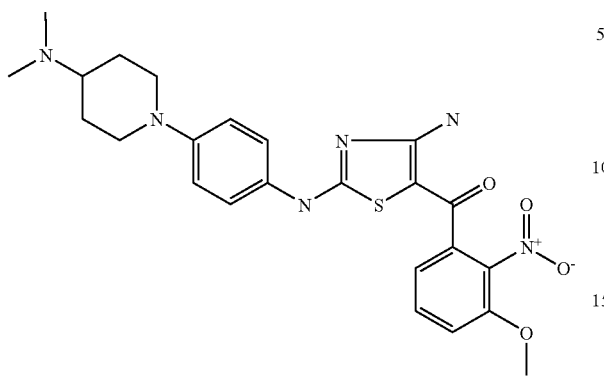

MW 496.59
$C_{24}H_{28}N_6O_4S$

The compound was prepared from 2-bromo-1-(3-methoxy-2-nitro-phenyl)-ethanone (Aldrich) and the resin-bound thiourea of Example 18 following the procedure used in Example 23. MS (m+H)$^+$: 497.

Example 50

{4-Amino-2-[4-(4-dimethylamino-piperidin-1-yl)-phenylamino]-thiazol-5-yl}-(3-hydroxy-phenyl)-methanone

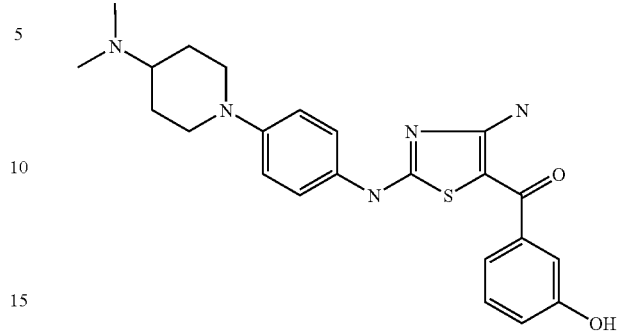

MW 437.57
$C_{23}H_{27}N_5O_2S$

The compound was prepared from 2-bromo-1-(3-hydroxy-phenyl)-ethanone (Example 95, also see procedure of Pasaribu, S. J. et al. Australian Journal of Chemistry. 1973, 26(6), 1327–31) and the resin-bound thiourea of Example 18 following the procedure used in Example 23. MS (m+H)$^+$: 438.

Example 51

4-{4-Amino-2-[4-(3-hydroxy-[1,4']bipiperidinyl-1'-yl)-phenylamino]-thiazole-5-carbonyl}-benzonitrile

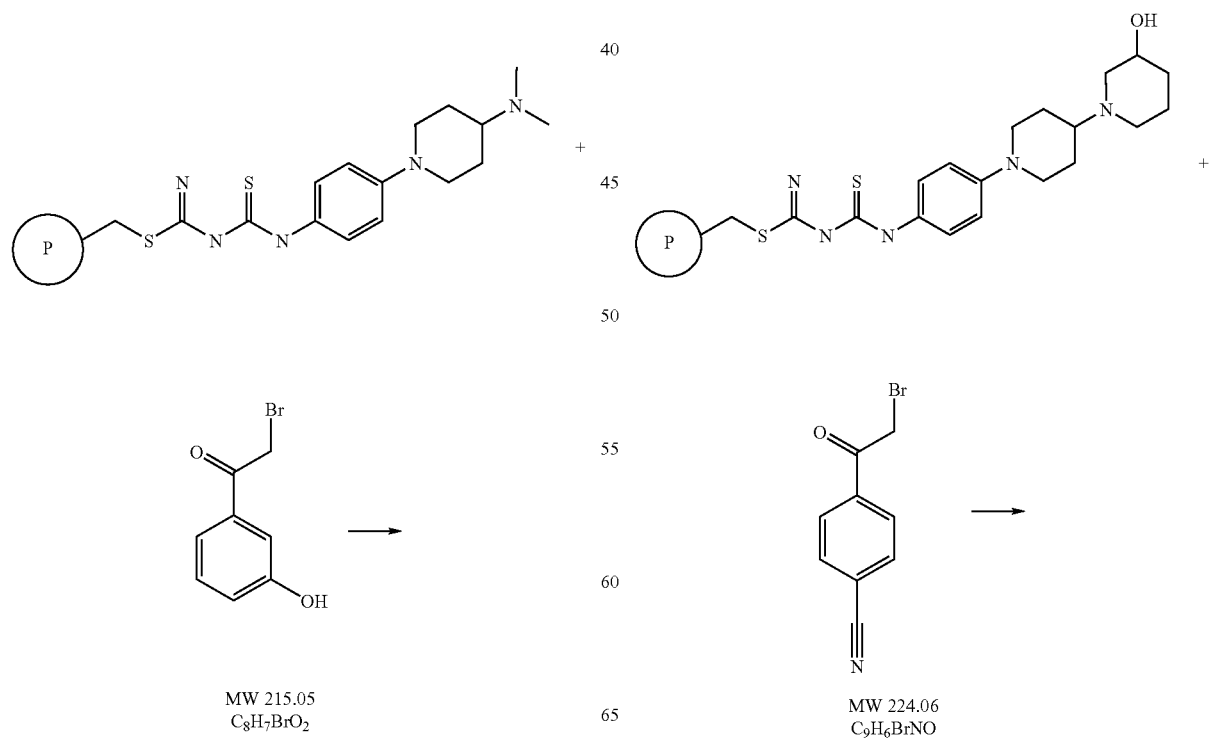

MW 215.05
$C_8H_7BrO_2$

MW 224.06
$C_9H_6BrNO$

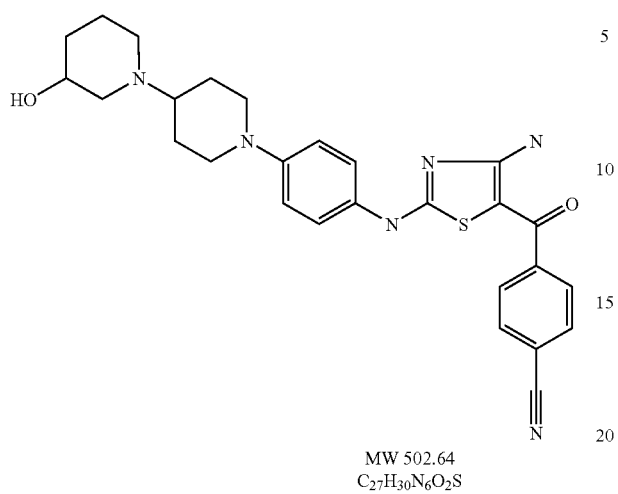

MW 502.64
C27H30N6O2S

MW 522.63
C25H30N6O4S

The compound was prepared from 4-(2-bromo-acetyl)-benzonitrile (Aldrich) and the resin-bound thiourea of Example 21 following the procedure used in Example 23. MS (m+H)+: 503.

The compound was prepared from 2-bromo-1-(4-nitro-phenyl)-ethanone (Aldrich) and the resin-bound thiourea of Example 21 following the procedure used in Example 23. MS (m+H)+: 523.

Example 52

{4-Amino-2-[4-(3-hydroxy-[1,4′]bipiperidinyl-1′-yl)-phenylamino]-thiazol-5-yl}-(4-nitro-phenyl)-methanone Example 53

{4-Amino-2-[4-(4-pyrrolidin-1-yl-piperidin-1-yl)-phenylamino]-thiazol-5-yl}-(4-nitro-phenyl)-methanone

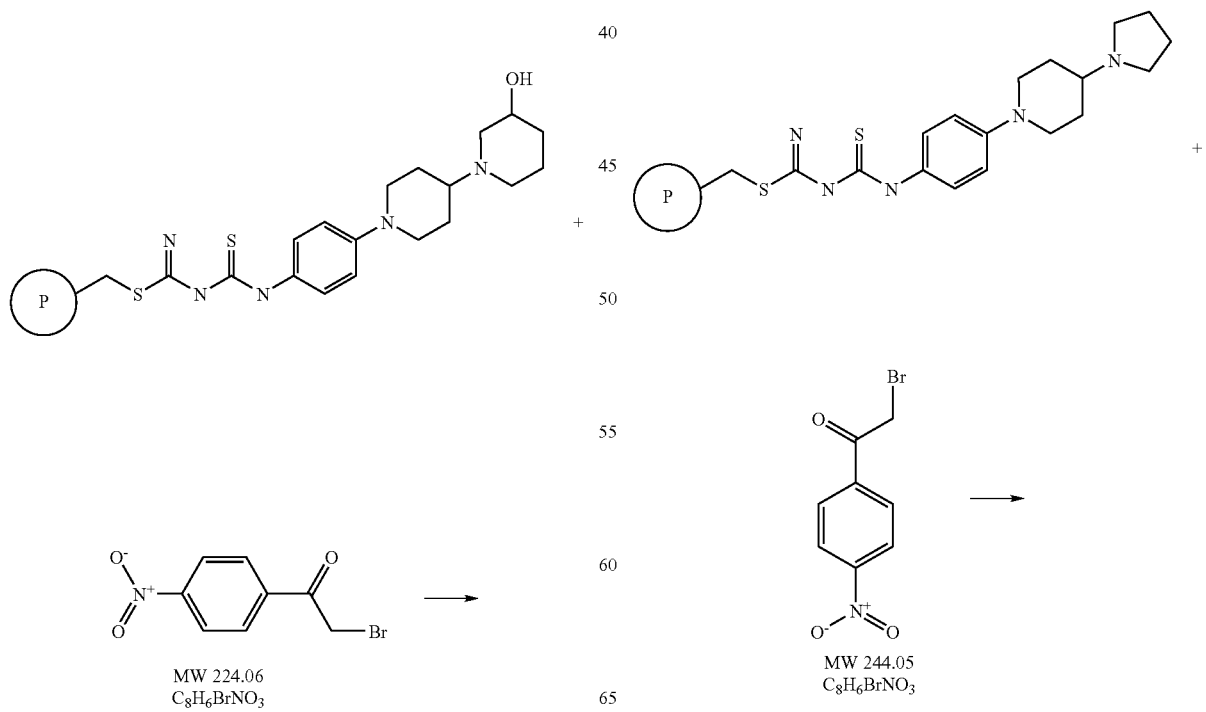

MW 224.06
C8H6BrNO3

MW 244.05
C8H6BrNO3

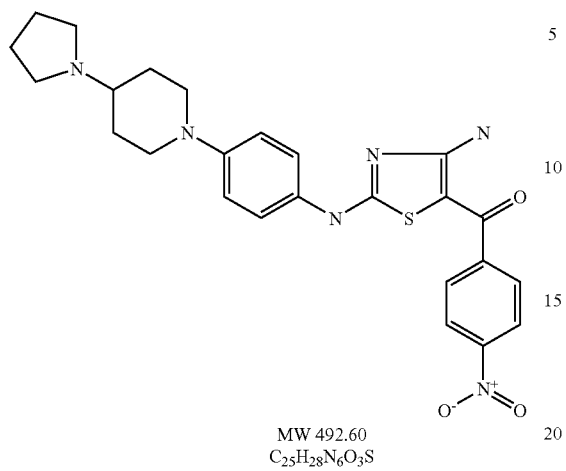

MW 492.60
C25H28N6O3S

The compound was prepared from 2-bromo-1-(4-nitro-phenyl)-ethanone (Aldrich) and the resin-bound thiourea of Example 20 following the procedure used in Example 23. MS (m+H)+: 493.

Example 54

4-{4-Amino-2-[4-(4-pyrrolidin-1-yl-piperidin-1-yl)-phenylamino]-thiazole-5-carbonyl}-benzonitrile

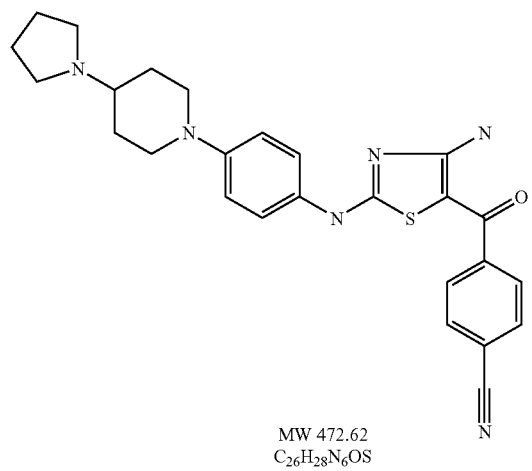

MW 472.62
C26H28N6OS

The compound was prepared from 4-(2-bromo-acetyl)-benzonitrile (Aldrich) and the resin-bound thiourea of Example 20 following the procedure used in Example 23. MS (m+H)+: 473.

Example 55

4-[4-Amino-2-(4-[1,4']bipiperidinyl-1'-yl-pheny-lamino)-thiazole-5-carbonyl]-benzonitrile

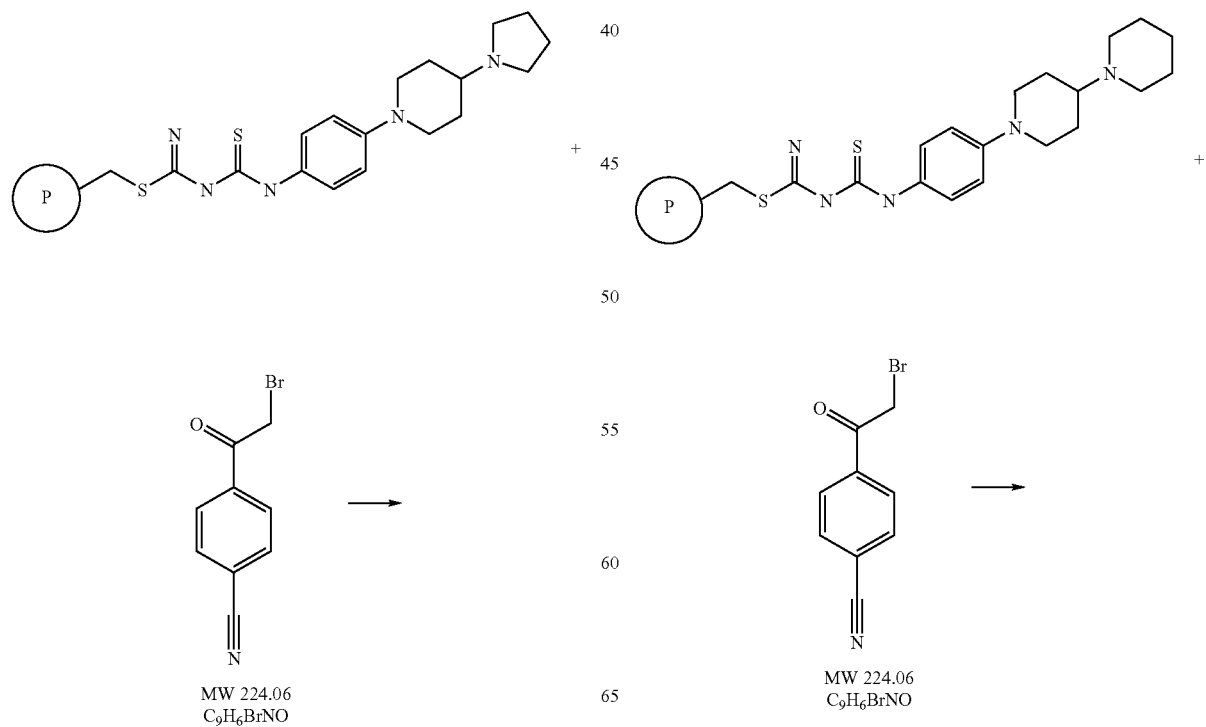

MW 224.06
C9H6BrNO

MW 224.06
C9H6BrNO

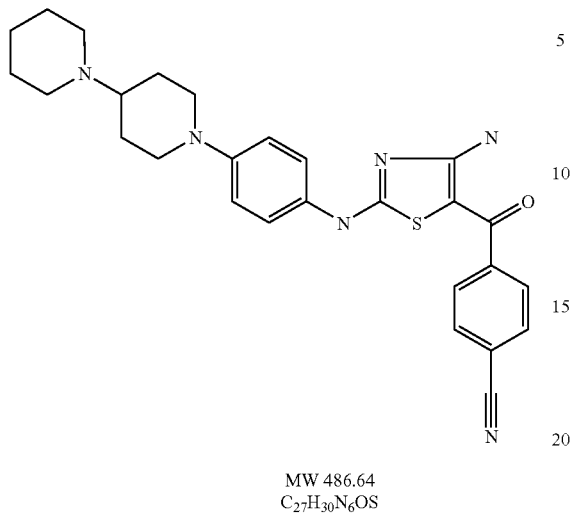

MW 486.64
C₂₇H₃₀N₆OS

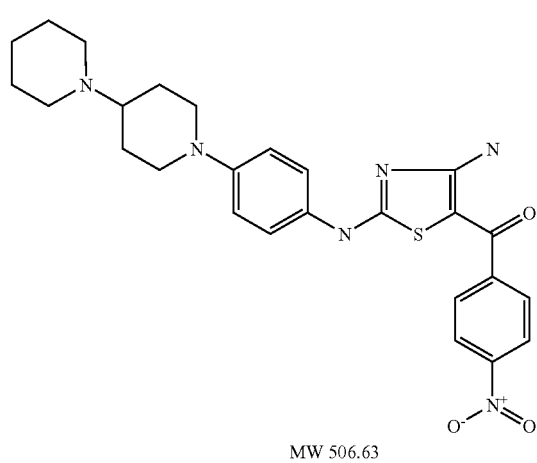

MW 506.63
C₂₆H₃₀N₆O₃S

The compound was prepared from 4-(2-bromo-acetyl)-benzonitrile (Aldrich) and the resin-bound thiourea of Example 19 following the procedure used in Example 23. MS (m+H)⁺: 487.

The compound was prepared from 2-bromo-1-(4-nitrophenyl)-ethanone (Aldrich) and the resin-bound thiourea of Example 19 following the procedure used in Example 23. MS (m+H)⁺: 507.

Example 56

[4-Amino-2-(4-[1,4']bipiperidinyl-1'-yl-phenylamino)-thiazol-5-yl]-(4-nitro-phenyl)-methanone Example 57

[4-Amino-2-(4-[1,4']bipiperidinyl-1'-yl-phenylamino)-thiazol-5-yl]-(3,5-difluoro-phenyl)-methanone

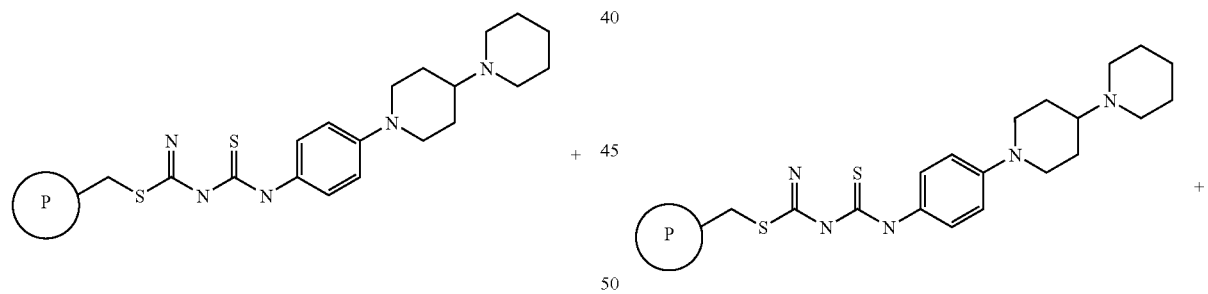

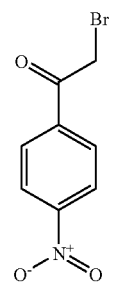

MW 244.05
C₈H₈BrNO₃

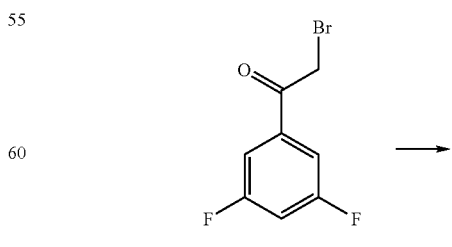

MW 235.03
C₈H₅BrF₂O

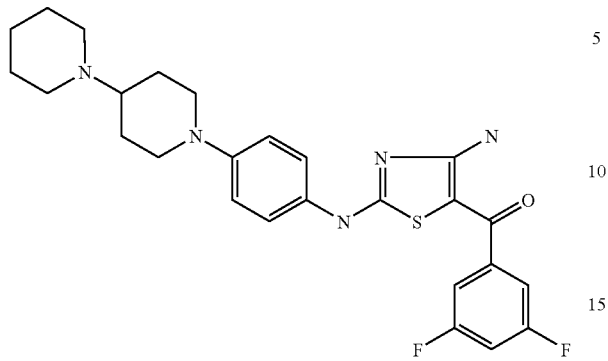

MW 497.61
$C_{28}H_{29}F_2N_5OS$

MW 496.08
$C_{26}H_{30}ClN_5OS$

The compound was prepared from 2-bromo-3',4'-difluoro-acetophenone (prepared from the procedure described by Chu, Xin-Jie et al, WO2003097048) and the resin-bound thiourea of Example 19 following the procedure used in Example 23. MS (m+H)⁺: 498.

The compound was prepared from 2-bromo4'-fluoro-acetophenone (ABCR) and the resin-bound thiourea of Example 19 following the procedure used in Example 23. MS (m+H)⁺: 497.

Example 58

[4-Amino-2-(4-[1,4']bipiperidinyl-1'-yl-phenylamino)-thiazol-5-yl]-(4-chloro-phenyl)-methanone Example 59

[4-Amino-2-(4-[1,4']bipiperidinyl-1'-yl-phenylamino)-thiazol-5-yl]-(3,4-difluoro-phenyl)-methanone

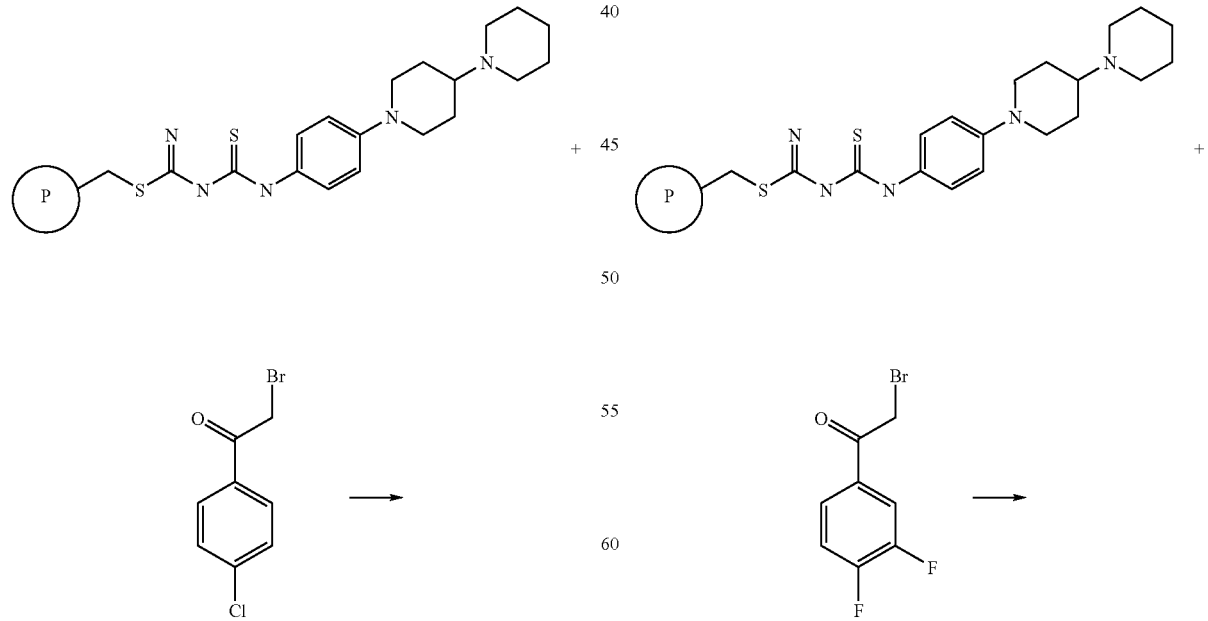

MW 233.49
$C_8H_6BrClO$

MW 235.03
$C_8H_5BrF_2O$

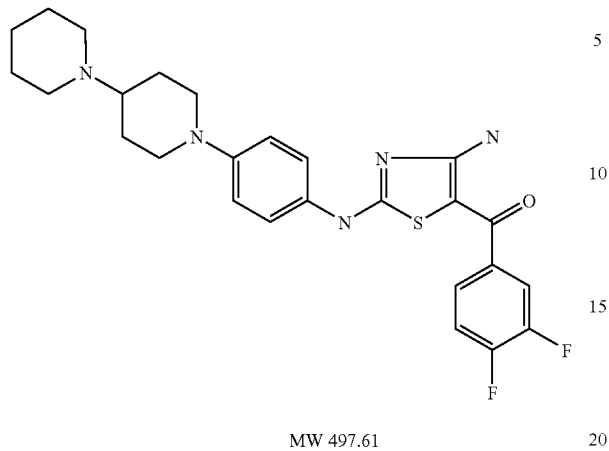

MW 497.61
$C_{26}H_{29}F_2N_5OS$

MW 530.52
$C_{26}H_{29}Cl_2N_5OS$

The compound was prepared from 2-bromo-3',4'-difluoro-acetophenone (ABCR) and the resin-bound thiourea of Example 19 following the procedure used in Example 23. MS (m+H)+: 498.

The compound was prepared from 2-bromo-3',4'-dichloro-acetophenone (ABCR) and the resin-bound thiourea of Example 19 following the procedure used in Example 23. MS (m+H)+: 529.

Example 60

[4-Amino-2-(4-[1,4']bipiperidinyl-1'-yl-phenylamino)-thiazol-5-yl]-(3,4-dichloro-phenyl)-methanone

Example 61

[4-Amino-2-(4-[1,4']bipiperidinyl-1'-yl-phenylamino)-thiazol-5-yl]-(4-fluoro-phenyl)-methanone

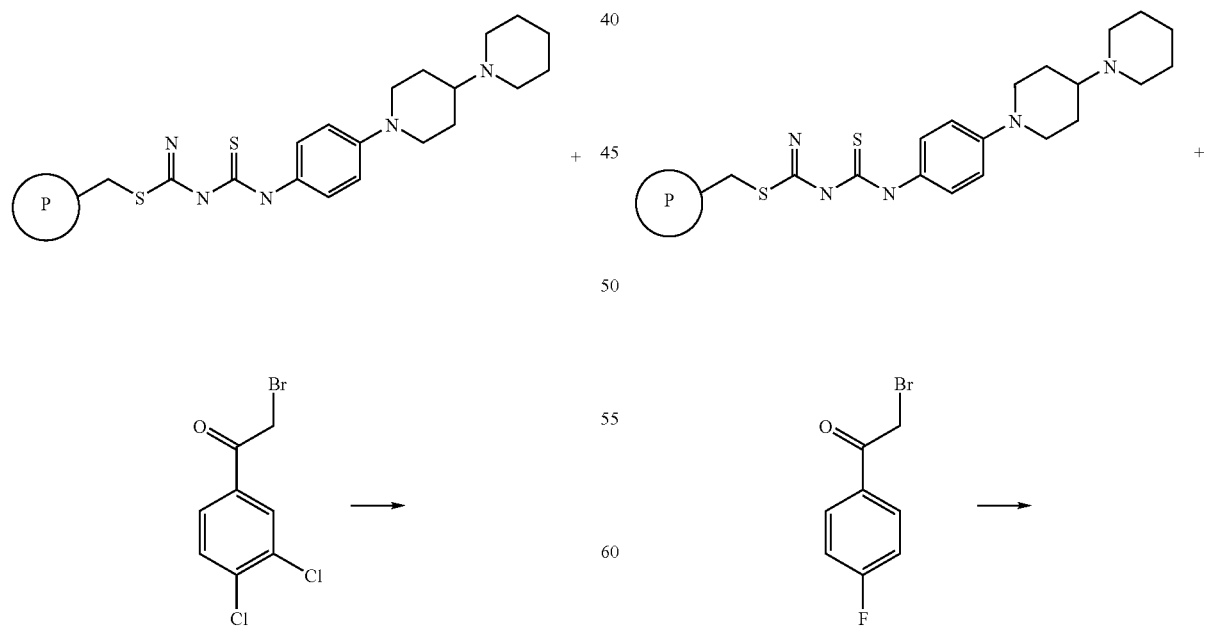

MW 267.94
$C_8H_5BrCl_2O$

MW 217.0388
$C_8H_6BrFO$

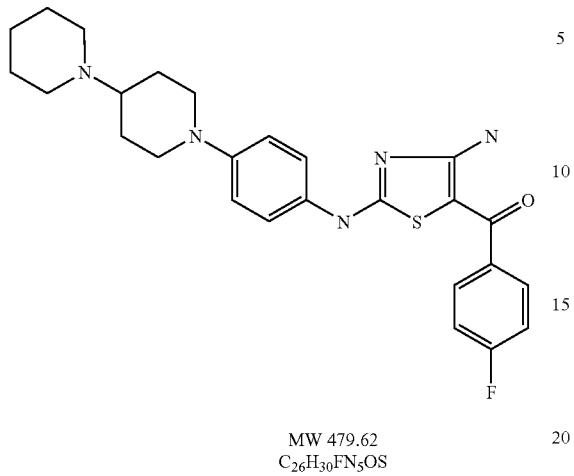

MW 479.62
C26H30FN5OS

The compound was prepared from 2-bromo-4'-fluoro-acetophenone (ABCR) and the resin-bound thiourea of Example 19 following the procedure used in Example 23. MS (m+H)+: 480.

Example 62

[4-Amino-2-(4-[1,4']bipiperidinyl-1'-yl-phenylamino)-thiazol-5-yl]-(4-chloro-3-nitro-phenyl)-methanone

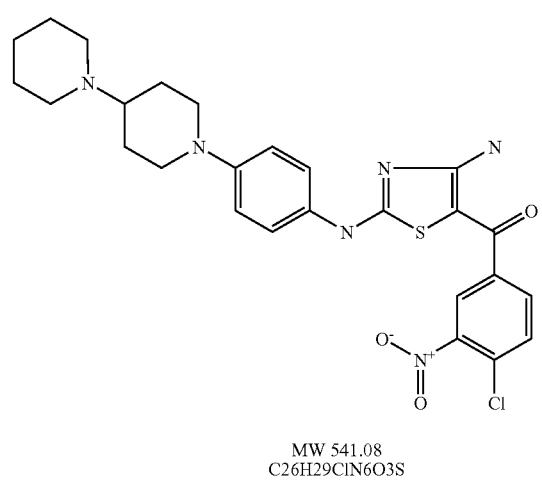

MW 541.08
C26H29ClN6O3S

The compound was prepared from 2-bromo-3'-nitro-4'-chloro-acetophenone (ABCR) and the resin-bound thiourea of Example 19 following the procedure used in Example 23. MS (m+H)+: 541.

Example 63

4-[4-Amino-2-(4-[1,4']bipiperidinyl-1'-yl-phenylamino-thiazole-5-carbonyl]-benzoic acid

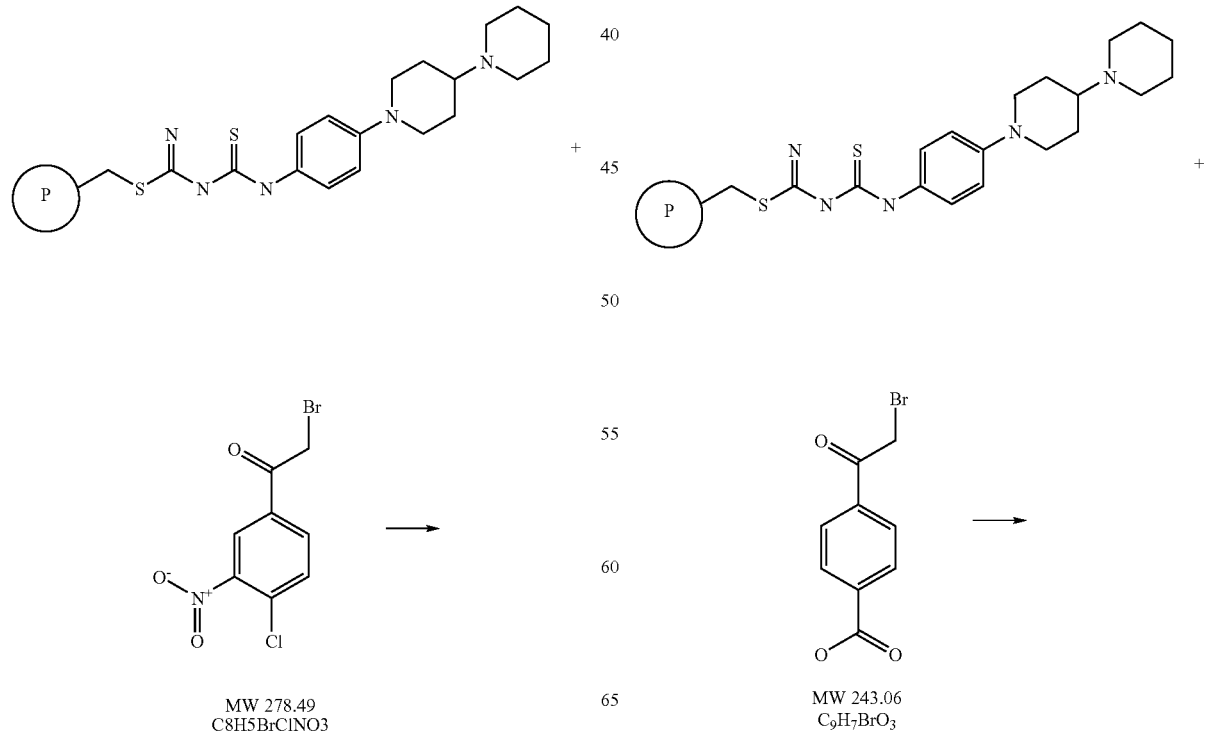

MW 278.49
C8H5BrClNO3

MW 243.06
C9H7BrO3

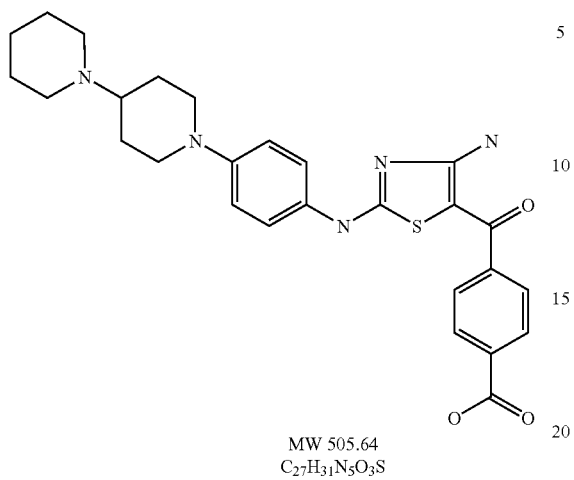

The compound was prepared from 2-bromo-4'-hydroxy-carbonyl-acetophenone (Oakwood) and the resin-bound thiourea of Example 19 following the procedure used in Example 23. MS (m+H)⁺: 506.

Example 64

3-[4-Amino-2-(4-[1,4']bipiperidinyl-1'-yl-phen-lamino)-thiazole-5-carbonyl]-benzonitrile The compound was prepared from 2-bromo-4'-cyano-acetophenone (Oakwood) and the resin-bound thiourea of Example 19 following the procedure used in Example 23. MS (m+H)⁺: 487.

Example 65

[4-Amino-2-(4-[1,4']bipiperidinyl-1'-yl-pheny-lamino)-thiazol-5-yl]-(3-hydroxy-phenyl)-methanone

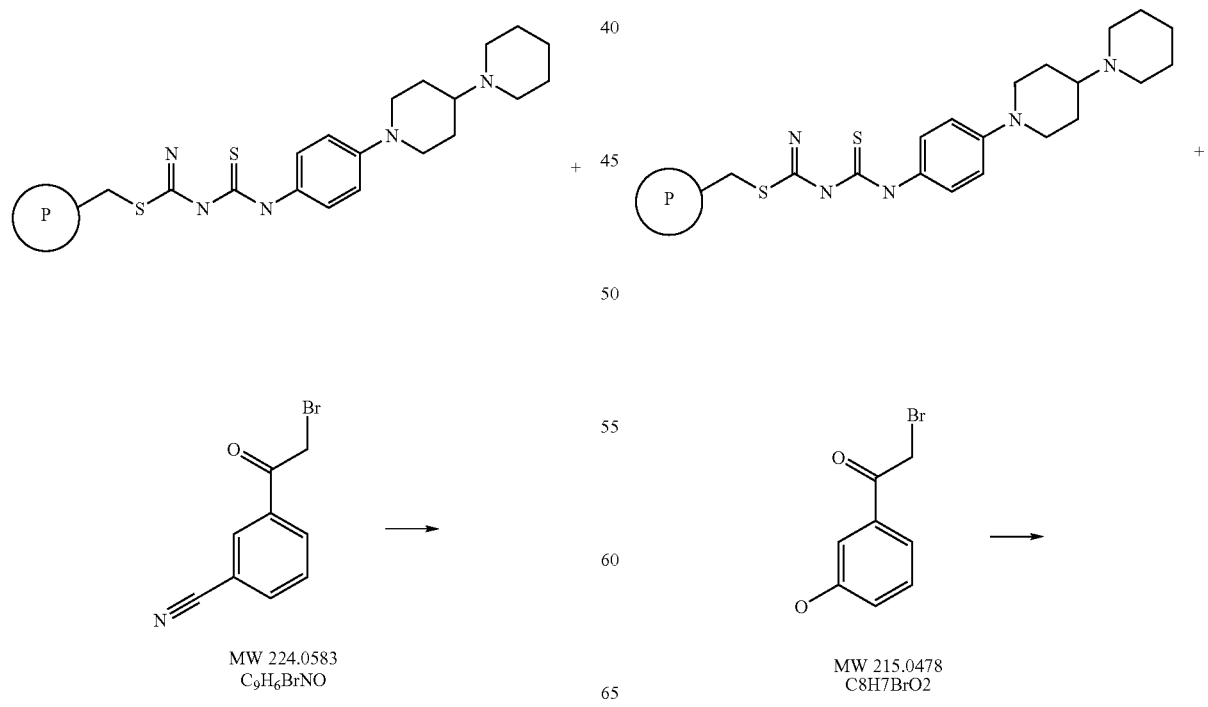

77

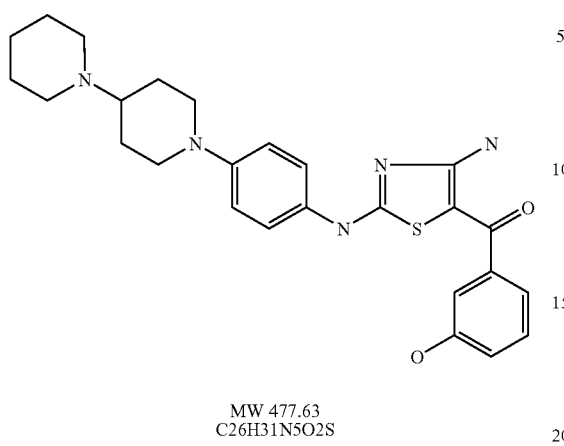

MW 477.63
C26H31N5O2S

The compound was prepared from 2-bromo-4'-hydroxy-acetophenone (example 95) and the resin-bound thiourea of Example 19 following the procedure used in Example 23. MS (m+H)+: 478.

Example 66

{4-Amino-2-[4-(4-pyrrolidin-1-yl-piperidin-1-yl)-phenylamino]-thiazol-5-yl}-(3,5-difluoro-phenyl)-methanone

78

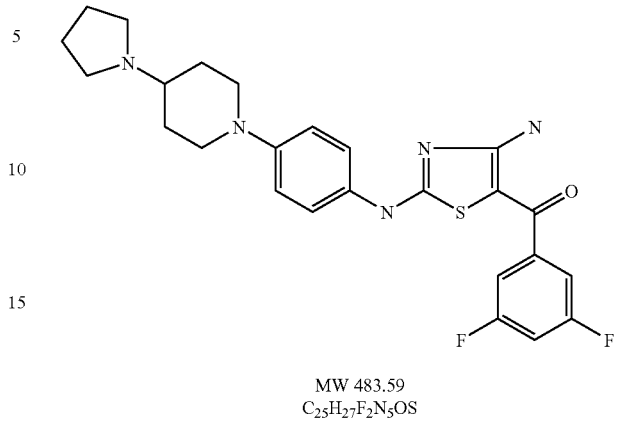

MW 483.59
C25H27F2N5OS

The compound was prepared from 2-bromo-3',4'-difluoro-acetophenone (prepared from the procedure described by Chu, Xin-Jie et al, WO2003097048) and the resin-bound thiourea of Example 20 following the procedure used in Example 23. MS (m+H)+: 484.

Example 67

{4-Amino-2-[4-(4-pyrrolidin-1-yl-piperidin-1-yl)-phenylamino]-thiazol-5-yl}-(4-chloro-phenyl)-methanone

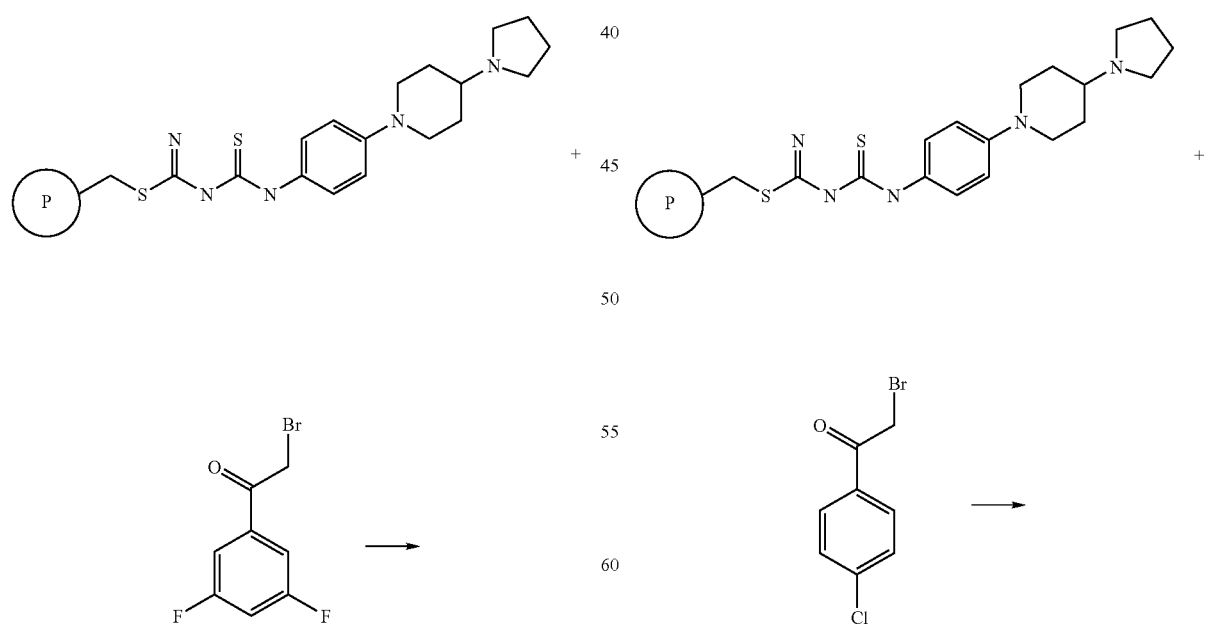

MW 235.0292
C8H5BrF2O

MW 233.49
C8H6BrClO

-continued

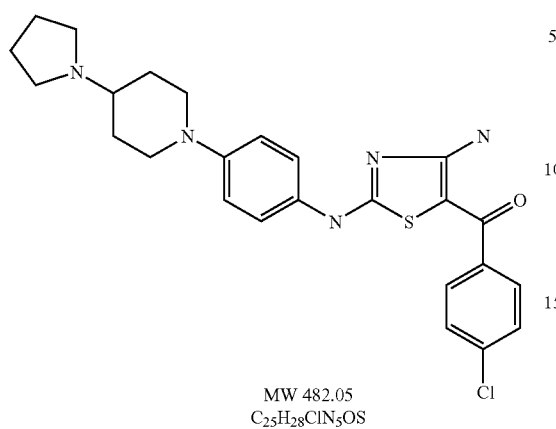

MW 482.05
C25H28ClN5OS

The compound was prepared from 2-bromo-4'-fluoro-acetophenone (ABCR) and the resin-bound thiourea of Example 20 following the procedure used in Example 23. MS (m+H)+: 483.

Example 68

{4-Amino-2-[4-(4-pyrrolidin-1-yl-piperidin-1-yl)-phenylamino]-thiazol-5-yl}-(3,4-difluoro-phenyl)-methanone -continued

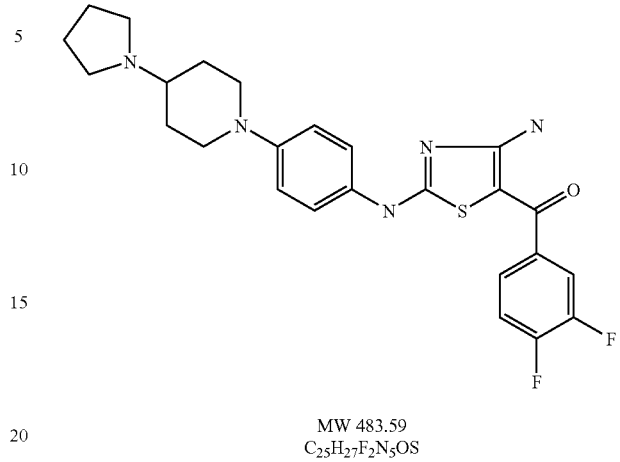

MW 483.59
C25H27F2N5OS

The compound was prepared from 2-bromo-3',4'-difluoro-acetophenone (ABCR) and the resin-bound thiourea of Example 20 following the procedure used in Example 23. MS (m+H)+: 484.

Example 69

[{4-Amino-2-[4-(4-pyrrolidin-1-yl-piperidin-1-yl)-phenylamino]-thiazol-5-yl}-(3,4-dichloro-phenyl)-methanone

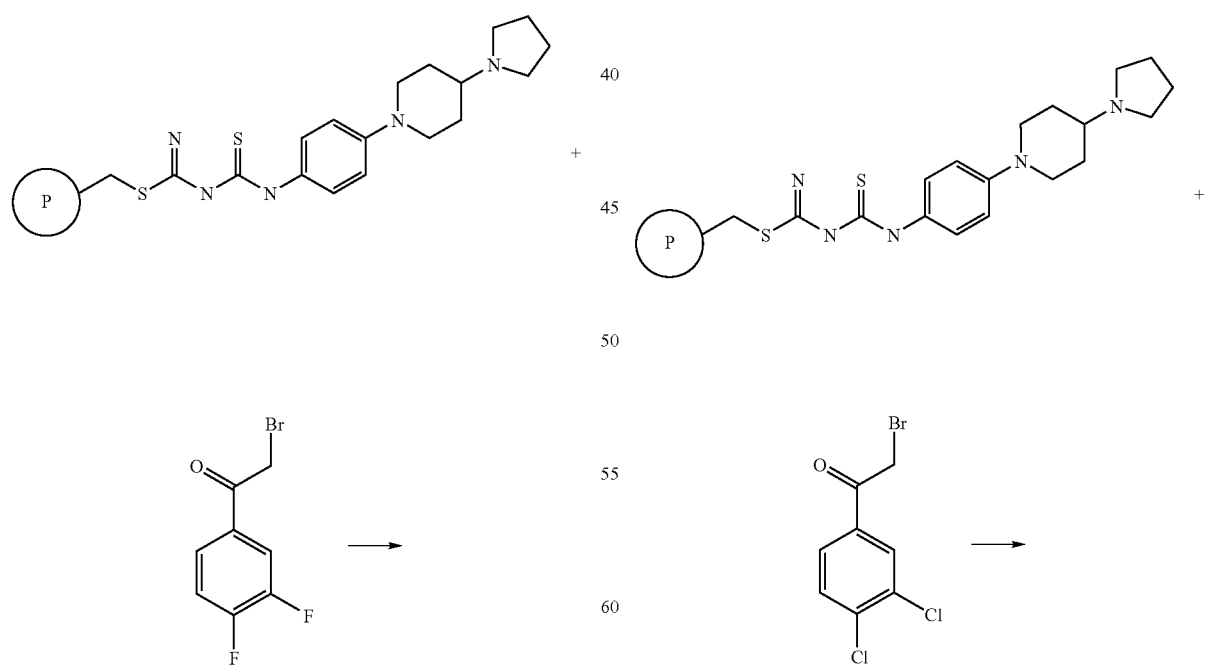

MW 235.03
C8H5BrF2O

MW 267.94
C8H5BrCl2O

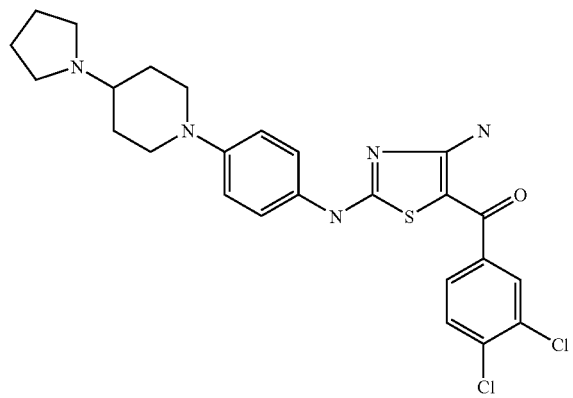

MW 516.50
C25H27Cl2N5OS

The compound was prepared from 2-bromo-3',4'-dichloro-acetophenone (ABCR) and the resin-bound thiourea of Example 20 following the procedure used in Example 23. MS (m+H)+: 516.

Example 70

{4-Amino-2-[4-(4-pyrrolidin-1-yl-piperidin-1-yl)-phenylamino]-thiazol-5-yl}-(4-fluoro-phenyl)-methanone

MW 465.5972
C25H28FN5OS

The compound was prepared from 2-bromo-4'-fluoro-acetophenone (ABCR) and the resin-bound thiourea of Example 20 following the procedure used in Example 23. MS (m+H)+: 466.

Example 71

{4-Amino-2-[4-(4-pyrrolidin-1-yl-piperidin-1-yl)-phenylamino]-thiazol-5-yl}-(4-chloro-3-nitro-phenyl)-methanone

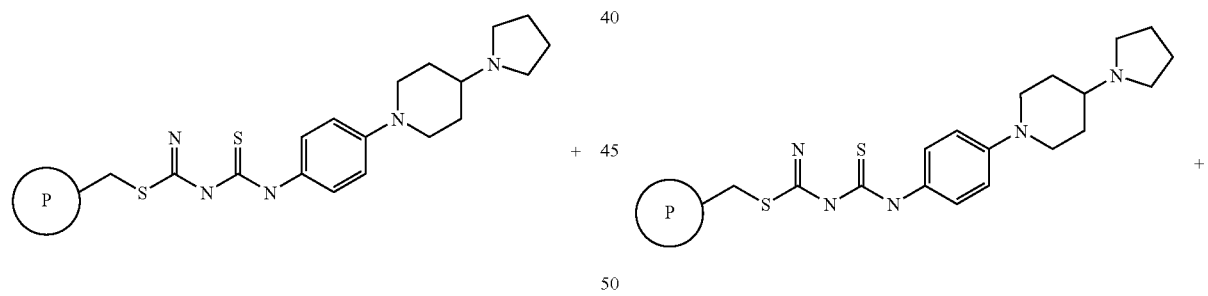

+

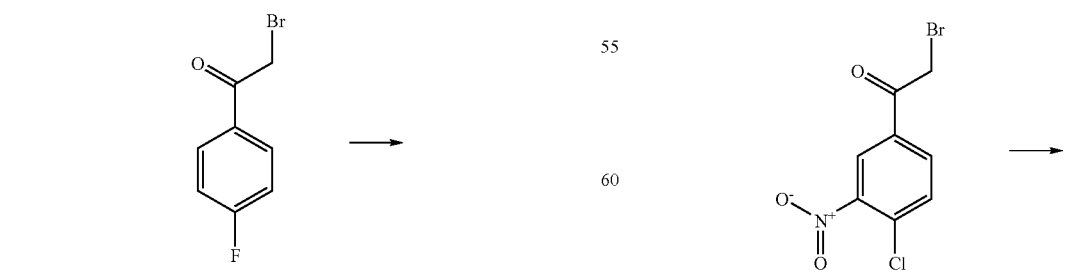

MW 217.0388
C8H6BrFO

MW 278.49
C8H5BrClO3

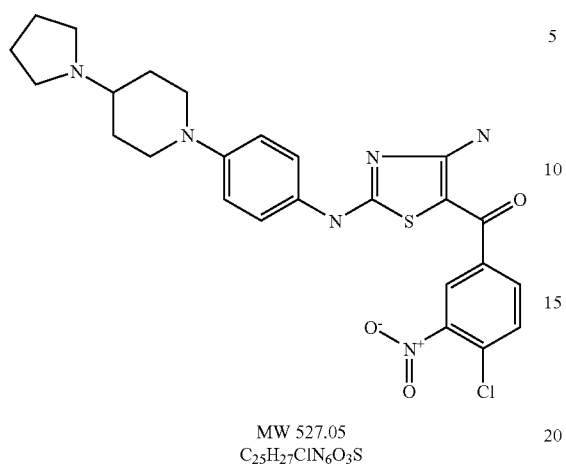

MW 527.05
$C_{25}H_{27}ClN_6O_3S$

The compound was prepared from 2-bromo-3'-nitro-4'-chloro-acetophenone (ABCR) and the resin-bound thiourea of Example 20 following the procedure used in Example 23. MS (m+H)⁺: 527.

Example 72

3-{4-Amino-2-[4-(4-pyrrolidin-1-yl-piperidin-1-yl)-phenylamino]-thiazole-5-carbonyl}-benzonitrile

MW 472.6167
$C_{26}H_{28}N_6OS$

The compound was prepared from 2-bromo-4'-cyano-acetophenone (Oakwood) and the resin-bound thiourea of Example 20 following the procedure used in Example 23. MS (m+H)⁺: 473.

Example 73

{4-Amino-2-[4-(3-hydroxy-[1,4']bipiperidinyl-1'-yl)-phenylamino]-thiazol-5-yl}-(3,5-difluoro-phenyl)-methanone

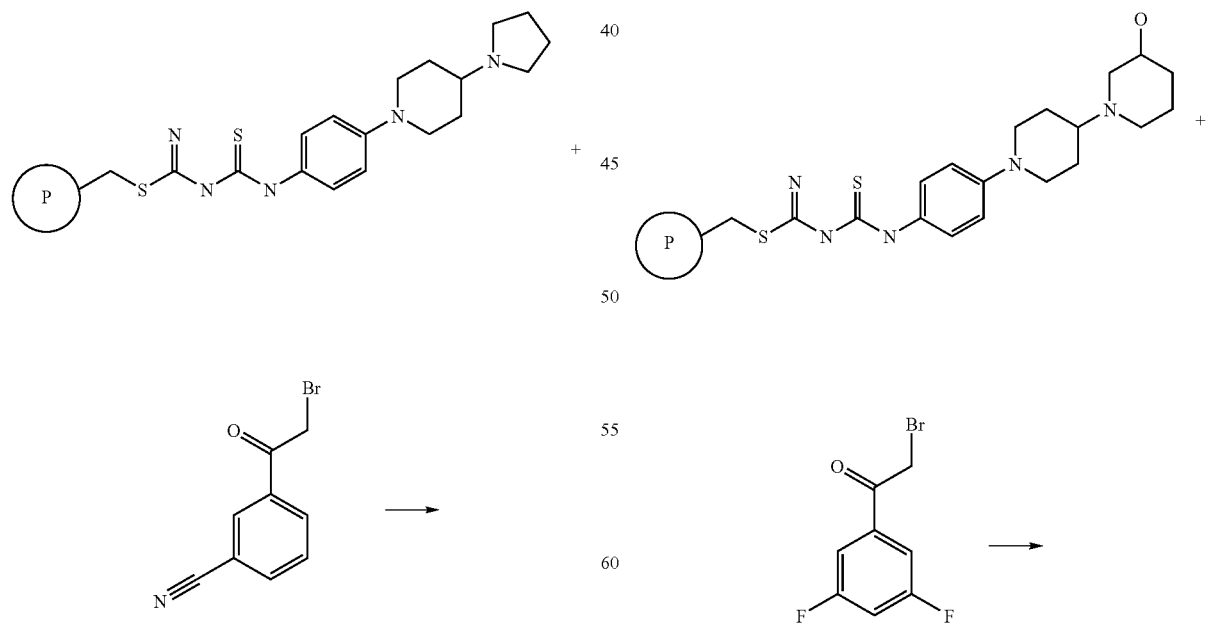

MW 224.0583
$C_9H_6BrNO$

MW 235.03
$C_8H_5BrF_2O$

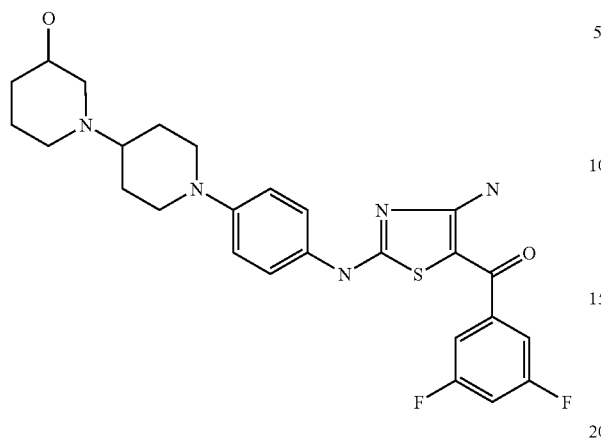

MW 513.61
C26H29F2N5O2S

The compound was prepared from 2-bromo-3',4'-difluoro-acetophenone (prepared from the procedure described by Chu, Xin-Jie et al, WO2003097048) and the resin-bound thiourea of Example 21 following the procedure used in Example 23. MS (m+H)+: 514.

Example 74

{4-Amino-2-[4-(3-hydroxy-[1,4']bipiperidinyl-1'-yl)-phenylamino]-thiazol-5-yl}-(4-chloro-phenyl)-methanone

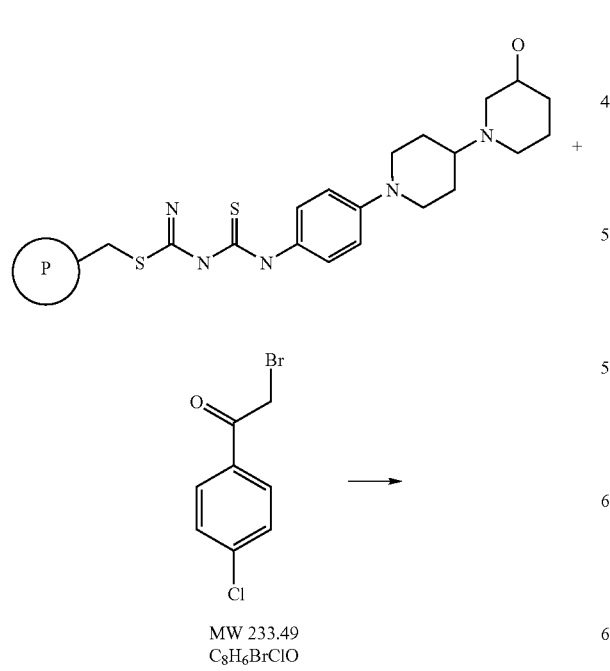

MW 233.49
C8H6BrClO

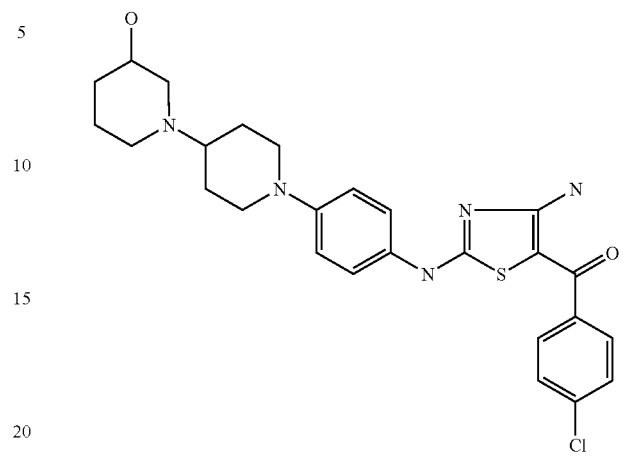

MW 512.08
C26H30ClN5O2S

The compound was prepared from 2-bromo-4'-fluoro-acetophenone (ABCR) and the resin-bound thiourea of Example 21 following the procedure used in Example 23. MS (m+H)+: 512.

Example 75

{4-Amino-2-[4-(3-hydroxy-[1,4']bipiperidinyl-1'-yl)-phenylamino]-thiazol-5-yl}-(3,4-difluoro-phenyl)-methanone

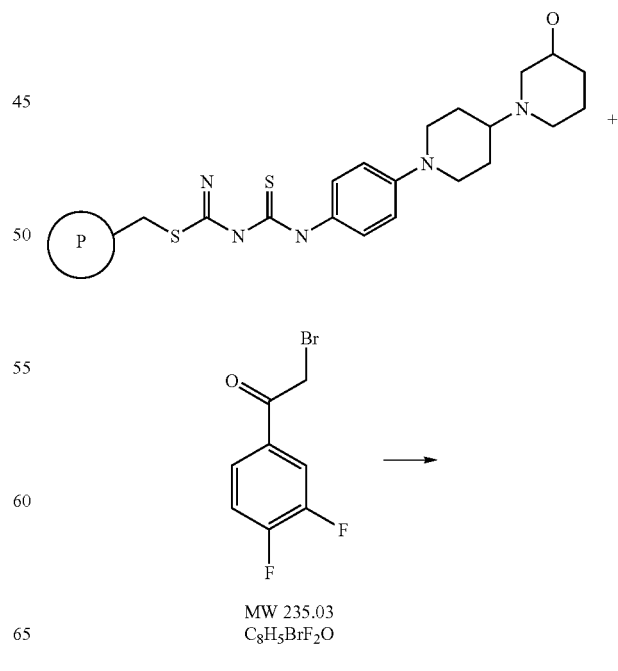

MW 235.03
C8H5BrF2O

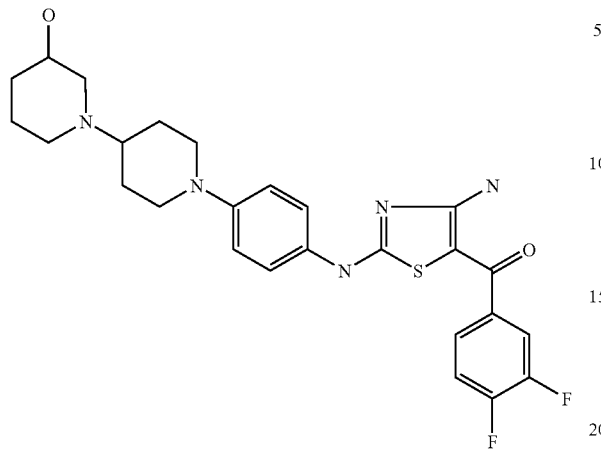

MW 513.61
$C_{26}H_{29}F_2N_5O_2S$

The compound was prepared from 2-bromo-3',4'-difluoro-acetophenone (ABCR) and the resin-bound thiourea of Example 21 following the procedure used in Example 23. MS (m+H)⁺: 514.

Example 76

{4-Amino-2-[4-(3-hydroxy-[1,4']bipiperidinyl-1'-yl)-phenylamino]-thiazol-5-yl}-(3,4-dichloro-phenyl)-methanone

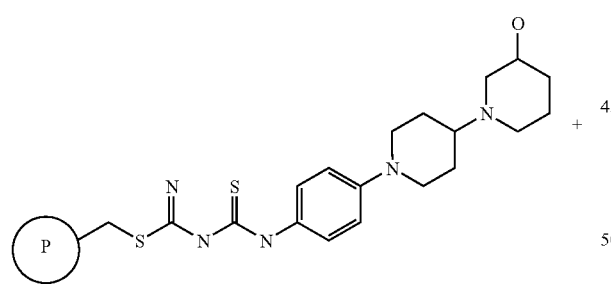

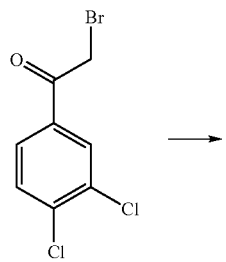

MW 267.94
$C_8H_5BrCl_2O$

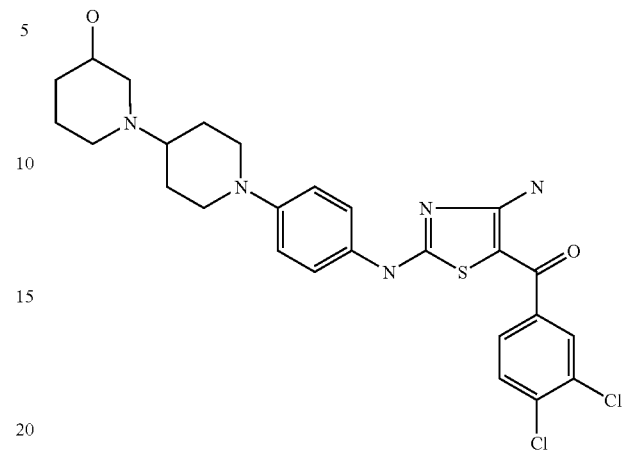

MW 546.52
$C_{26}H_{29}Cl_2N_5O_2S$

The compound was prepared from 2-bromo-3',4'-chloro-acetophenone (ABCR) and the resin-bound thiourea of Example 21 following the procedure used in Example 23. MS (m+H)⁺: 546.

Example 77

{4-Amino-2-[4-(3-hydroxy-[1,4']bipiperidinyl-1'-yl)-phenylamino]-thiazol-5-yl}-(4-fluoro-phenyl)-methanone

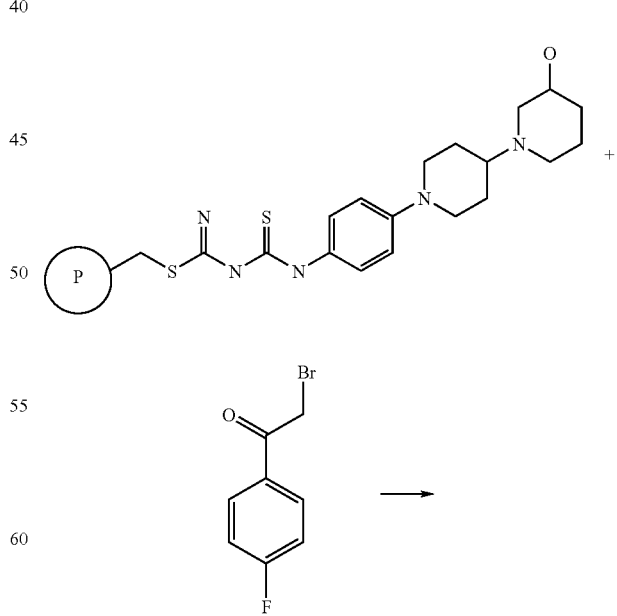

MW 217.0388
$C_8H_6BrFO$

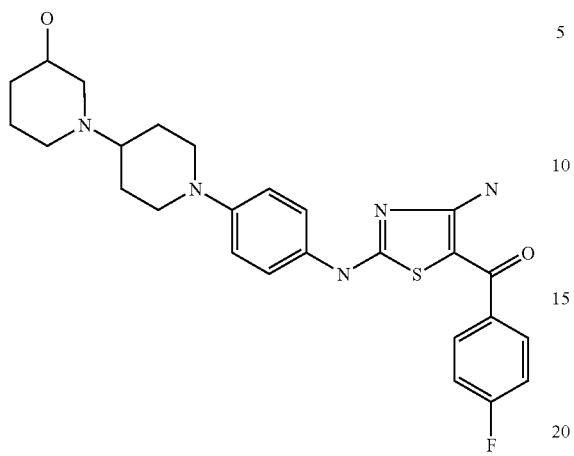

MW 495.62
C26H30FN5O2S

The compound was prepared from 2-bromo-4'-fluoro-acetophenone (ABCR) and the resin-bound thiourea of Example 21 following the procedure used in Example 23. MS (m+H)+: 496.

Example 78

{4-Amino-2-[4-(3-hydroxy-[1,4']bipiperidinyl-1'-yl)-phenylamino]-thiazol-5-yl}-(4-chloro-3-nitro-phenyl)-methanone

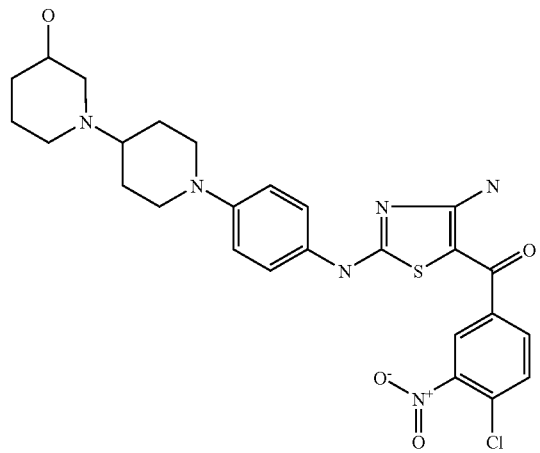

MW 557.08
C26H29ClN6O4S

The compound was prepared from 2-bromo-3'-nitro-4'-chloro-acetophenone (ABCR) and the resin-bound thiourea of Example 21 following the procedure used in Example 23. MS (m+H)+: 557.

Example 79

4-{4-Amino-2-[4-(3-hydroxy-[1,4']bipiperidinyl-1'-yl)-phenylamino]-thiazole-5-carbonyl}-benzoic acid

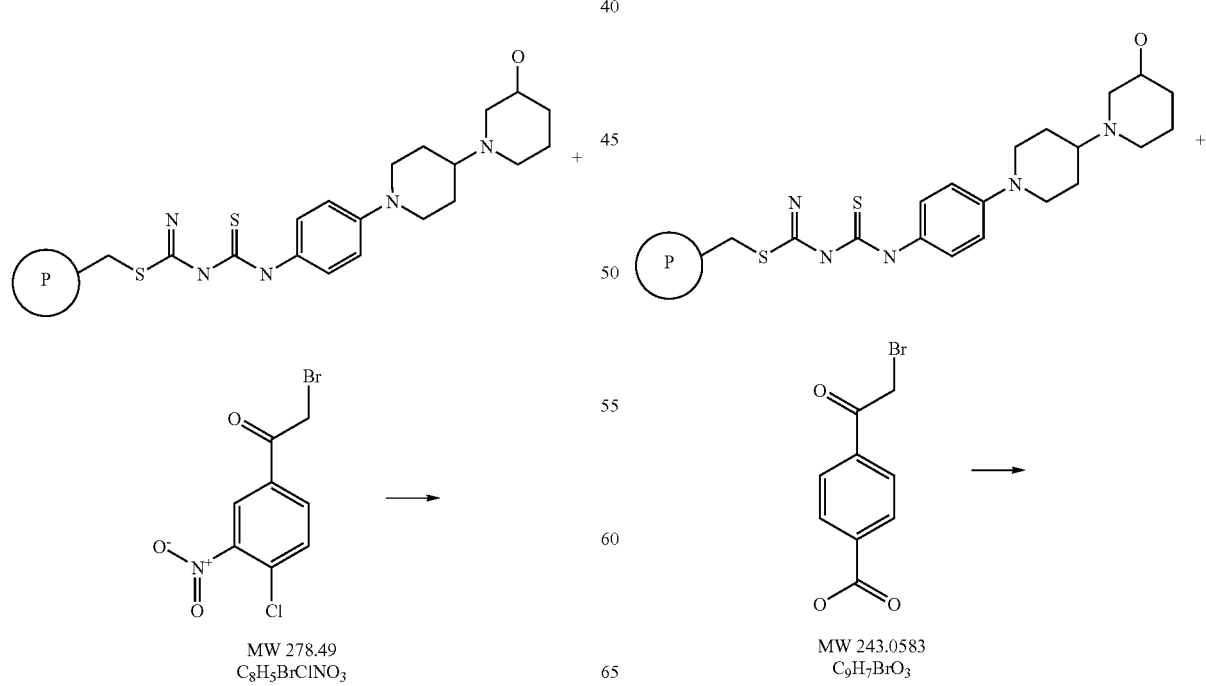

MW 278.49
C8H5BrClNO3

MW 243.0583
C9H7BrO3

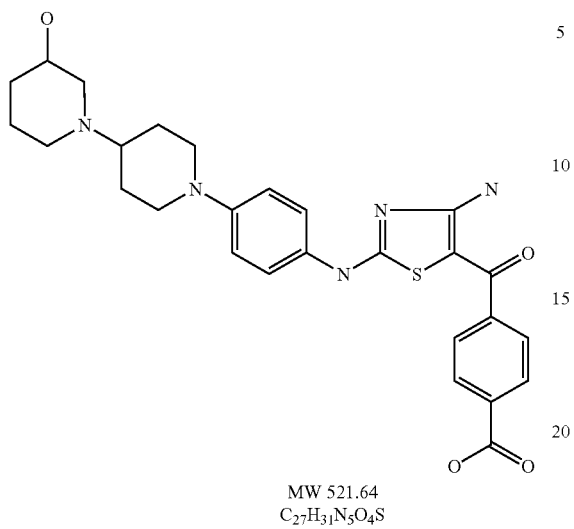

MW 521.64
C27H31N5O4S

The compound was prepared from 2-bromo-3'-nitro-4'-chloro-acetophenone (Oakwood) and the resin-bound thiourea of Example 21 following the procedure used in Example 23. MS (m+H)+: 522.

Example 80

3-{4-Amino-2-[4-(3-hydroxy-[1,4']bipiperidinyl-1'-yl)-phenylamino]-thiazole-5-carbonyl}-benzonitrile

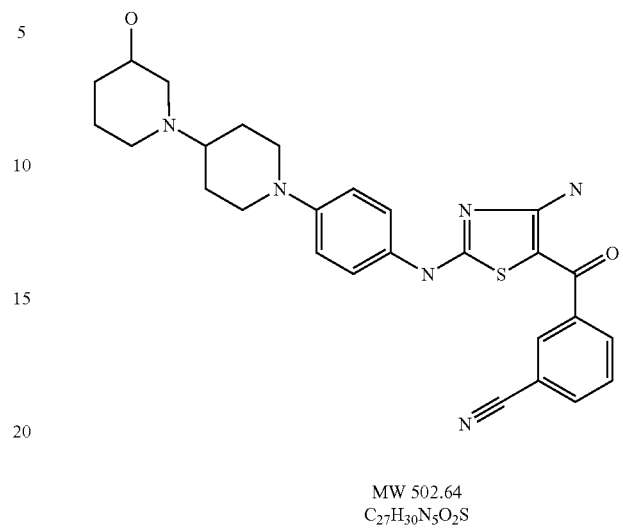

MW 502.64
C27H30N5O2S

The compound was prepared from 2-bromo-4'-cyano-acetophenone (Oakwood) and the resin-bound thiourea of Example 21 following the procedure used in Example 23. MS (m+H)+: 503.

Example 81

{4-Amino-2-[4-(3-hydroxy-[1,4']bipiperidinyl-1'-yl)-phenylamino]-thiazol-5-yl}-(3-hydroxy-phenyl)-methanone

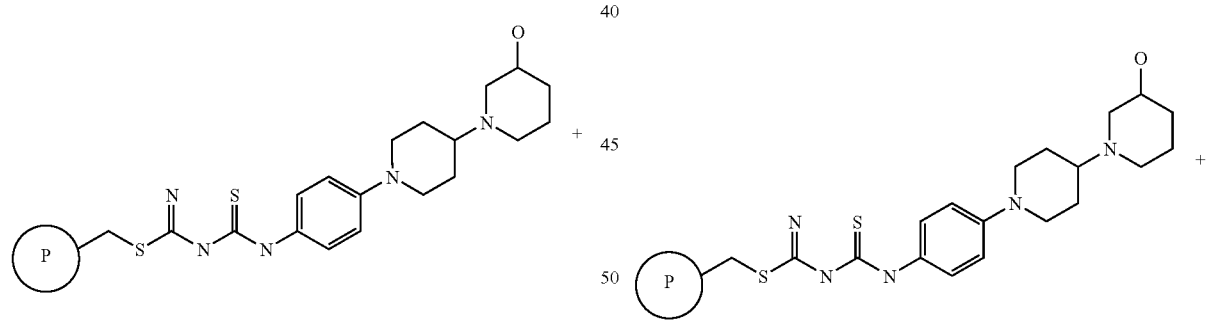

+

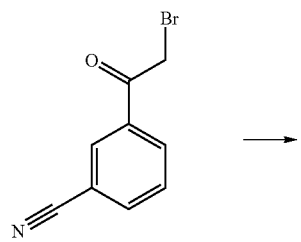

MW 224.0583
C9H6BrNO

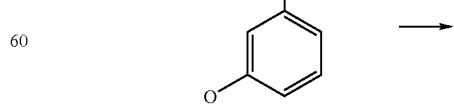

MW 215.05
C8H7BrO2

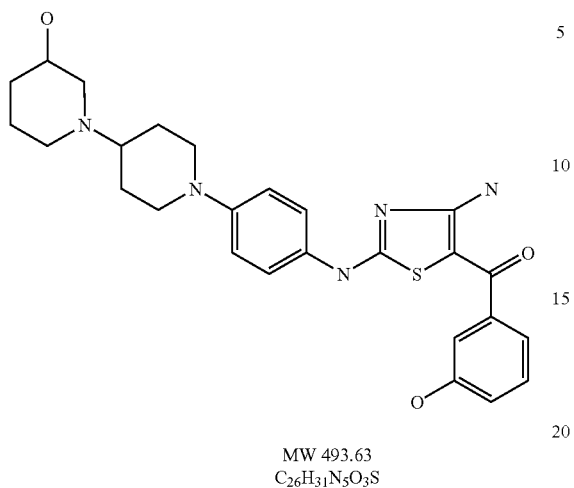

MW 493.63
C<sub>26</sub>H<sub>31</sub>N<sub>5</sub>O<sub>3</sub>S

The compound was prepared from 2-bromo-4'-hydroxy-acetophenone (Oakwood) and the resin-bound thiourea of Example 21 following the procedure used in Example 23. MS (m+H)⁺: 494.

MW 457.55
C<sub>23</sub>H<sub>25</sub>F<sub>2</sub>N<sub>5</sub>OS

The compound was prepared from 2-bromo-3',4'-difluoro-acetophenone (prepared from the procedure described by Chu, Xin-Jie et al, WO2003097048) and the resin-bound thiourea of Example 18 following the procedure used in Example 23. MS (m+H)⁺: 458.

Example 82

{4-Amino-2-[4-(4-dimethylamino-piperidin-1-yl)-phenylamino]-thiazol-5-yl}-(3,5-difluoro-phenyl)-methanone Example 83

{4-Amino-2-[4-(4-dimethylamino-piperidin-1-yl)-phenylamino]-thiazol-5-yl}-(4-chloro-phenyl)-methanone

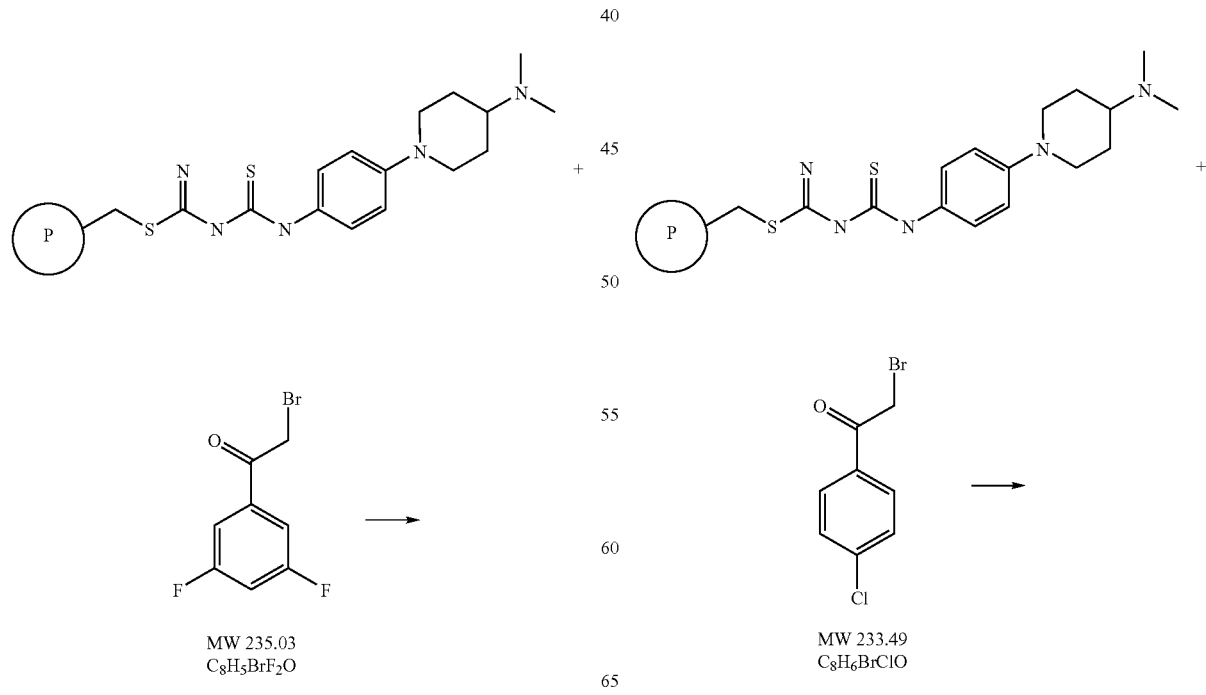

MW 235.03
C<sub>8</sub>H<sub>5</sub>BrF<sub>2</sub>O

MW 233.49
C<sub>8</sub>H<sub>6</sub>BrClO

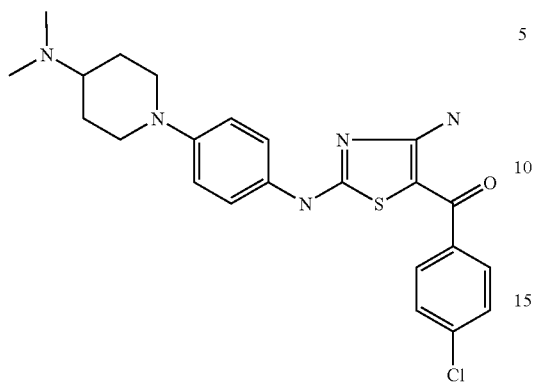

MW 456.01
$C_{23}H_{26}ClN_5OS$

The compound was prepared from 2-bromo-4'-fluoro-acetophenone (ABCR) and the resin-bound thiourea of Example 18 following the procedure used in Example 23. MS (m+H)$^+$: 456.

Example 84

{4-Amino-2-[4-(4-dimethylamino-piperidin-1-yl)-phenylamino]-thiazol-5-yl}-(3,4-difluoro-phenyl)-methanone

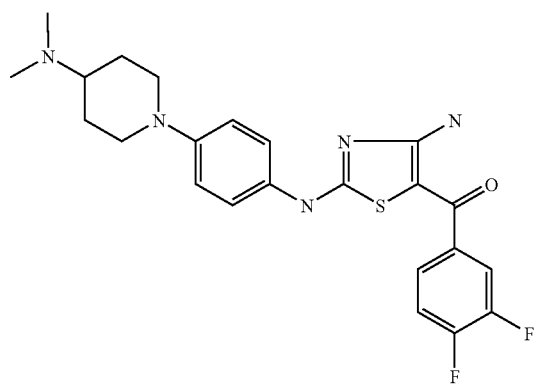

MW 457.55
$C_{23}H_{25}F_2N_5OS$

The compound was prepared from 2-bromo-3',4'-difluoro-acetophenone (ABCR) and the resin-bound thiourea of Example 18 following the procedure used in Example 23. MS (m+H)$^+$: 458.

Example 85

{4-Amino-2-[4-(4-dimethylamino -piperidin-1-yl)-phenylamino]-thiazol-5-yl}-(3,4-dichloro-phenyl)-methanone

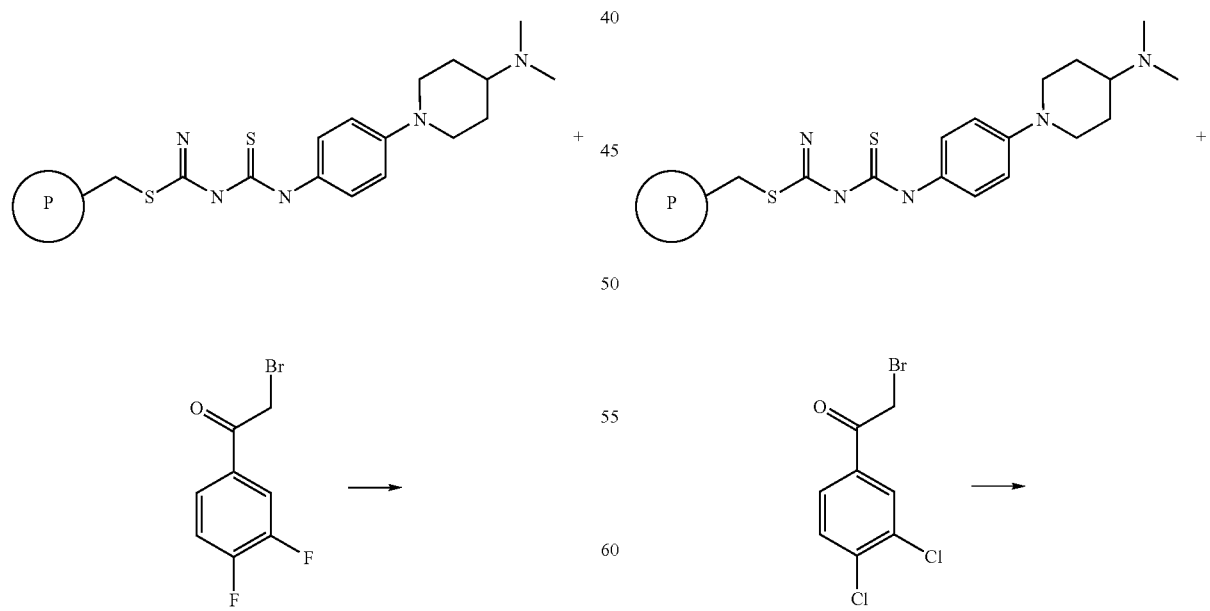

MW 235.03
$C_8H_5BrF_2O$

MW 267.94
$C_8H_5BrCl_2O$

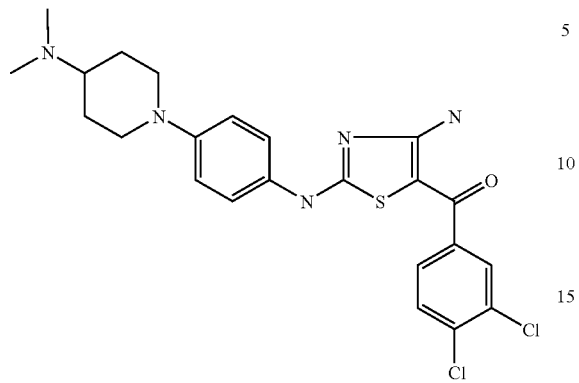

MW 490.46
C₂₃H₂₅Cl₂N₅OS

The compound was prepared from 2-bromo-3',4'-chloro-acetophenone (ABCR) and the resin-bound thiourea of Example 18 following the procedure used in Example 23. MS (m+H)⁺: 490.

Example 86

{4-Amino-2-[4-(4-dimethylamino-piperidin-1-yl)-phenylamino]-thiazol-5-yl}-(4-fluoro-phenyl)-methanone

MW 439.56
C₂₃H₂₆FN₅OS

The compound was prepared from 2-bromo-4'-fluoro-acetophenone (ABCR) and the resin-bound thiourea of Example 18 following the procedure used in Example 23. MS (m+H)⁺: 440.

Example 87

{4-Amino-2-[4-(4-dimethylamino-piperidin-1-yl)-phenylamino]-thiazol-5-yl}-(4-chloro-3-nitro-phenyl)-methanone

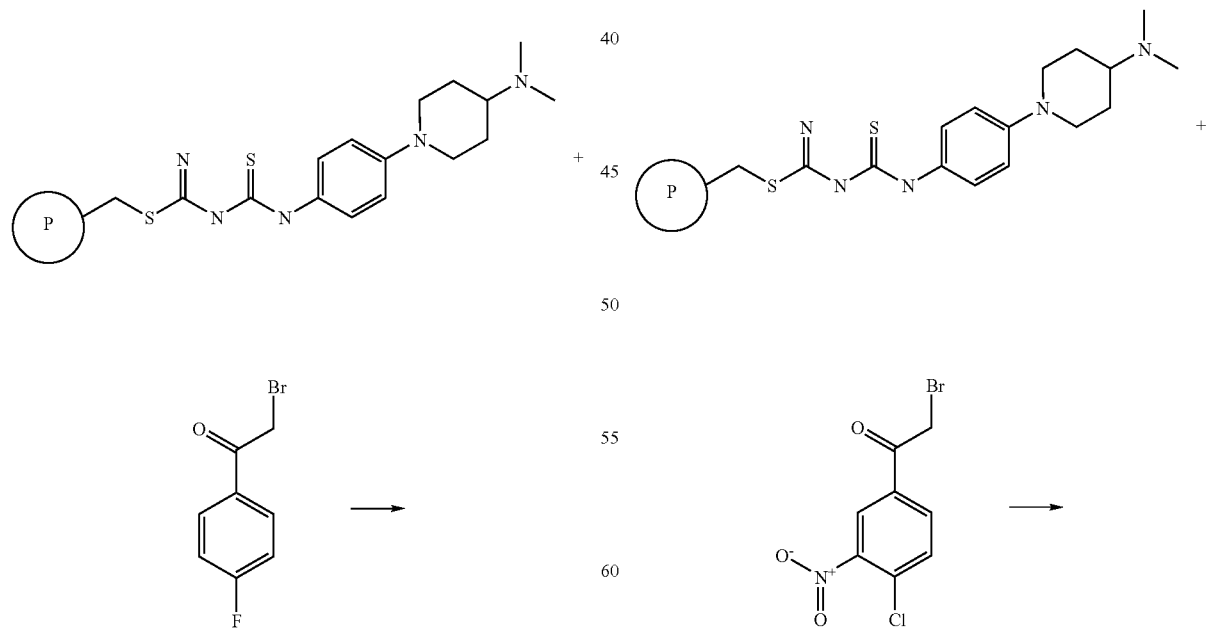

MW 217.0388
C₈H₆BrFO

MW 278.49
C₈H₅BrClNO₃

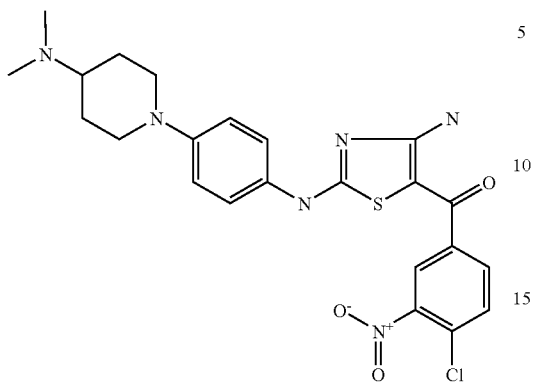

MW 501.01
C23H25ClN6O3S

The compound was prepared from 2-bromo-3'-nitro-4'-chloro-acetophenone (ABCR) and the resin-bound thiourea of Example 18 following the procedure used in Example 23. MS (m+H)+: 501.

Example 88

3-{4-Amino-2-[4-(4-dimethylamino-piperidin-1-yl)-phenylamino]-thiazole-5-carbonyl}-benzonitrile

MW 446.58
C24H26N6OS

The compound was prepared from 2-bromo-4'-cyano-acetophenone (Oakwood) and the resin-bound thiourea of Example 18 following the procedure used in Example 23. MS (m+H)+: 447.

Example 89

[4-Amino-2-(4-[1,4']bipiperidinyl-1'-yl-phenylamino)-thiazol-5-yl]-(3-nitro-phenyl)-methanone

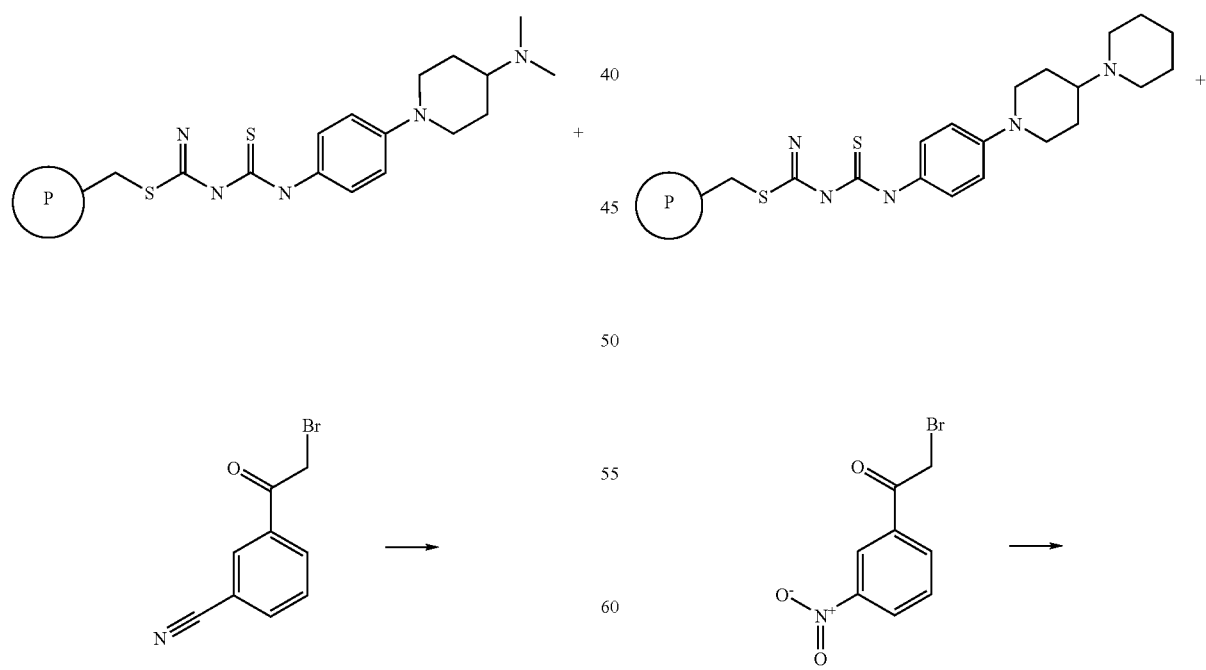

MW 224.0583
C9H6BrN

MW 244.05
C8H5BrNO3

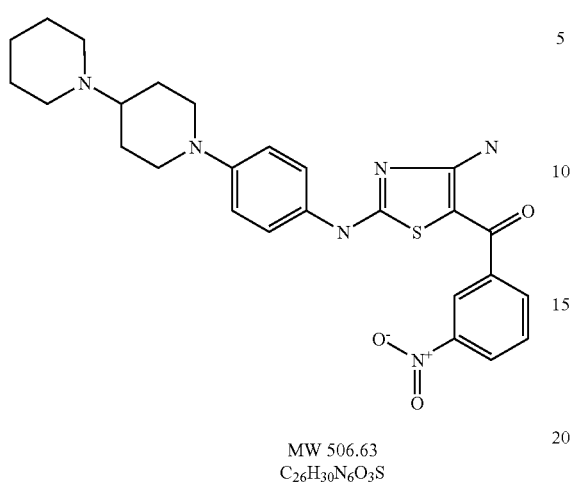

MW 506.63
C<sub>26</sub>H<sub>30</sub>N<sub>6</sub>O<sub>3</sub>S

The compound was prepared from 2-bromo-3'-nitro-acetophenone (Oakwood) and the resin-bound thiourea of Example 19 following the procedure used in Example 23. MS (m+H)$^+$: 507.

Example 90

{4-Amino-2-[4-(4-pyrrolidin-1-yl-piperidin-1-yl)-phenylamino]-thiazol-5-yl}-(3-nitro-phenyl)-methanone

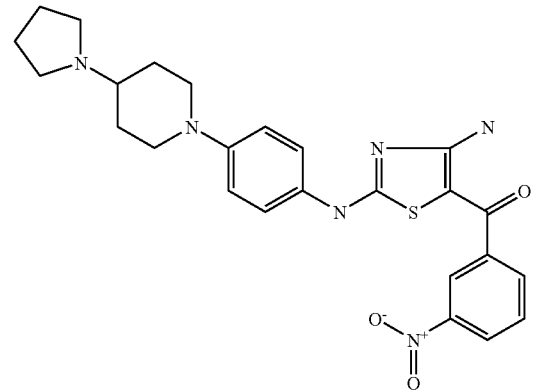

MW 492.60
C<sub>25</sub>H<sub>28</sub>N<sub>6</sub>O<sub>3</sub>S

The compound was prepared from 2-bromo-3'-nitro-acetophenone (Oakwood) and the resin-bound thiourea of Example 20 following the procedure used in Example 23. MS (m+H)$^+$: 493.

Example 91

{4-Amino-2-[4-(3-hydroxy-[1,4']bipiperidinyl-1'-yl)-phenylamino]-thiazol-5-yl}-(3-nitro-phenyl)-methanone

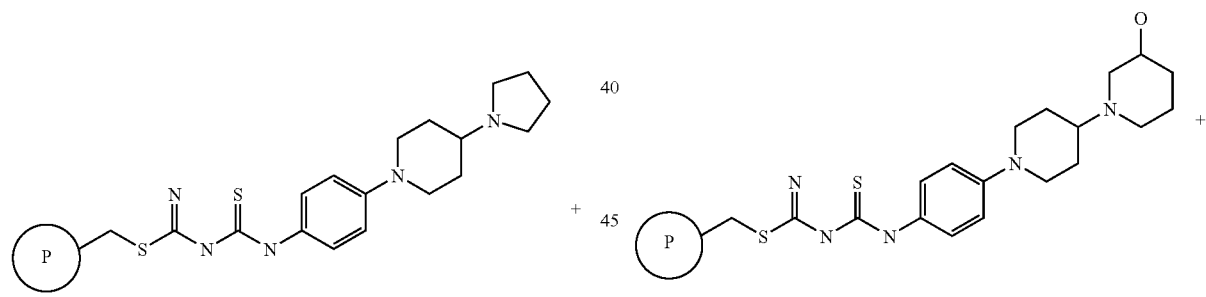

+

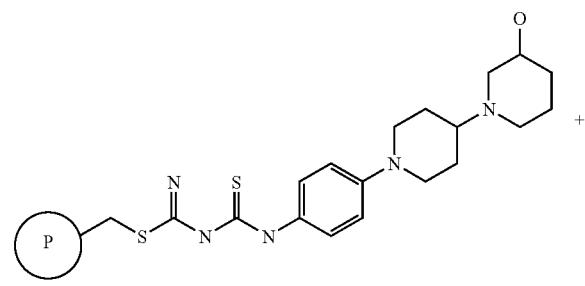

+

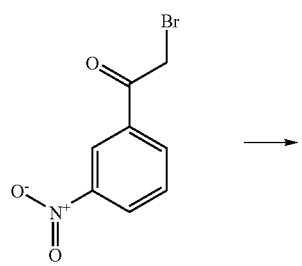

MW 244.05
C<sub>8</sub>H<sub>6</sub>BrNO<sub>3</sub>

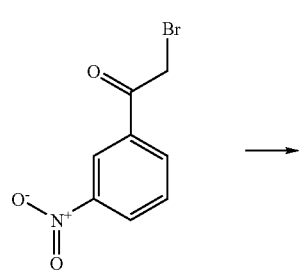

MW 244.05
C<sub>8</sub>H<sub>6</sub>BrNO<sub>3</sub>

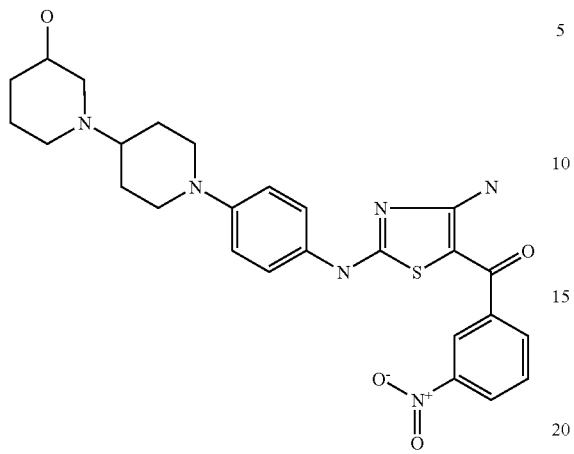

MW 522.63
C26H30N6O4S

The compound was prepared from 2-bromo-3'-nitro-acetophenone (Oakwood) and the resin-bound thiourea of Example 21 following the procedure used in Example 23. MS (m+H)+: 523.

Example 92

{4-Amino-2-[4-(4-dimethylamino-piperidin-1-yl)-phenylamino]-thiazol-5-yl}-(3-nitro-phenyl)-methanone

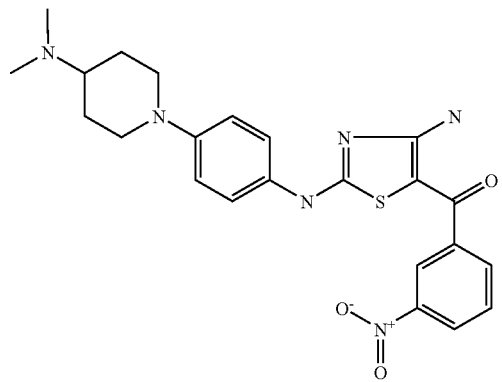

MW 466.57
C23H26N6O3S

The compound was prepared from 2-bromo-3'-nitro-acetophenone (Oakwood) and the resin-bound thiourea of Example 18 following the procedure used in Example 23. MS (m+H)+: 467.

Example 93

5-{4-Amino-2-[4-(4-dimethylamino-piperidin-1-yl)-phenylamino]-thiazole-5-carbonyl}-2-hydroxy-benzamide

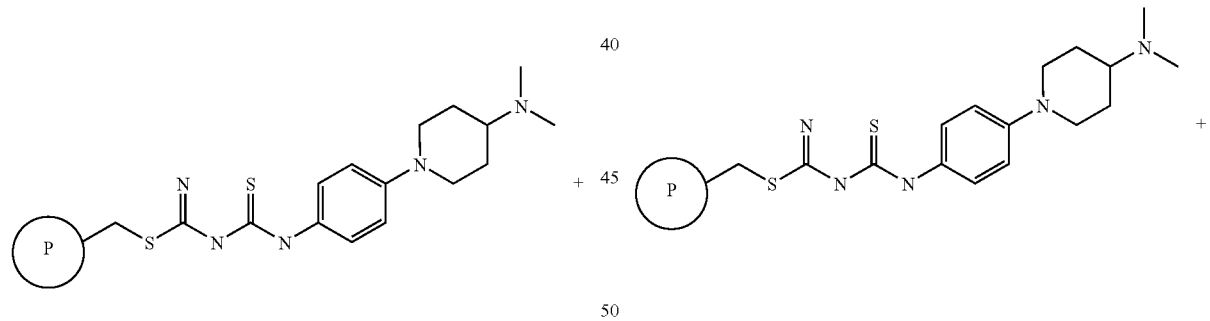

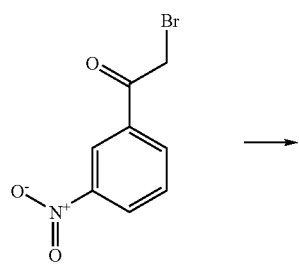

MW 244.05
C8H6BrNO3

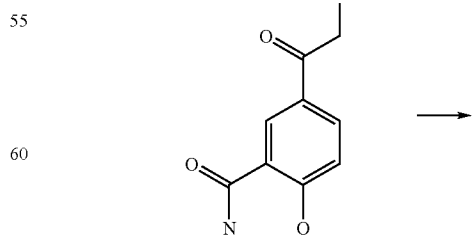

MW 258.07
C9H8BrNO3

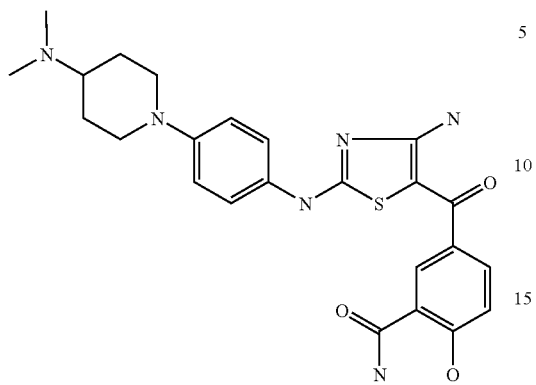

MW 480.59
C₂₄H₂₈N₆O₃S

The compound was prepared from 5-(2-bromo-acetyl)-2-hydroxy-benzamide (ABCR) and the resin-bound thiourea of Example 18 following the procedure used in Example 23. MS (m+H)⁺: 481.

Example 94

5-{4-Amino-2-[4-(4-pyrrolidin-1-yl-piperidin-1-yl)-phenylamino]-thiazole-5-carbonyl}-2-hydroxy-benzamide

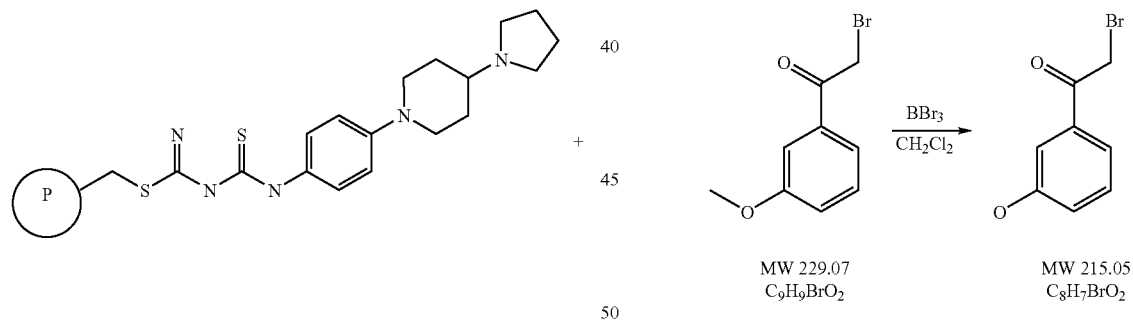

MW 258.07
C₉H₈BrNO₃

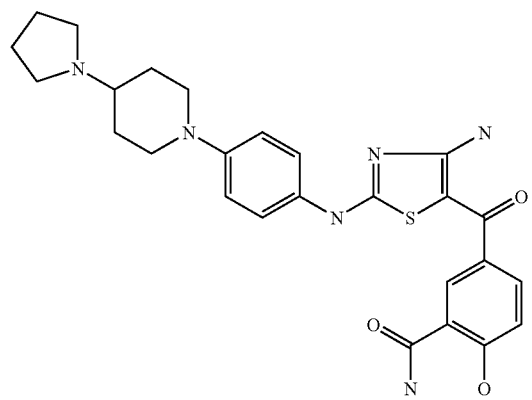

MW 506.63
C₂₆H₃₀N₆O₃S

The compound was prepared from 5-(2-bromo-acetyl)-2-hydroxy-benzamide (ABCR) and the resin-bound thiourea of Example 20 following the procedure used in Example 23. MS (m+H)⁺: 507.

Example 95

2-Bromo-1-(3-hydroxy-phenyl)-ethanone

To a stirred solution of 2-bromo-1-(3-methoxy-phenyl)-ethanone (Aldrich, 3.44 g, 15 mmol) in methylene chloride (20 mL) at −10° C., boron tribromide (Aldrich, 16.5 mmol, 1M solution in CH2Cl2, 16.5 mL) was added slowly and the mixture was stirred for 1.5 hours. The reaction was quenched with ice water and the organic layer was separated. The aqueous layer was extracted with EtOAc and the extracts were combined and dried with sodium sulfate. Removal of solvent gave a greenish solid which was purified by chromatography (EtOAc/Hexane, 25%) gave an off-white solid. 770 mg, 24%. The compound was used directly for the next step.

Example 96

{4-Amino-2-[4-(4-pyrrolidin-1-yl-piperidin-1-yl)-phenylamino]-thiazol-5-yl}-(3-hydroxy-phenyl)-methanone

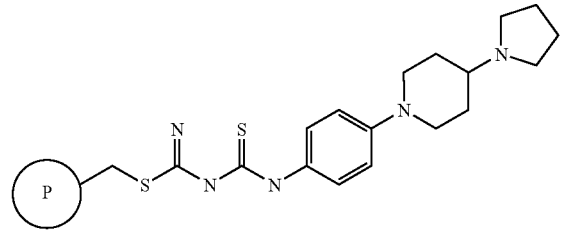

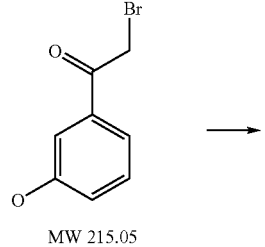

MW 215.05
C$_8$H$_7$BrO$_2$

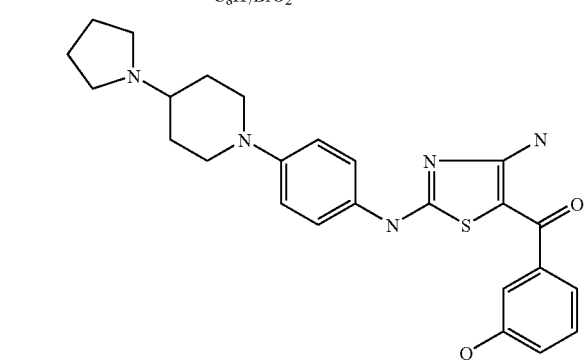

MW 463.61
C$_{25}$H$_{29}$N$_5$O$_2$S

The compound was prepared from 2-bromo-3'-hydroxy-acetophenone (Example 95) and the resin-bound thiourea of Example 20 following the procedure used in Example 23. MS (m+H)$^+$: 464.

Example 97

{4-Amino-2-[4-(4-pyrrolidin-1-yl-piperidin-1-yl)-phenylamino]-thiazol-5-yl}-(3-hydroxy-phenyl)-methanone

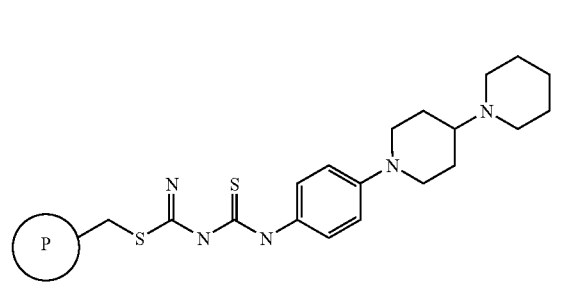

-continued

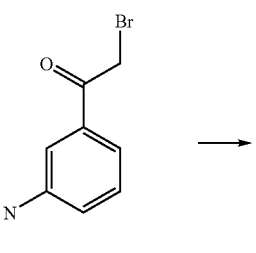

MW 214.06
C$_8$H$_8$BrNO

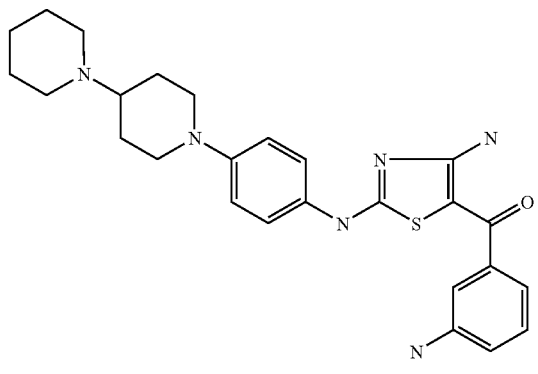

MW 476.65
C$_{26}$H$_{32}$N$_6$OS

The compound was prepared from 2-bromo-3'-amino-acetophenone (made though the procedure from Zhang, M. Q., Journal of Heterocycle Chemistry, 1991, 28(3), 673–683) and the resin-bound thiourea of Example 19 following the procedure used in Example 23. MS (m+H)$^+$: 477.

Example 98

{4-Amino-2-[4-(4-morpholin-4-yl-piperidin-1-yl)-phenylamino]-thiazol-5-yl}-(2,3-dihydro-benzo[1,4]dioxin-6-yl)-methanone

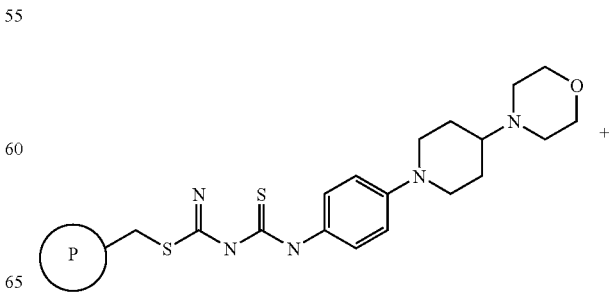

-continued

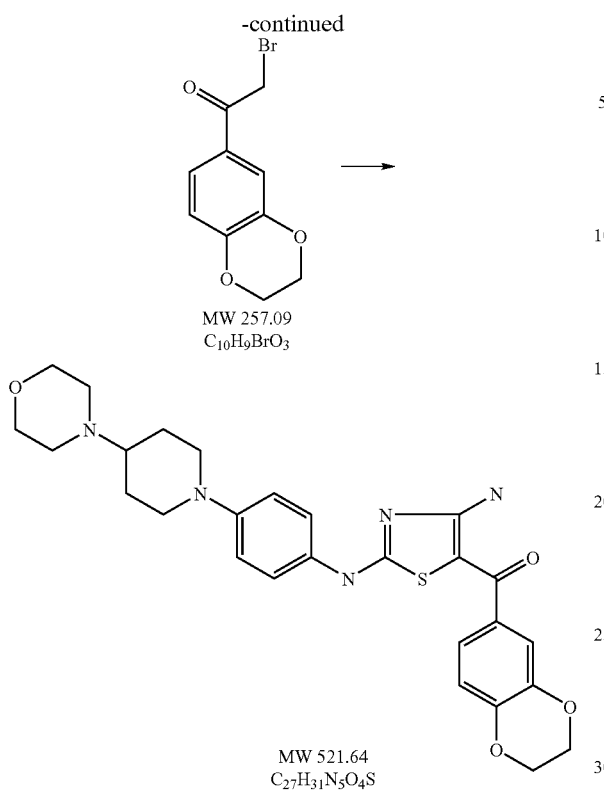

The compound was prepared from 2-bromo-1-(2,3-dihydro-benzo[1,4]dioxin-6-yl)-ethanone (Maybridge International) and the resin-bound thiourea of Example 22 following the procedure used in Example 23. MS (m+H)$^+$: 522.

Example 99

{4-Amino-2-[4-(4-morpholin-4-yl-piperidin-1-yl)-phenylamino]-thiazol-5-yl}-(3-fluoro-phenyl)-methanone

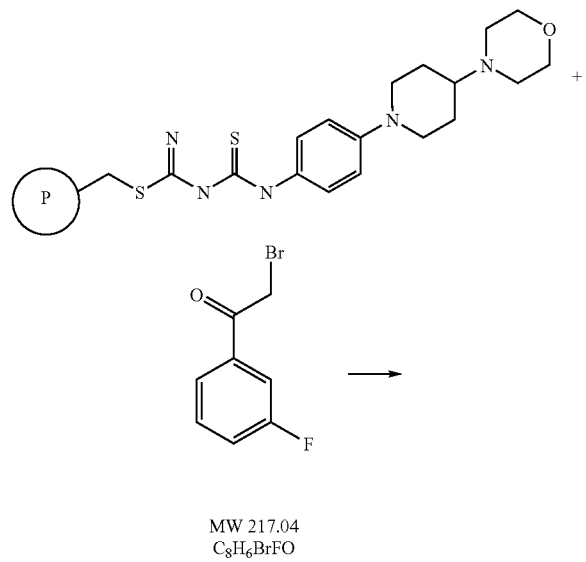

-continued

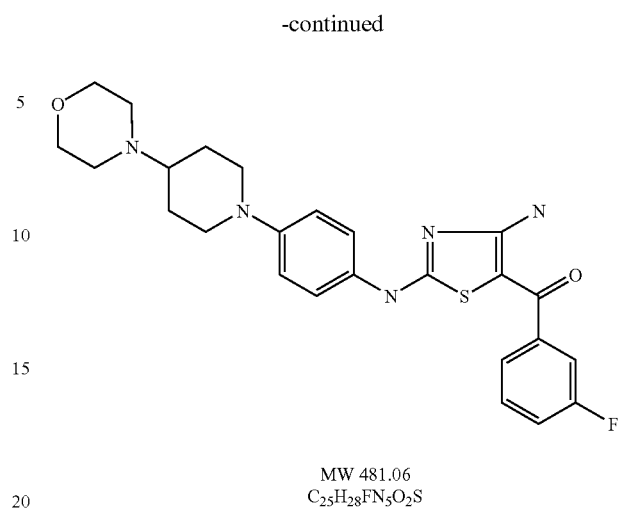

The compound was prepared from 3-fluorophenylacyl bromide (Maybridge International) and the resin-bound thiourea of Example 22 following the procedure used in Example 23. MS (m+H)$^+$: 482.

Example 100

{4-Amino-2-[4-(4-morpholin-4-yl-piperidin-1-yl)-phenylamino]-thiazol-5-yl}-(3-fluoro-4-methoxy-phenyl)-methanone

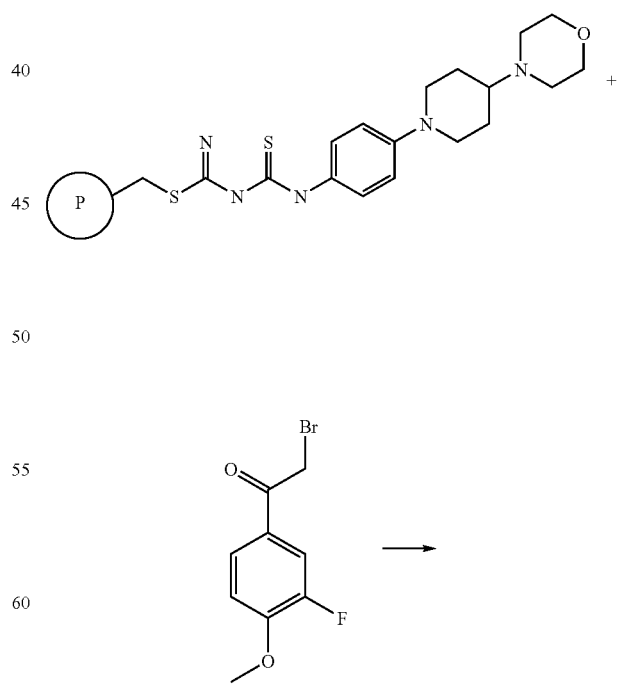

111

-continued

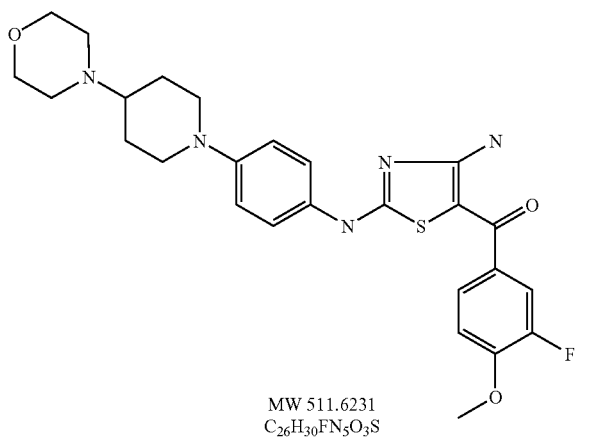

MW 511.6231
$C_{26}H_{30}FN_5O_3S$

The compound was prepared from 1'-bromo 3-fluoro-4-methoxy acetophenone (Chu et al. WO2003097048) and the resin-bound thiourea of Example 22 following the procedure used in Example 23. MS (m+H)+: 512.

Example 101

{4-Amino-2-[4-(4-morpholin-4-yl-piperidin-1-yl)-phenylamino]-thiazol-5-yl}-benzo[1,3]dioxol-5-yl-methanone

112

-continued

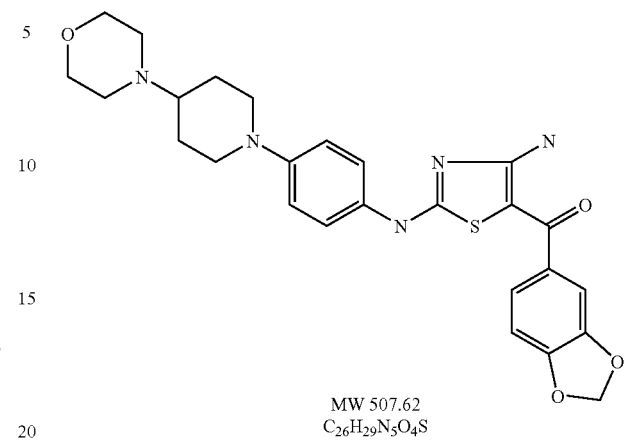

MW 507.62
$C_{26}H_{29}N_5O_4S$

The compound was prepared from 1-benzo[1,3]dioxol-5-yl-2-bromo-ethanone (Maybridge International) and the resin-bound thiourea of Example 22 following the procedure used in Example 23. MS (m+H)+: 508.

Example 102

{4-Amino-2-[4-(4-morpholin-4-yl-piperidin-1-yl)-phenylamino]-thiazol-5-yl}-(3-methoxy-phenyl)-methanone

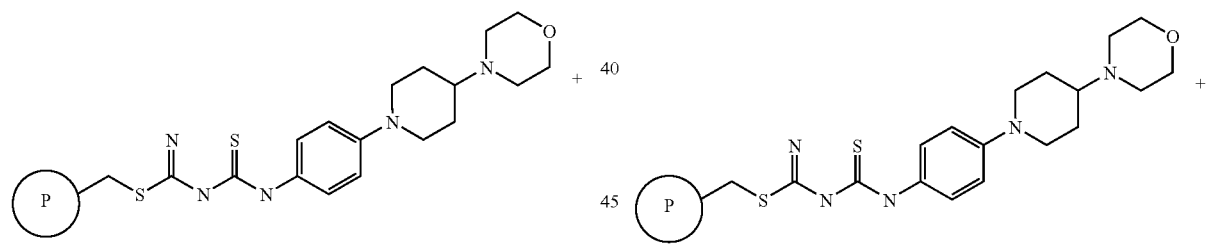

+

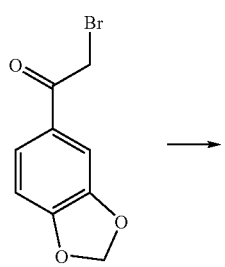

MW 243.06
$C_9H_7BrO_3$

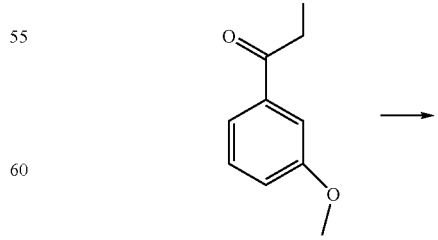

MW 243.06
$C_9H_7BrO_3$

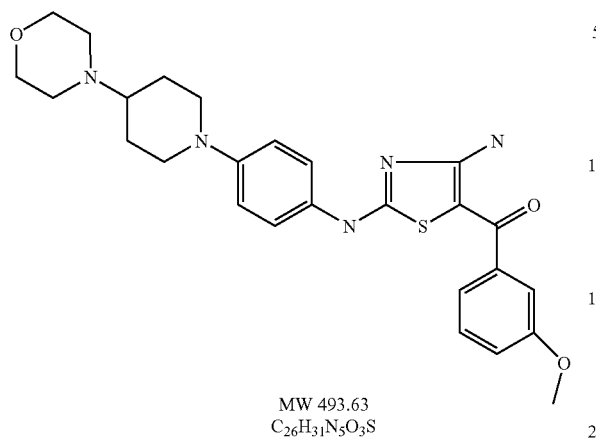

MW 493.63
C$_{26}$H$_{31}$N$_5$O$_3$S

The compound was prepared from 2-bromo-3'-methoxy-acetophenone (Aldrich) and the resin-bound thiourea of Example 22 following the procedure used in Example 23. MS (m+H)$^+$: 494.

Example 103

{4-Amino-2-[4-(4-morpholin-4-yl-piperidin-1-yl)-phenylamino]-thiazol-5-yl}-(3-hydroxy-phenyl)-methanone

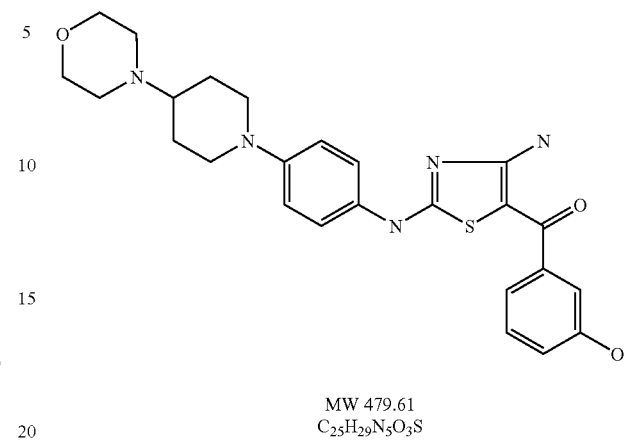

MW 479.61
C$_{25}$H$_{29}$N$_5$O$_3$S

The compound was prepared from 2-bromo-3'-hydroxy-acetophenone (Example 95) and the resin-bound thiourea of Example 22 following the procedure used in Example 23. MS (m+H)$^+$: 480.

Example 104

3-{4-Amino-2-[4-(4-morpholin-4-yl-piperidin-1-yl)-phenylamino]-thiazole-5-carbonyl}-benzonitrile

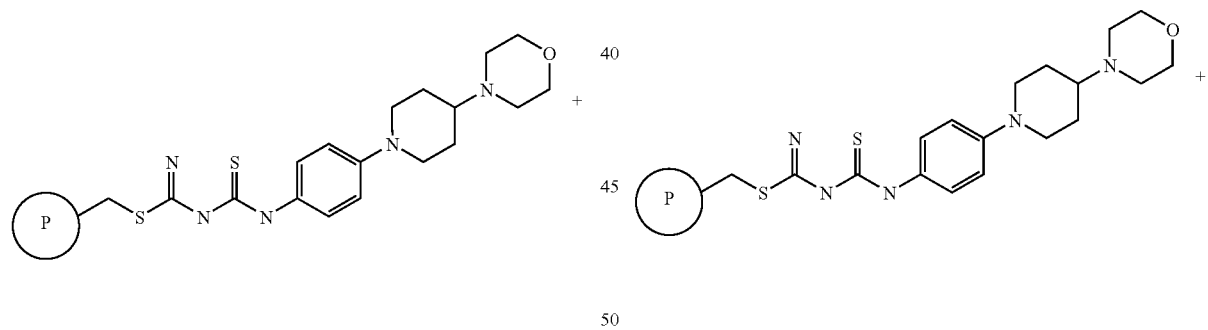

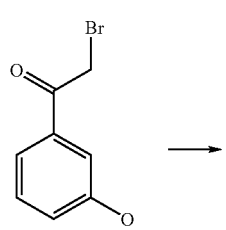

MW 243.06
C$_9$H$_7$BrO$_3$

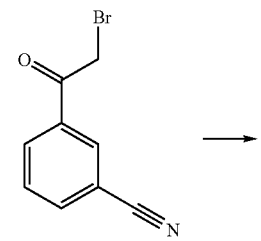

MW 224.06
C$_9$H$_6$BrNO

115

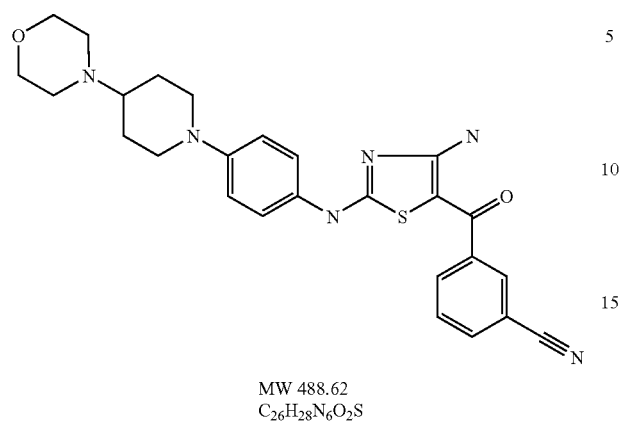

MW 488.62
C26H28N6O2S

The compound was prepared from 2-bromo-3'-cyano-acetophenone (Oakwood) and the resin-bound thiourea of Example 22 following the procedure used in Example 23. MS (m+H)+: 489.

Example 105

{4-Amino-2-[4-(4-morpholin-4-yl-piperidin-1-yl)-phenylamino]-thiazol-5-yl}-(3-nitro-phenyl)-methanone

116

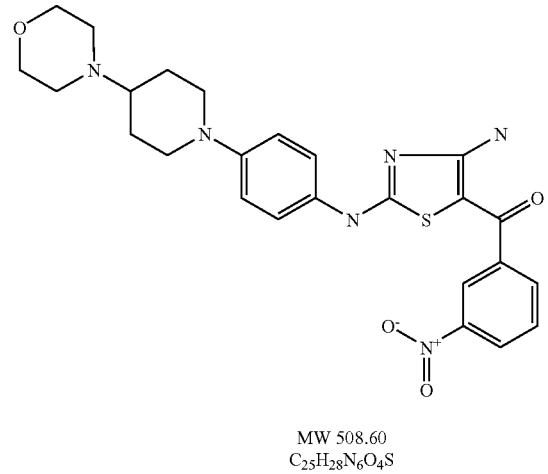

MW 508.60
C25H28N6O4S

The compound was prepared from 2-bromo-3'-nitro-acetophenone (Oakwood) and the resin-bound thiourea of Example 22 following the procedure used in Example 23. MS (m+H)+: 509.

Example 106

{4-Amino-2-[4-(4-morpholin-4-yl-piperidin-1-yl)-phenylamino]-thiazol-5-yl}-(4-methoxy-3-nitro-phenyl)-methanone

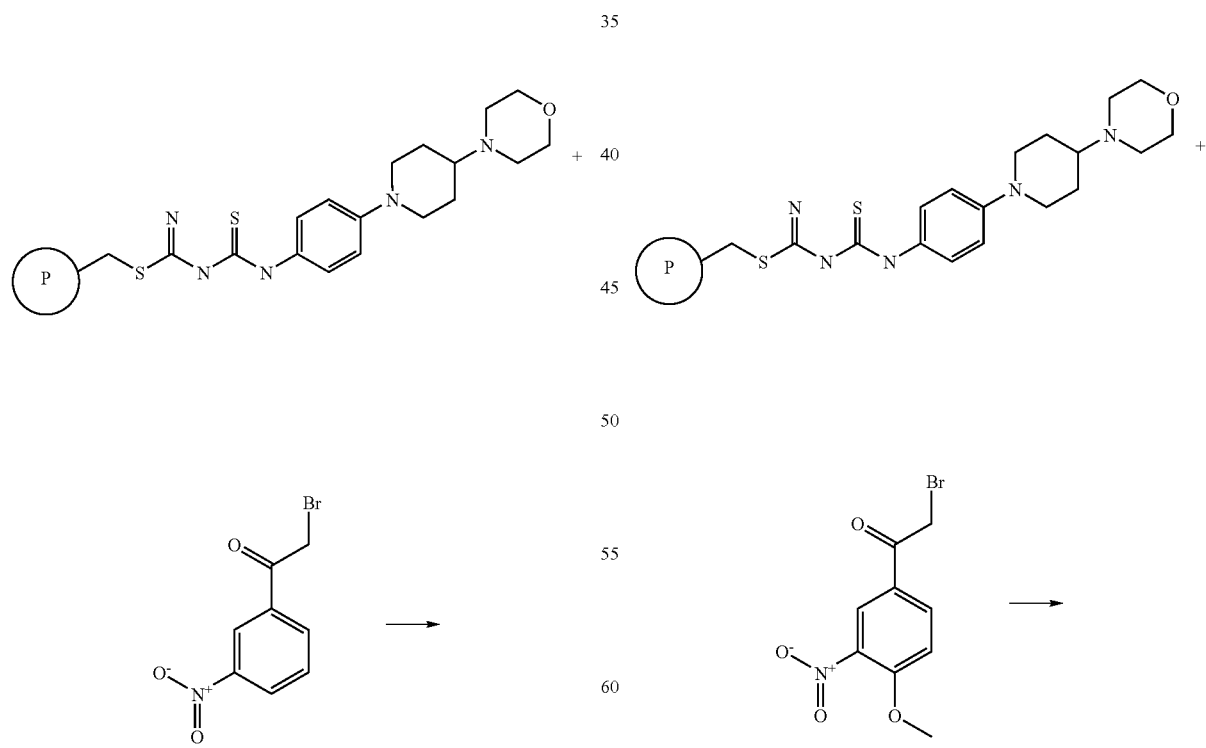

MW 244.05
C8H6BrNO3

MW 274.07
C9H8BrNO4

117

-continued

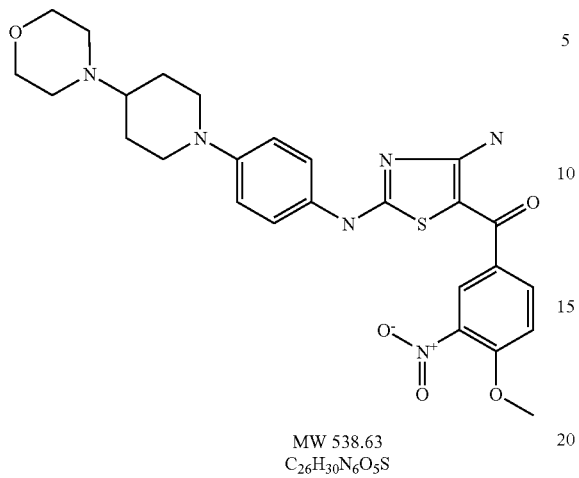

MW 538.63
C$_{26}$H$_{30}$N$_6$O$_5$S

The compound was prepared from 2-bromo-3'-nitro-4'-methoxy-acetophenone (Prepared according to Nam, Nguyen-Hai et al, Bioorganic & Medicinal Chemistry Letters, 2001, 11(23), 3073–3076) and the resin-bound thiourea of Example 22 following the procedure used in Example 23. MS (m+H)$^+$: 539.

Example 107

{4-Amino-2-[4-(4-pyrrolidin-1-yl-piperidin-1-yl)-phenylamino]-thiazol-5-yl}-(4-methoxy-3-nitro-phenyl)-methanone

118

-continued

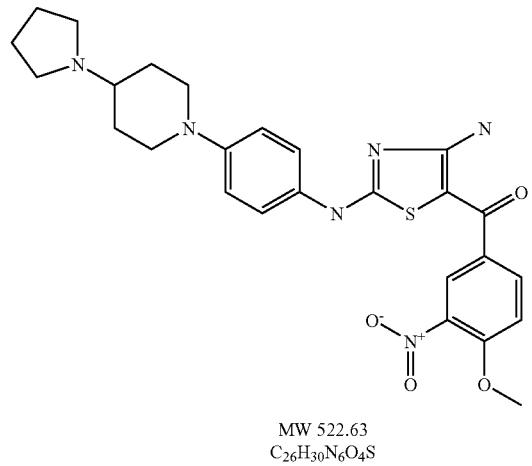

MW 522.63
C$_{26}$H$_{30}$N$_6$O$_4$S

The compound was prepared from 2-bromo-3'-nitro-4'-methoxy-acetophenone (Prepared according to Nam, Nguyen-Hai et al, Bioorganic & Medicinal Chemistry Letters, 2001, 11(23), 3073–3076) and the resin-bound thiourea of Example 20 following the procedure used in Example 23. MS (m+H)$^+$: 523.

Example 108

[4-Amino-2-(4-[1,4']bipiperidinyl-1'-yl-phenylamino)-thiazol-5-yl]-(4-methoxy-3-nitro-phenyl)-methanone

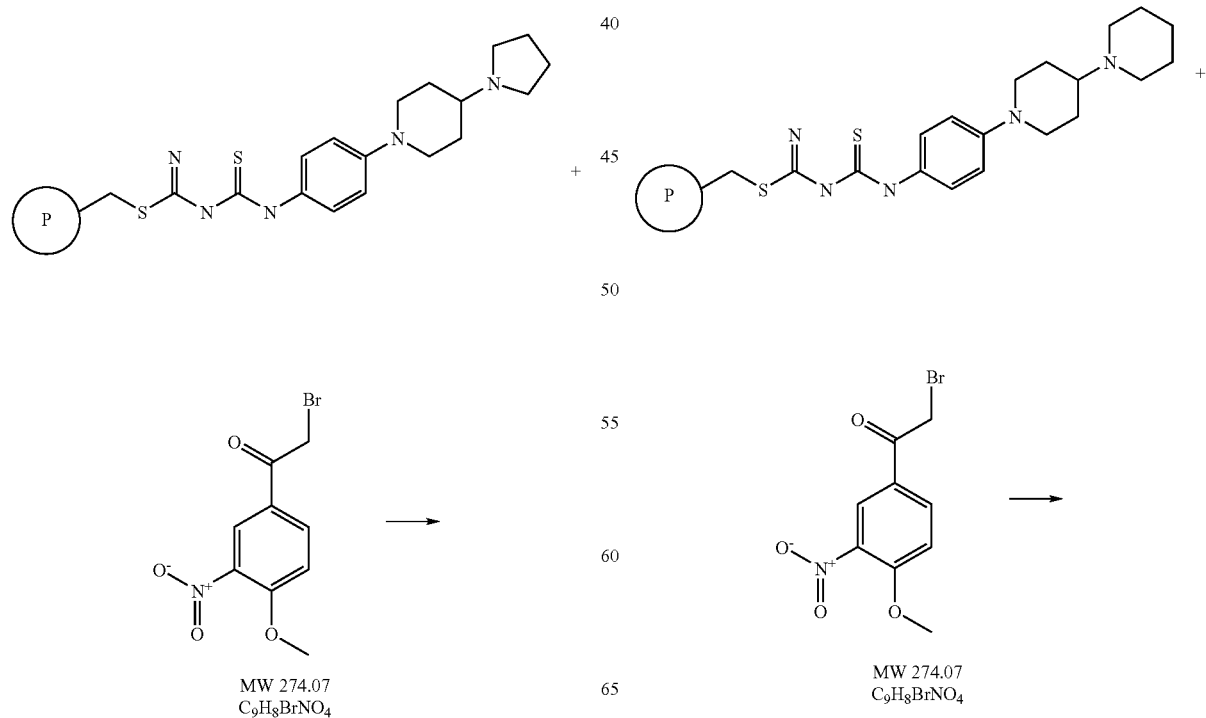

MW 274.07
C$_9$H$_8$BrNO$_4$

MW 274.07
C$_9$H$_8$BrNO$_4$

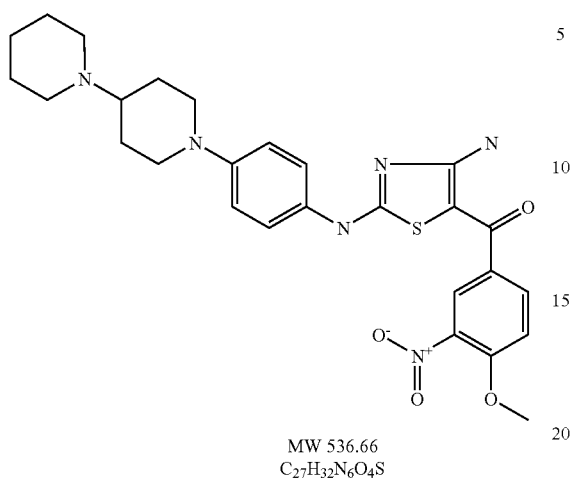

MW 536.66
C27H32N6O4S

The compound was prepared from 2-bromo-3'-nitro-4'-methoxy-acetophenone (Prepared according to Nam, Nguyen-Hai et al, Bioorganic & Medicinal Chemistry Letters, 2001, 11(23), 3073–3076) and the resin-bound thiourea of Example 19 following the procedure used in Example 23. MS (m+H)+: 537.

Example 109

{4-Amino-2-[4-(4-pyrrolidin-1-yl-piperidin-1-yl)-phenylamino]-thiazol-5-yl}-tolyl-methanone

MW 461.63
C26H31N5OS

The compound was prepared from 2-bromo-3'-methyl-acetophenone (Prepared according to Chu, Xin-jie et al, WO2003097048) and the resin-bound thiourea of Example 20 following the procedure used in Example 23. MS (m+H)+: 462.

Example 110

{4-Amino-2-[4-(4-dimethylamino-piperidin-1-yl)-phenylamino]-thiazol-5-yl}-tolyl-methanone

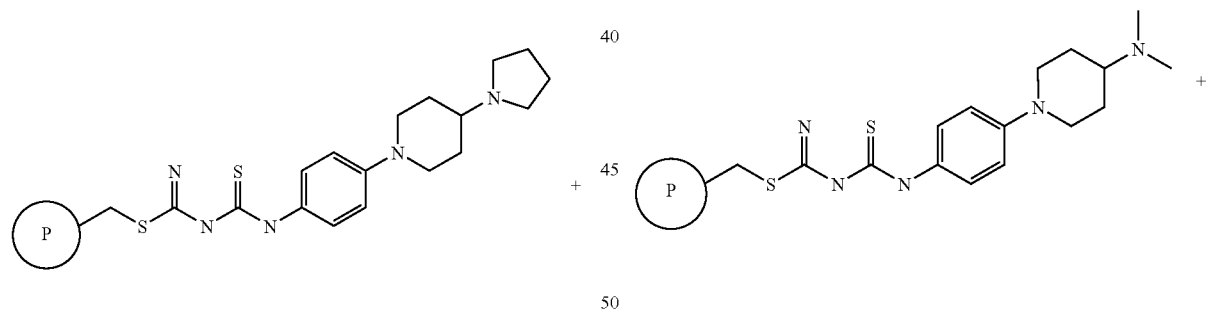

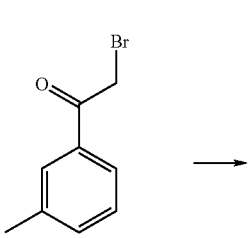

MW 213.08
C9H9BrO

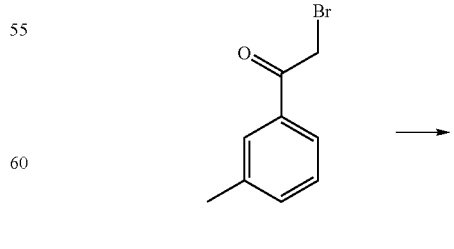

MW 213.08
C9H9BrO

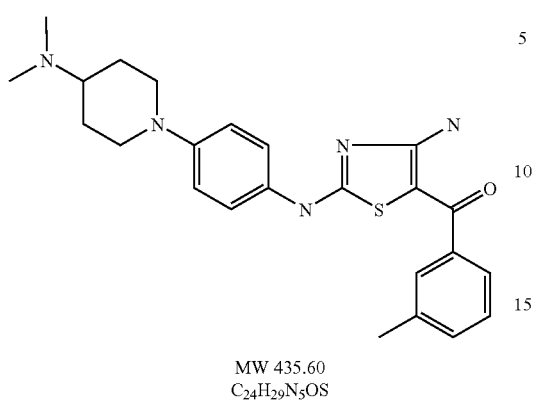

MW 435.60
C24H29N5OS

The compound was prepared from 2-bromo-3'-methyl-acetophenone (Prepared according to Chu, Xin-jie et al, WO2003097048) and the resin-bound thiourea of Example 18 following the procedure used in Example 23. MS (m+H)+: 436.

Example 111

[4-Amino-2-(4-[1,4']bipiperidinyl-1'-yl-phenylamino)-thiazol-5-yl]-tolyl-methanone

MW 475.66
C27H33N5OS

The compound was prepared from 2-bromo-3'-methyl-acetophenone (Prepared according to Chu, Xin-jie et al, WO2003097048) and the resin-bound thiourea of Example 19 following the procedure used in Example 23. MS (m+H)+: 476.

Example 112

{4-Amino-2-[4-(4-morpholin-4-yl-piperidin-1-yl)-phenylamino]-thiazol-5-yl}-tolyl-methanone, compound with hydrobromide

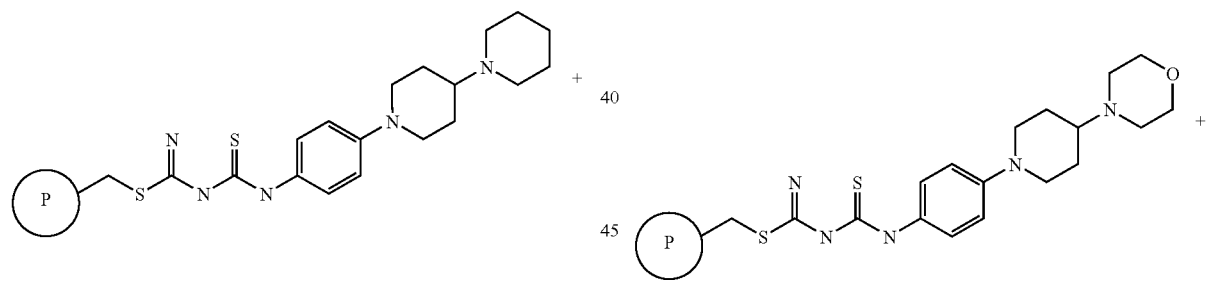

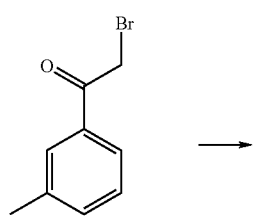

MW 213.08
C9H9BrO

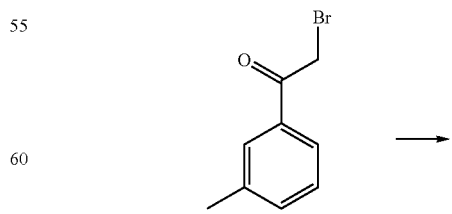

MW 213.08
C9H9BrO

-continued

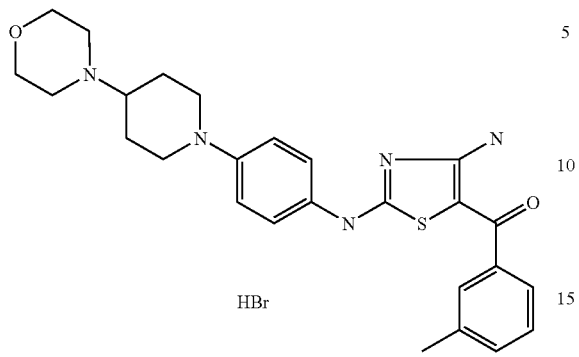

MW 477.63 + 81
C₂₅H₃₁N₅O₂S + HBr

The compound was prepared from 2-bromo-3'-methyl-acetophenone (Prepared according to Chu, Xin-jie et al, WO2003097048) and the resin-bound thiourea of Example 22 following the procedure used in Example 23. MS (m+H)$^+$: 478.

Example 113

{4-Amino-2-[4-(4-dimethylamino-piperidin-1-yl)-phenylamino]-thiazol-5-yl}-(4-methoxy-3-nitro-phenyl)-methanone -continued

MW 496.59
C₂₄H₂₈N₆O₄S

The compound was prepared from 2-bromo-3'-nitro-4'-methoxy-acetophenone (Prepared according to Nam, Nguyen-Hai et al, Bioorganic & Medicinal Chemistry Letters, 2001, 11(23), 3073–3076) and the resin-bound thiourea of Example 18 following the procedure used in Example 23. MS (m+H)$^+$: 497.

Example 114

{4-Amino-2-[4-(4-pyrrolidin-1-yl-piperidin-1-yl)-phenylamino]-thiazol-5-yl}-(3-ethyl-phenyl)-methanone

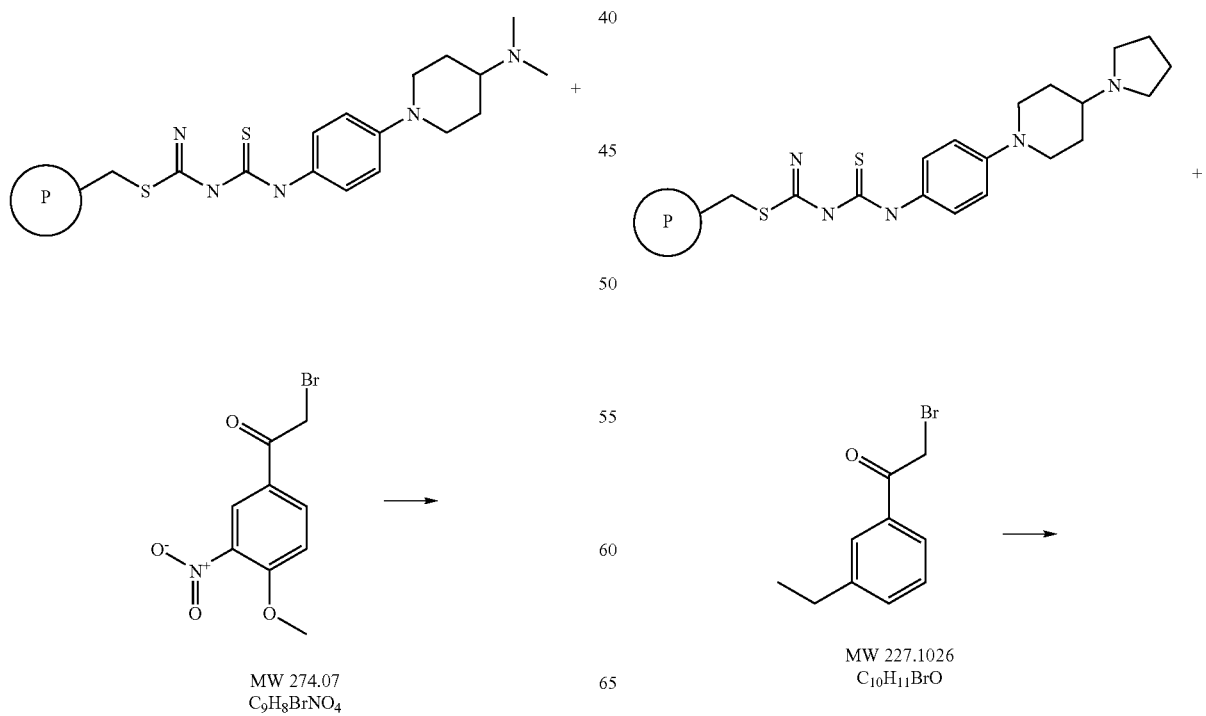

MW 274.07
C₉H₈BrNO₄

MW 227.1026
C₁₀H₁₁BrO

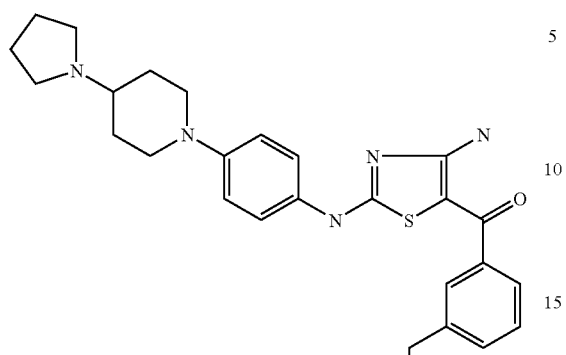

MW 475.66
C27H33N5OS

The compound was prepared from 2-bromo-3'-ethyl-acetophenone (Prepared according to Chu, Xin-jie et al, WO2003097048) and the resin-bound thiourea of Example 20 following the procedure used in Example 23. MS (m+H)+: 476.

Example 115

{4-Amino-2-[4-(4-dimethylamino-piperidin-1-yl)-phenylamino]-thiazol-5-yl}-(3-ethyl-phenyl)-methanone

MW 449.62
C25H31N5OS

The compound was prepared from 2-bromo-3'-ethyl-acetophenone (Prepared according to Chu, Xin-jie et al, WO2003097048) and the resin-bound thiourea of Example 18 following the procedure used in Example 23. MS (m+H)+: 450.

Example 116

{4-Amino-2-[4-(4-morpholin-4-yl-piperidin-1-yl)-phenylamino]-thiazol-5-yl}-(3-ethyl-phenyl)-methanone

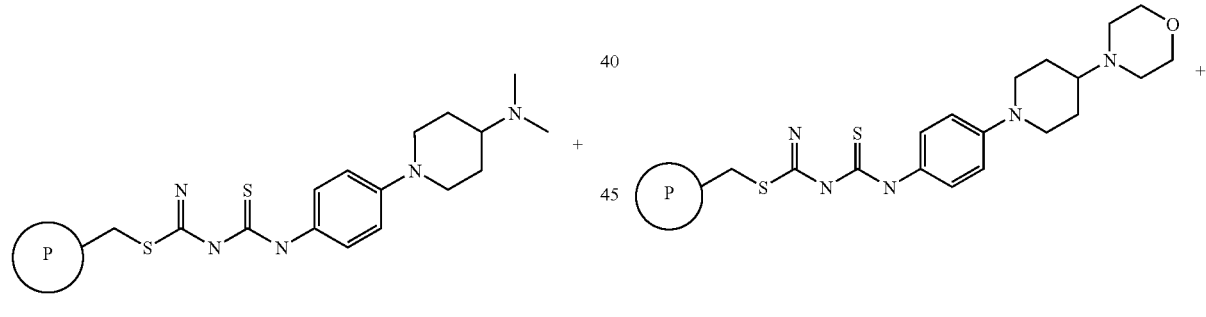

MW 227.1026
C10H11BrO

MW 227.1026
C10H11BrO

127

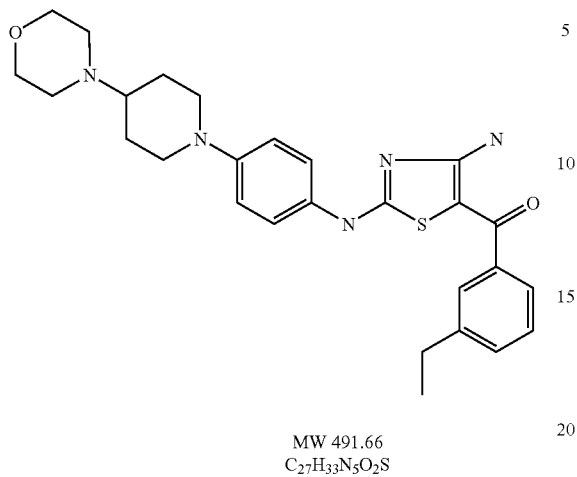

MW 491.66
$C_{27}H_{33}N_5O_2S$

The compound was prepared from 2-bromo-3'-ethyl-acetophenone (Prepared according to Chu, Xin-jie et al, WO2003097048) and the resin-bound thiourea of Example 22 following the procedure used in Example 23. MS (m+H)$^+$: 492.

Example 117

[4-Amino-2-(4-[1,4']bipiperidinyl-1'-yl-phenylamino)-thiazol-5-yl]-(3-ethyl-phenyl)-methanone

128

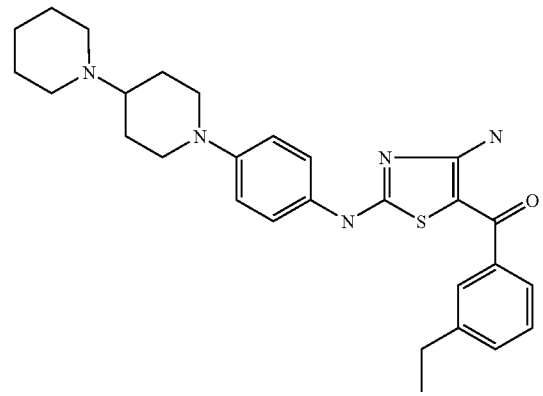

MW 489.69
$C_{28}H_{35}N_5OS$

The compound was prepared from 2-bromo-3'-ethyl-acetophenone (Prepared according to Chu, Xin-jie et al, WO2003097048) and the resin-bound thiourea of Example 19 following the procedure used in Example 23. MS (m+H)$^+$: 490.

Example 118

{4-Amino-2-[4-(4-pyrrolidin-1-yl-piperidin-1-yl)-phenylamino]-thiazol-5-yl}-(3-ethoxy-phenyl)-methanone

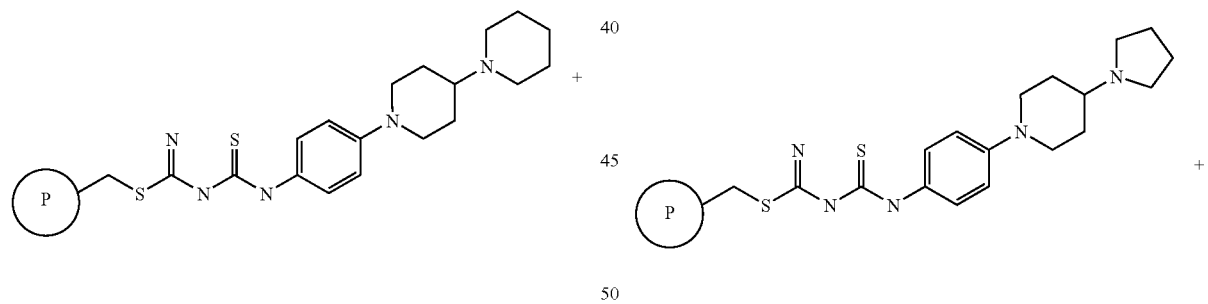

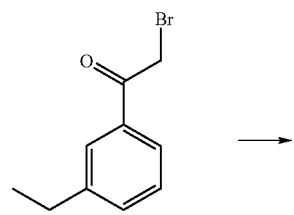

MW 227.1026
$C_{10}H_{11}BrO$

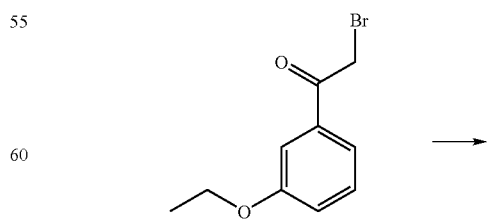

MW 243.10
$C_{10}H_{11}BrO_2$

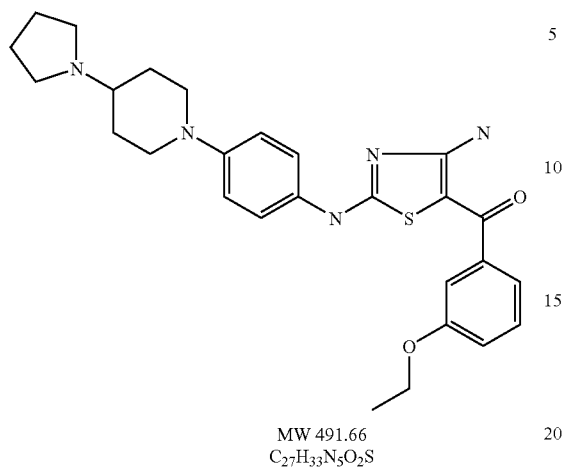

MW 491.66
C₂₇H₃₃N₅O₂S

The compound was prepared from 2-bromo-3'-ethoxy-acetophenone (Prepared according to Azuma, Hiroshi et al, WO 9902519) and the resin-bound thiourea of Example 20 following the procedure used in Example 23. MS (m+H)⁺: 492.

Example 119

{4-Amino-2-[4-(4-pyrrolidin-1-yl-piperidin-1-yl)-phenylamino]-thiazol-5-yl}-(3-cyclopropyl-phenyl)-methanone

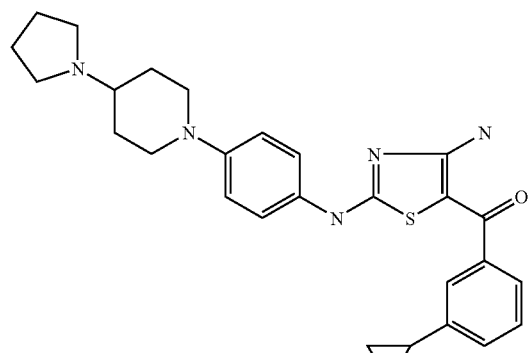

MW 487.67
C₂₈H₃₃N₅OS

The compound was prepared from 2-bromo-3'-cyclopropyl-acetophenone (Prepared according to Chu, xin-jie et al, WO 2003097048) and the resin-bound thiourea of Example 20 following the procedure used in Example 23. MS (m+H)⁺: 488.

Example 120

{4-Amino-2-[4-(4-dimethylamino-piperidin-1-yl)-phenylamino]-thiazol-5-yl}-(3-cyclopropyl-phenyl)-methanone

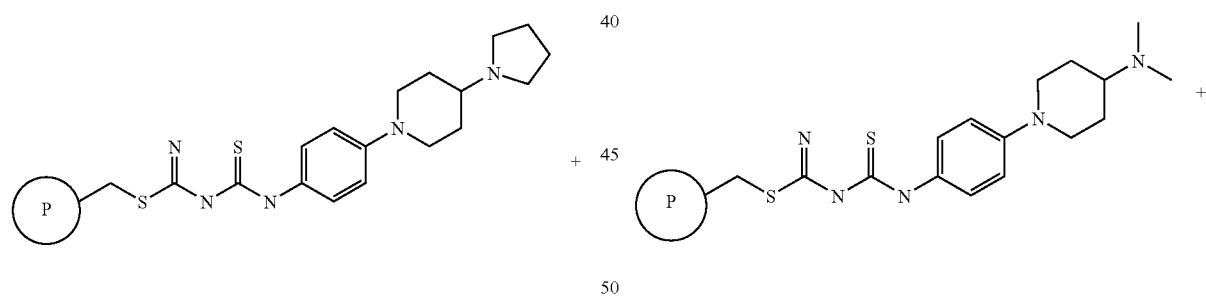

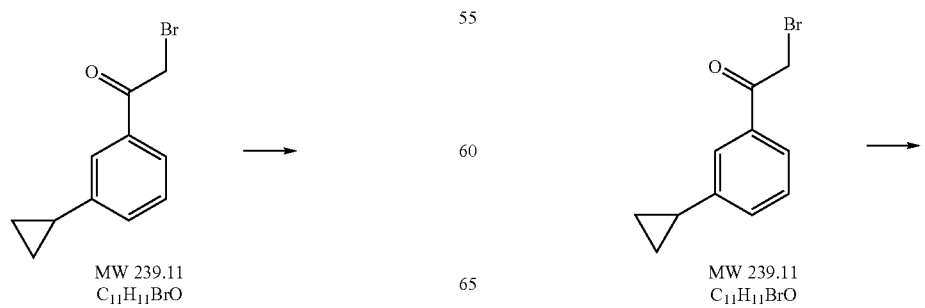

MW 239.11
C₁₁H₁₁BrO

131

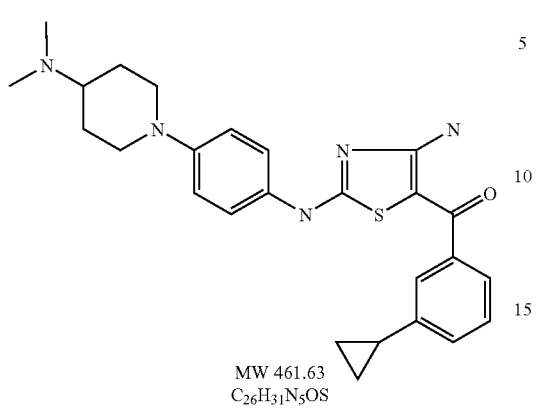

MW 461.63
C{26}H{31}N{5}OS

The compound was prepared from 2-bromo-3'-cyclopropyl-acetophenone (Prepared according to Chu, xin-jie et al, WO 2003097048) and the resin-bound thiourea of Example 18 following the procedure used in Example 23. MS (m+H)$^+$: 462.

Example 121

{4-Amino-2-[4-(4-pyrrolidin-1-yl-piperidin-1-yl)-phenylamino]-thiazol-5-yl}-(3-fluoro-4-methyl-phenyl)-methanone

132

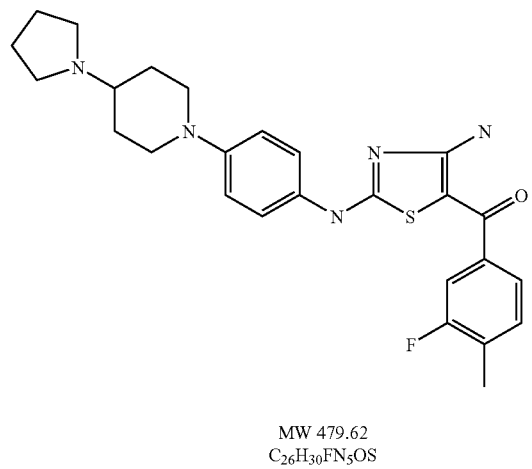

MW 479.62
C{26}H{30}FN{5}OS

The compound was prepared from 2-bromo-3'-fluoro-4'-methyl-acetophenone (Prepared according to Chu, xin-jie et al, WO 2003097048) and the resin-bound thiourea of Example 20 following the procedure used in Example 23. MS (m+H)$^+$: 480.

Example 122

{4-Amino-2-[4-(4-pyrrolidin-1-yl-piperidin-1-yl)-phenylamino]-thiazol-5-yl}-(3-ethyl-4-fluoro-phenyl)-methanone

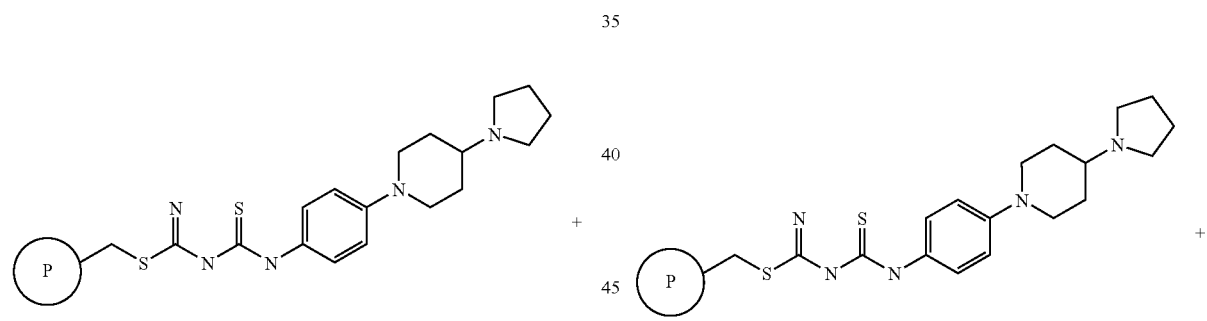

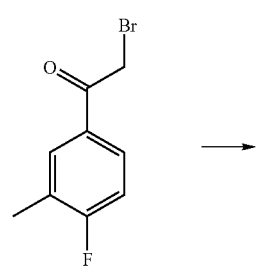

MW 231.07
C{9}H{8}BrFO

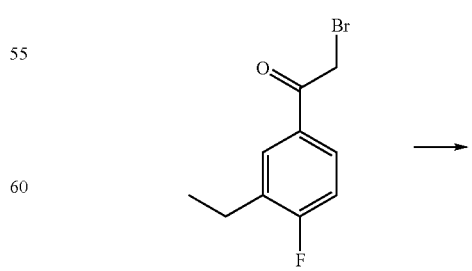

MW 245.09
C{10}H{10}BrFO

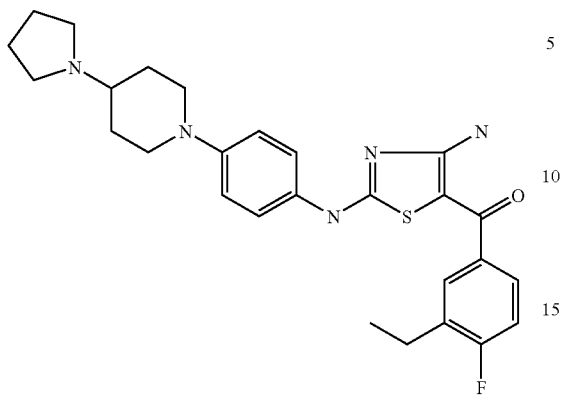

MW 493.65
C27H32FN5OS

The compound was prepared from 2-bromo-3'-ethyl-4'-fluoro-acetophenone (Prepared according to Chu, xin-jie et al, WO 2003097048) and the resin-bound thiourea of Example 20 following the procedure used in Example 23. MS (m+H)+: 494.

Example 123

{4-Amino-2-[4-(4-pyrrolidin-1-yl-piperidin-1-yl)-phenylamino]-thiazol-5-yl}-(4-hydroxy-3-propyl-phenyl)-methanone

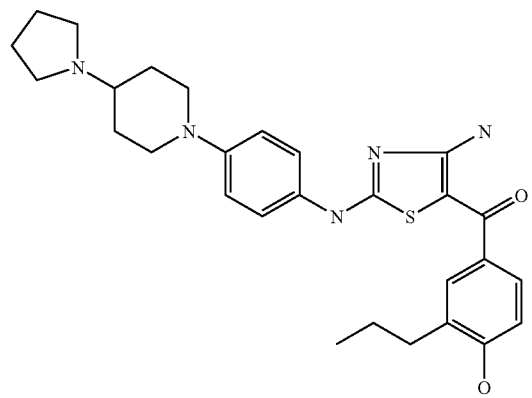

MW 505.69
C28H35N5O2S

The compound was prepared from 2-bromo-3'-propyl-4'-hydroxy-acetophenone (Prepared according to Chu, xin-jie et al, WO 2003097048) and the resin-bound thiourea of Example 20 following the procedure used in Example 23. MS (m+H)+: 506.

Example 124

6-(4-Amino-2-{4-[ethyl-(3-pyrrolidin-1-yl-propyl)-amino]-phenylamino}-thiazole-5-carbonyl)-1-H-indole-2-carboxylic acid ethyl ester

MW 257.13
C11H13BrO2

MW 310.15
C13H12BrNO3

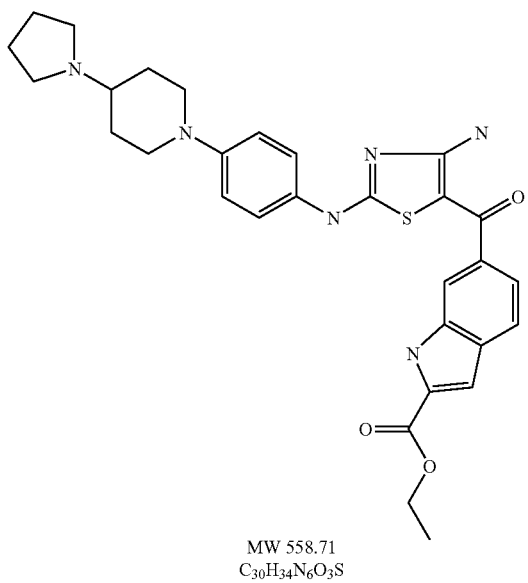

MW 558.71
C30H34N6O3S

The compound was prepared from 2-bromo-3'-propyl-4'-hydroxy-acetophenone (Prepared according to Chu, xin-jie et al, WO 2003097048) and the resin-bound thiourea of Example 20 following the procedure used in Example 23. MS (m+H)+: 559.

Example 125

Ethyl-[1-(4-nitro-phenyl)-piperidin-4-yl]-carbamic acid tert-butyl ester din-4-one (prepared by the procedure of Taylor, E. C. et al; synthesis, 1981, (8), 606–608} in 1,4-dioxane (30 mL), Dipea (Aldrich, 327 mg, 2.53 mmol) and BOC anhydride (Aldrich, 503 mg, 2.28 mmol) were added and the mixture was stirred at room temperature overnight. The mixture was poured into 600 mL of ice water and the new mixture was stirred for 1 hour. The precipitate was filtered, washed with water and dried to give a solid. 540 mg, 68%. MS (m+H)+: 350.

Example 126

[1-(4-Amino-phenyl)-piperidin-4-yl]-ethyl-carbamic acid tert-butyl ester

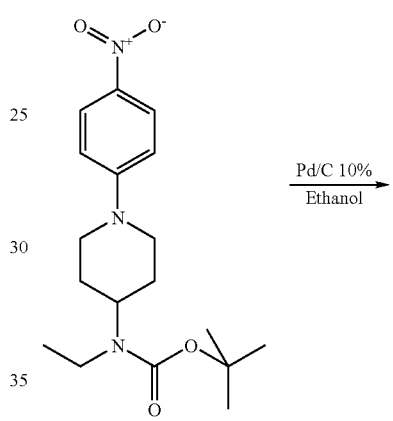

MW 349.43
C18H27N3O4

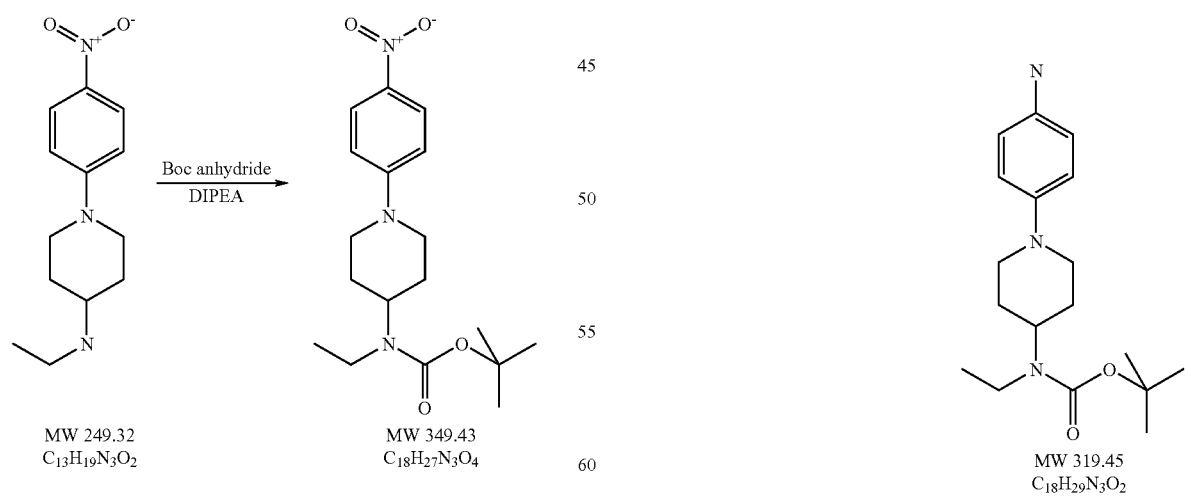

MW 249.32
C13H19N3O2

MW 349.43
C18H27N3O4

MW 319.45
C18H29N3O2

To a stirred solution of ethyl-[1-(4-nitro-phenyl)-piperidin-4-yl]-amine {570 mg, 2.28 mol, prepared through a similar procedure described by Lubisch, Wilfried et al. EP 19920422 with ethylamine and 1-[4-nitro-phenyl]-piperi- The compound was prepared from ethyl-[1-(4-nitro-phenyl)-piperidin-4-yl]-carbamic acid tert-butyl ester (Example 125) following the procedure used in Example 2. MS (m+H)+: 320.

Example 127

Ethyl-[1-(4-isothiocyanato-phenyl)-piperidin-4-yl]-carbamic acid tert-butyl ester

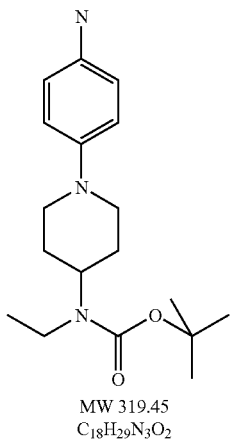

MW 319.45
C₁₈H₂₉N₃O₂

+

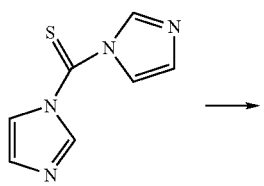

→

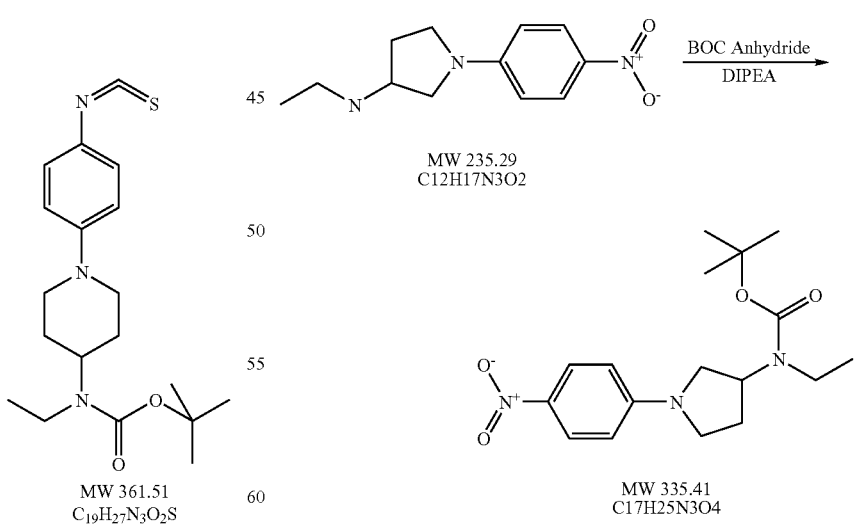

MW 361.51
C₁₉H₂₇N₃O₂S

The compound was prepared [1-(4-Amino-phenyl)-piperidin-4-yl]-ethyl-carbamic acid tert-butyl ester (Example 126) following the procedure used in Example 3. MS (m+H)⁺: 362.

Example 128

Ethyl-[1-(4-nitro-phenyl)-pyrrolidin-3-yl]-amine

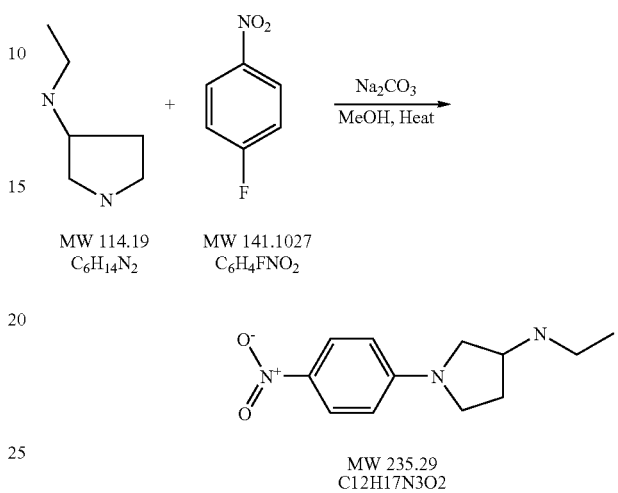

The compound was prepared from 3-ethylamino-pyrolidine (TCI-US) and 4-fluoro-nitrobenzene (Aldrich) following the procedure used in Example 1. MS (m+H)⁺: 236.

Example 129

Ethyl-[1-(4-nitro-phenyl)-pyrrolidin-3-yl]-carbamic acid tert!butyl ester

MW 235.29
C12H17N3O2

BOC Anhydride
DIPEA
→

MW 335.41
C17H25N3O4

The compound was prepared from ethyl-{1-[1-(4-nitro-phenyl)-piperidin-4-yl]-pyrrolidin-3-yl}-amine (Example 128) following the procedure used in Example 2. MS (m+H)⁺: 336.

Example 130

[1-(4-Amino-phenyl)-pyrrolidin-3-yl]-ethyl-carbamic acid tert-butyl ester

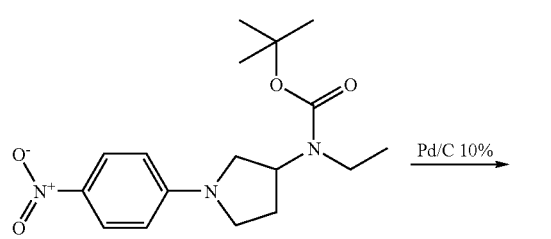

MW 335.41
C17H25N3O4

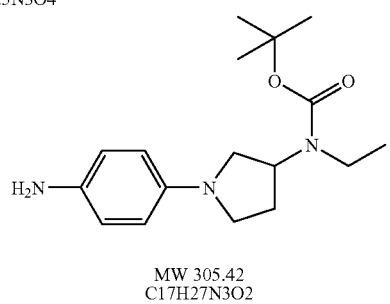

MW 305.42
C17H27N3O2

The compound was prepared from ethyl-{1-[1-(4-nitro-phenyl)-piperidin-4-yl]-pyrrolidin-3-yl}-carbamic acid tert-butyl ester (Example 129) following the procedure used in Example 2. MS (m+H)+: 306.

Example 131

Ethyl-[1-(4-isothiocyanato-phenyl)-pyrrolidin-3-yl]-carbamic acid tert-butyl ester

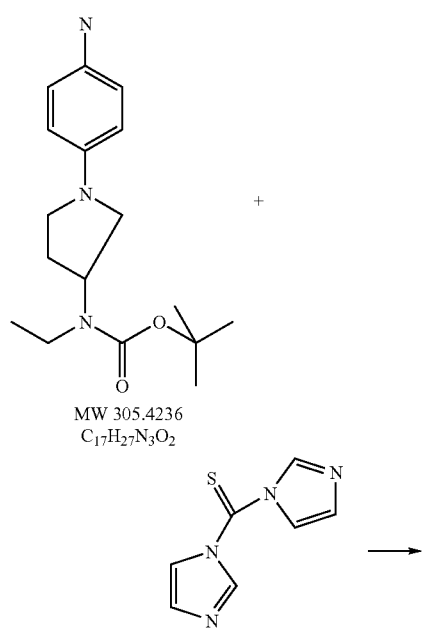

MW 305.4236
C17H27N3O2

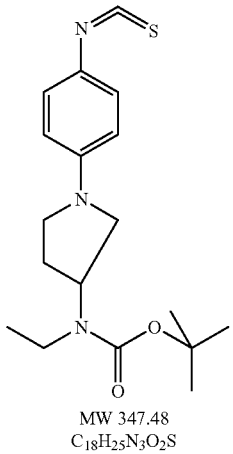

MW 347.48
C18H25N3O2S

The compound was prepared from {1-[1-(4-amino-phenyl)-piperidin-4-yl]-pyrrolidin-3-yl}-ethyl-carbamic acid tert-butyl ester (Example 130) following the procedure used in Example 3. MS (m+H)+: 348.

Example 132

{4-Amino-2-[4-(3-ethylamino-pyrrolidin-1-yl)-phenylamino]-thiazol-5-yl}-(3-fluoro-phenyl)-methanone

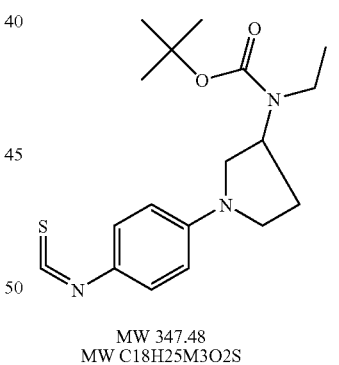

MW 347.48
MW C18H25M3O2S

MW 217.04
C8H6BrFO

1. NH2CN, KOtBu
2. 50% TFA/CH2Cl2

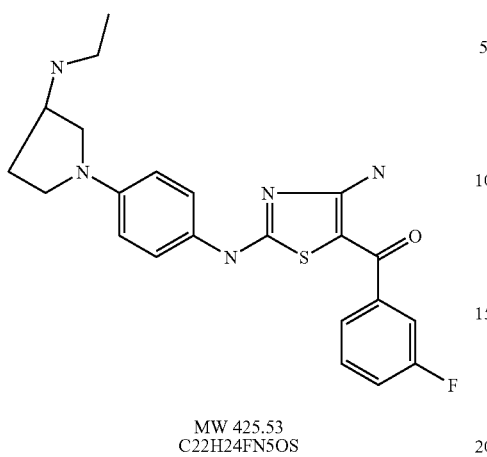

MW 425.53
C22H24FN5OS

The compound was prepared from 3-fluorophenylacyl bromide (Maybridge International) and the compound of Example 131 following the procedure described by Chu, Xin-jie et al. WO 2003097048. MS (m+H)+: 426.

Example 133

{4-Amino-2-[4-(3-ethylamino-pyrrolidin-1-yl)-phenylamino]-thiazol-5-yl}-(3-fluoro-4-methoxy-phenyl)-methanone

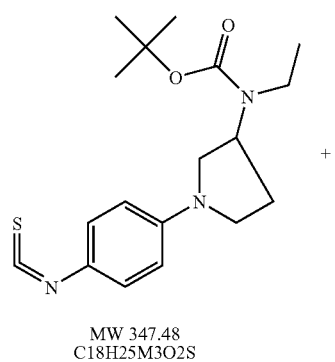

MW 347.48
C18H25M3O2S

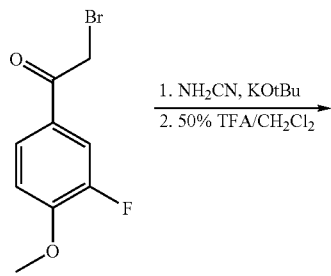

MW 247.07
C9H8BrFO2

1. NH2CN, KOtBu
2. 50% TFA/CH2Cl2

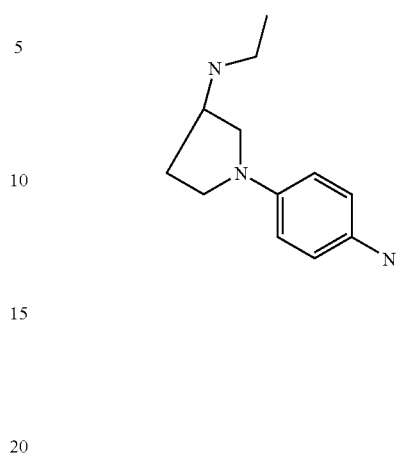

MW 455.56
C23H26FN5O2S

The compound was prepared from 3-fluoro-4-methoxyphenylacyl bromide (Maybridge International) and the compound of Example 131 following the procedure described by Chu, Xin-jie et al. WO 2003097048. MS (m+H)+: 456.

Example 134

{4-Amino-2-[4-(3-ethylamino-pyrrolidin-1-yl)-phenylamino]-thiazol-5-yl}-(3-methoxy-phenyl)-methanone

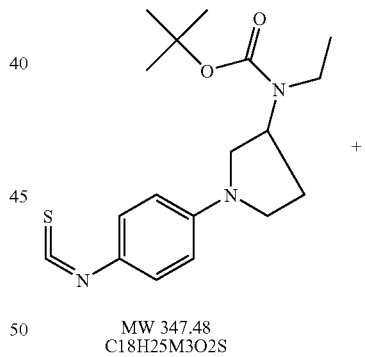

MW 347.48
C18H25M3O2S

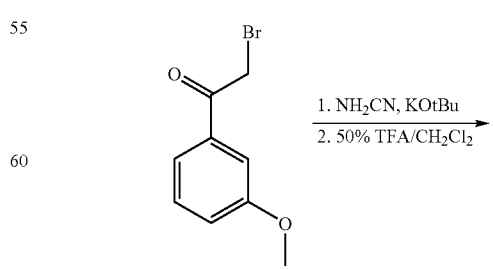

MW 229.07
C9H9BrO2

1. NH2CN, KOtBu
2. 50% TFA/CH2Cl2

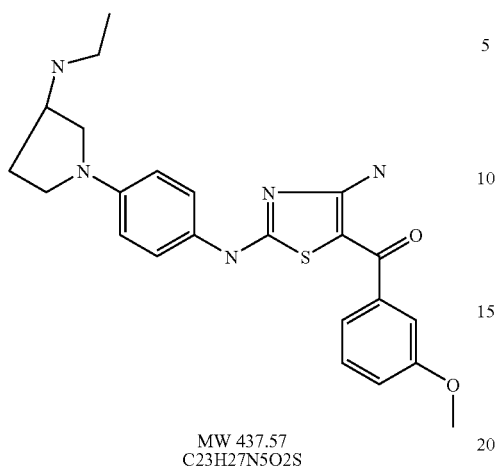

MW 437.57
C23H27N5O2S

The compound was prepared from 3-methoxy-phenylacyl bromide (Maybridge International) and the compound of Example 131 following the procedure described by Chu, Xin-jie et al; WO 2003097048. MS (m+H)+: 438.

Example 135

{4-Amino-2-[4-(4-ethylamino-piperidin-1-yl)-phenylamino]-thiazol-5-yl}-(3-methoxy-phenyl)-methanone

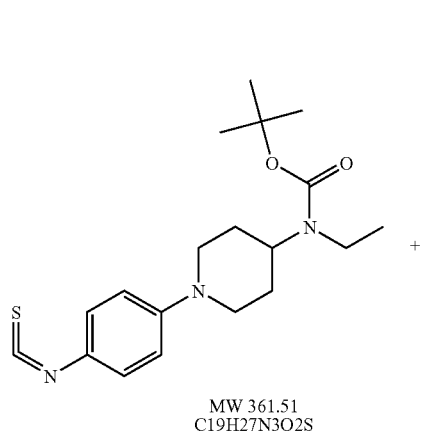

MW 361.51
C19H27N3O2S

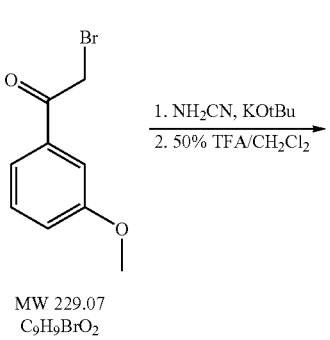

MW 229.07
C9H9BrO2

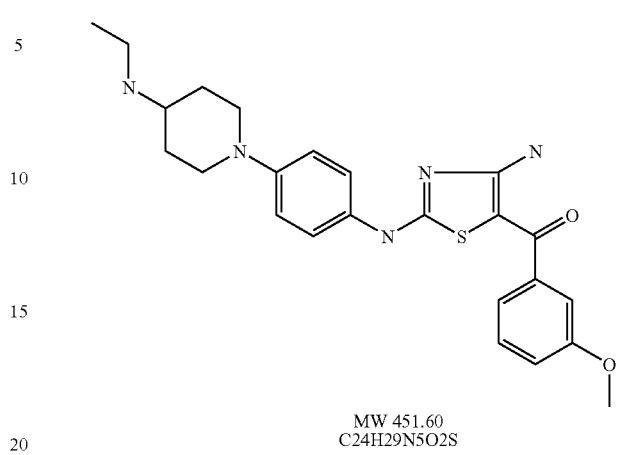

MW 451.60
C24H29N5O2S

The compound was prepared from 3-methoxy-phenylacyl bromide (Maybridge International) and the compound of Example 127 following the procedure described by Chu, Xin-jie et al. WO 2003097048. MS (m+H)+: 452.

Example 136

{4-Amino-2-[4-(4-ethylamino-piperidin-1-yl)-phenylamino]-thiazol-5-yl}-(3-fluoro-4-methoxy-phenyl)-methanone

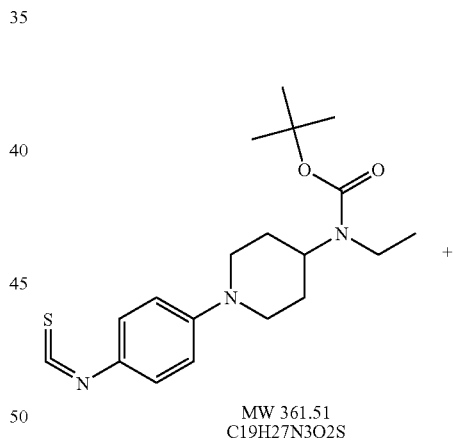

MW 361.51
C19H27N3O2S

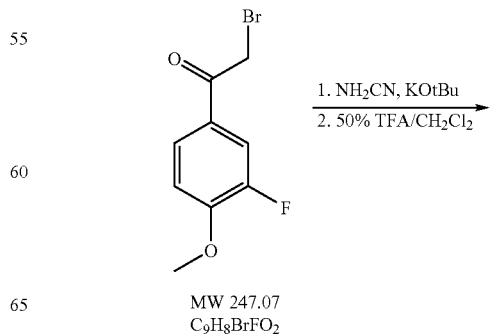

MW 247.07
C9H8BrFO2

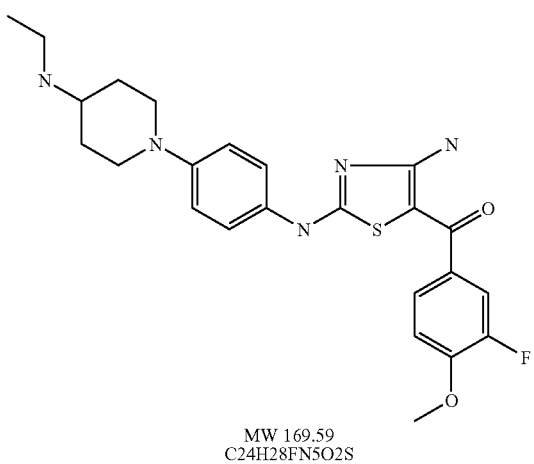

MW 169.59
C24H28FN5O2S

The compound was prepared from 3-Fluoro-4-methoxyphenylacyl bromide (Maybridge International) and the compound of example 127 following the procedure described by Chu, Xin-jie et al. WO 2003097048. MS (m+H)+: 470.

Example 137

{4-Amino-2-[4-(4-ethylamino-piperidin-1-yl)-phenylamino]-thiazol-5-yl}-(3-fluoro-phenyl)-menthanone

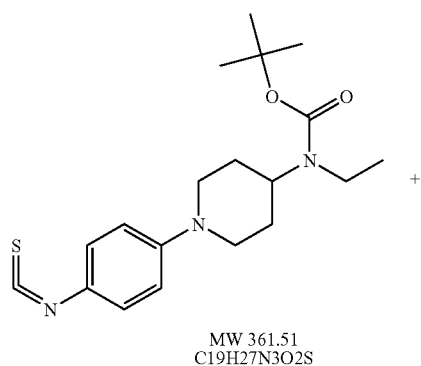

MW 361.51
C19H27N3O2S

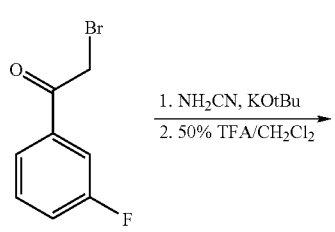

1. NH₂CN, KOtBu
2. 50% TFA/CH₂Cl₂

MW 217.04
C8H6BrFO

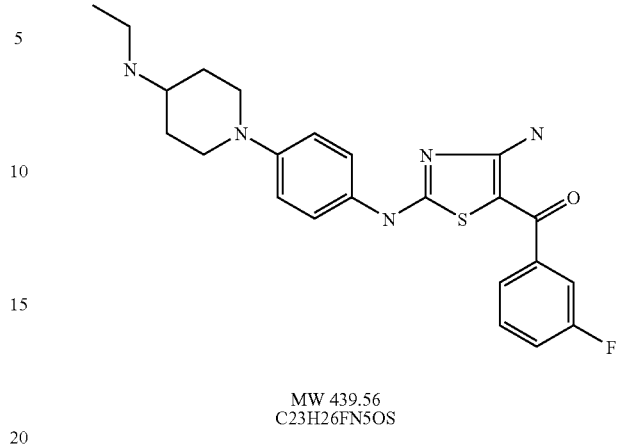

MW 439.56
C23H26FN5OS

The compound was prepared from 3-Fluoro-phenylacyl bromide (Maybridge International) and the compound Example 127 following the procedure described by Chu, Xin-jie et at; WO 2003097048. MS (m+H)+: 440.

Example 138

Antiproliferative Activity

The antiproliferative activity of the compounds of the invention is demonstrated below. These activities indicate that the compounds of the present invention are useful in treating cancer, in particular solid tumors such as breast and colon tumors.

Kinase Assays

To determine inhibition of Cdk4, Cdk2 and Cdk1 activity, kinase assays were conducted using FlashPlate™ assays (NEN™-Life Science Products). FlashPlate assays were performed using recombinant human cyclin B-CDK1, human cyclin E-CDK2 or human cyclin D1-CDK4 complexes. GST-cyclinE (GST-cycE), CDK2, GST-cyclinB (GST-cycB), CDK1, GST-CDK4 and cyclin D1 (cycD1) cDNA clones in baculovirus vectors were provided by Dr. W. Harper at the Baylor College of Medicine, Houston, Tex. Proteins were co-expressed in High Five™ insect cells and the complex was purified on glutathione Sepharose resin (Pharmacia, Piscataway, N.J.) as previously described (Harper, J. W. et al. *Cell* 1993, 75, 805–816). A 6×-Histidine tagged truncated form of retinoblastoma (Rb) protein (amino acid 386–928) was used as the substrate for the cycD1-CDK4, cycB-CDK1 and the cycE-CDK2 assays (the expression plasmid was provided by Dr. Veronica Sullivan, Department of Molecular Virology, Roche Research Centre, Welwyn Garden City, United Kingdom). The Rb protein is a natural substrate for phosphorylation by CDK4, CDK2 and CDK1 (see Herwig and Strauss *Eur. J. Biochem.* Vol. 246 (1997) pp. 581–601 and the references cited therein).

The expression of the 62Kd protein was under the control of an IPTG inducible promoter in an M15 *E. coli* strain. Cells were lysed by sonication and purification was carried out by binding lysates at pH 8.0 to a Ni-chelated agarose column pretreated with 1 mM imidazole. The resin was then washed several times with incrementally decreasing pH buffers to pH 6.0, and eluted with 500 mM imidazole. Eluted protein was dialysed against 20 mM HEPES pH 7.5, 30% glycerol, 200 mM NaCl, and 1 mM DTT. Purified Rb fusion protein stocks were quantitated for protein concentration, aliquoted, and stored at −70° C.

For all three kinase assays reported herein, 96-well Flash-Plates were coated with Rb protein at 10 µg/ml, using 100 µl per well. Plates were incubated at 4° C. overnight or at room temperature for 3 hours on a shaker. To control for nonspecific phosphorylation, one row of wells was coated with 100 µl/well coating buffer (20 mM HEPES, 0.2 M NaCl). Plates were then washed twice with wash buffer (0.01% Tween 20 in phosphate-buffered saline). Compounds to be tested ("test compounds") were added to the wells at 5× final concentration. Reactions were initiated by immediate addition of 40 µl reaction mix (25 mM HEPES, 20 mM $MgCl_2$, 0.002% Tween 20, 2 mM DTT, 1 µM ATP, 4 nM $^{33}$P-ATP) and a sufficient amount of enzyme to give counts that were at least 10-fold above background. Plates were incubated at room temperature on a shaker for 30 minutes. Plates were washed four times with the wash buffer, sealed, and counted on the TopCount scintillation counter (Packard Instrument Co., Downers Grove, Ill.]. The percent inhibition of Rb phosphorylation, which is a measure of the inhibition of CDK activity, was determined according to the following formula:

$$100 \times 1 - \frac{\text{test compound} - \text{nonspecific}}{\text{total} - \text{nonspecific}}$$

where "test compound" refers to the average counts per minute of the test duplicates, "nonspecific" refers to the average counts per minute when no CyclinD/Cdk4, etc., was added, and "total" refers to the average counts per minute when no compound was added. The $IC_{50}$ value is the concentration of test compound that reduces by 50% the protein-kinase induced incorporation of the radiolabel under the test conditions described.

The results of the foregoing in vitro experiments are set forth in Table 1 below. The $IC_{50}$ values are summarized in the Table 1 below.

Cell Based Assays (Tetrazolium Dye Proliferation Assay)

Proliferation was evaluated by the tetrazolium dye assay according to the procedure of Denizot and Lang (Denizot, F. and Lang, R. *J Immunol Methods* 1986, 89, 271–277). The cell line used was HCT116, a colorectal carcinoma cell line obtained from the American Type Cell Culture Collection (ATCC; Rockville, Md.). The cells were grown in McCoy's 5A medium supplemented with 10% FCS and L-glutamine.

Cells were plated at the appropriate seeding density to give logarithmic growth over the course of the assay in a 96-well tissue culture plate. Plates were incubated overnight at 37° C. in a humidified incubator with 5% $CO_2$. The next day, test compounds were serially diluted to four times the final concentration in the appropriate medium containing 1.2% DMSO. One-fourth final volume of each dilution was added in duplicate to the plates containing cells. The same volume of 1.2% DMSO in medium was added to a row of "control wells" such that the final concentration of DMSO in each well was 0.3%. Wells to which no cells were added served as the "blank." Wells to which no inhibitor was added served as "no inhibitor control." The plates were) returned to the incubator, and at set time points (determined by their growth curves) plates were analyzed as described below.

3-(4,5-dimethylthiazole-2-yl)-2,5-diphenyl-2H-tetrazolium bromide (thiazolyl blue; MTT; Sigma) was added to each well to yield a final concentration of 1 mg/ml. Plates were returned to the incubator for 2.5–3 hours at 37° C. The MTT-containing medium was removed and the resulting formazan metabolite was solubilized in 100% ethanol with shaking for 15 minutes at room temperature. Absorbance readings were taken in a microtiter plate reader (Dynatech and Molecular Devices plate readers were used interchangeably) at a wavelength of 570 nm with a 650 nm reference. Percent inhibition (% INH) is calculated by subtracting the absorbance of the blank well from all wells, then subtracting the ratio of the average absorbance of each test duplicate ($S_{AVE}$) by the average of the controls ($C_{AVE}$) from 1.00. The final number is then multiplied by 100 (% INH=(1.00−$S_{AVE}$/$C_{AVE}$)×100). The concentration at which 50% inhibition of cell proliferation is obtained (the $IC_{50}$) is determined from the linear regression of a plot of the logarithm of the concentration versus percent inhibition. The $IC_{50}$ values are also shown in Table 1 below.

TABLE 1

This table shows the $IC_{50}$s of compounds of the instant Examples in CDK4, CDK2, and CDK1 kinase assays, and also the $IC_{50}$s in the cell-based assays ("MTT") assay.

| Example Number | CDK4 $IC_{50}$(µM) | CDK2 $IC_{50}$(µM) | CDK1 $IC_{50}$(µM) | MTT $IC_{50}$(µM) |
|---|---|---|---|---|
| Example 23 | 0.012 | 2.89 | 1.28 | 1.75 |
| Example 24 | 0.032 | 0.86 | 0.27 | 1.22 |
| Example 25 | 0.017 | 2.89 | 0.216 | 2.00 |
| Example 26 | 0.005 | 4.25 | 1.06 | 2.80 |
| Example 27 | 0.017 | 3.49 | 1.06 | 1.85 |
| Example 28 | 0.053 | 4.18 | 1.17 | nd |
| Example 29 | 0.055 | 3.99 | 1.23 | nd |
| Example 30 | 0.014 | 0.545 | 0.176 | 0.84 |
| Example 31 | 0.028 | 4.16 | 1.72 | 3.29 |
| Example 32 | 0.029 | 5.74 | 1.91 | 6.64 |
| Example 33 | 0.009 | 4.95 | 0.95 | 1.68 |
| Example 34 | 3.64 | 0.952 | 1.68 | 0.008 |
| Example 35 | 1.09 | 0.12 | 0.74 | 0.018 |
| Example 36 | 3.63 | 3.00 | 1.73 | 0.009 |
| Example 37 | 3.52 | 0.52 | 1.63 | 0.10 |
| Example 38 | 5.26 | 1.45 | 4.05 | 0.015 |
| Example 39 | 4.26 | 0.97 | 1.37 | 0.023 |
| Example 40 | 0.052 | 5.11 | 0.64 | 9.48 |
| Example 41 | 0.002 | 0.888 | 0.268 | 1.41 |
| Example 42 | 0.086 | 5.83 | 5.79 | nd |
| Example 43 | 0.007 | 3.5 | 0.50 | 1.61 |
| Example 44 | 0.016 | 5.13 | 1.25 | 1.72 |
| Example 45 | 0.005 | 5.16 | 2.44 | 2.46 |
| Example 46 | 0.055 | 5.67 | 3.81 | Nd |
| Example 47 | 0.186 | 10 | 10 | nd |
| Example 48 | 0.074 | 10 | 10 | nd |
| Example 49 | 0.008 | 0.136 | 0.005 | nd |
| Example 50 | 0.007 | 2.79 | 0.81 | 3.12 |
| Example 51 | 0.23 | 10 | 10 | nd |
| Example 52 | 0.071 | 10 | 10 | nd |
| Example 53 | 0.096 | 10 | 10 | nd |
| Example 54 | 0.212 | 10 | 10 | nd |
| Example 55 | 0.37 | 10 | 10 | nd |
| Example 56 | 0.16 | 10 | 4.77 | nd |
| Example 57 | 0.086 | 8.03 | 3.56 | nd |
| Example 58 | 0.045 | 10 | 10 | nd |
| Example 59 | 0.061 | 3.09 | 4.63 | nd |
| Example 60 | 0.09 | 10 | 5.77 | nd |
| Example 61 | 0.071 | 10 | 10 | nd |
| Example 62 | 0.278 | 4.17 | 4.21 | nd |
| Example 63 | 0.32 | 10 | 10 | nd |
| Example 64 | 0.015 | 2.70 | 1.28 | nd |
| Example 65 | 0.018 | 3.39 | 1.44 | nd |
| Example 66 | 0.076 | 10 | 4.02 | nd |

TABLE 1-continued

This table shows the IC$_{50}$s of compounds of the instant Examples in CDK4, CDK2, and CDK1 kinase assays, and also the IC$_{50}$s in the cell-based assays ("MTT") assay.

| Example Number | CDK4 IC$_{50}$(μM) | CDK2 IC$_{50}$(μM) | CDK1 IC$_{50}$(μM) | MTT IC$_{50}$(μM) |
|---|---|---|---|---|
| Example 67 | 0.17 | 10 | 10 | nd |
| Example 68 | 0.089 | 5.95 | 3.85 | nd |
| Example 69 | 0.102 | 5.62 | 6.23 | nd |
| Example 70 | 0.186 | 10 | 10 | nd |
| Example 71 | 0.162 | 4.15 | 4.06 | nd |
| Example 72 | 0.017 | 2.05 | 0.702 | 2.50 |
| Example 73 | 0.088 | 8.05 | 2.59 | nd |
| Example 74 | 0.062 | 10 | 10 | nd |
| Example 75 | 0.058 | 8.68 | 4.05 | nd |
| Example 76 | 0.124 | 8.76 | 10 | nd |
| Example 77 | 0.111 | 10 | 10 | nd |
| Example 78 | 0.246 | 3.71 | 2.90 | nd |
| Example 79 | 0.40 | 10 | 10 | nd |
| Example 80 | 0.017 | 2.58 | 1.37 | 3.49 |
| Example 81 | 0.019 | 3.45 | 1.61 | 6.02 |
| Example 82 | 0.084 | 7.84 | 4.27 | nd |
| Example 83 | 0.132 | 10 | 10 | nd |
| Example 84 | 0.122 | 9.51 | 3.73 | nd |
| Example 85 | 0.098 | 2.26 | 0.51 | nd |
| Example 86 | 0.114 | 10 | 10 | nd |
| Example 87 | 0.133 | 4.44 | 2.99 | nd |
| Example 88 | 0.015 | 3.91 | 0.94 | nd |
| Example 89 | 0.10 | 2.26 | 0.51 | nd |
| Example 90 | 0.007 | 1.67 | 0.58 | 2.82 |
| Example 91 | 0.009 | 1.82 | 0.71 | 1.64 |
| Example 92 | 0.015 | 1.60 | 0.87 | 2.90 |
| Example 93 | 0.677 | 10 | 10 | nd |
| Example 94 | 0.39 | 10 | 10 | nd |
| Example 96 | 0.037 | 4.06 | 1.18 | nd |
| Example 97 | nd | nd | nd | nd |
| Example 98 | 0.039 | 10 | 2.70 | nd |
| Example 99 | 0.035 | 0.55 | 0.45 | nd |
| Example 100 | 0.090 | 10 | 4.17 | nd |
| Example 101 | 0.025 | 10 | 0.58 | nd |
| Example 102 | 0.029 | 4.80 | 1.99 | nd |
| Example 103 | 0.036 | 3.34 | 1.52 | nd |
| Example 104 | 0.031 | 2.00 | 1.28 | nd |
| Example 105 | 0.039 | 1.51 | 1.28 | nd |
| Example 106 | 0.052 | 4.83 | 2.27 | nd |
| Example 107 | 0.038 | 2.39 | 1.00 | 3.68 |
| Example 108 | 0.034 | 2.61 | 1.29 | 0.996 |
| Example 109 | 0.014 | 2.62 | 0.77 | nd |
| Example 110 | 0.025 | 3.52 | 1.99 | 2.70 |
| Example 111 | 0.025 | 2.92 | nd | 1.61 |
| Example 112 | nd | nd | nd | nd |
| Example 113 | 0.045 | 7.27 | 0.94 | 1.74 |
| Example 114 | 0.012 | 0.945 | 2.71 | 1.37 |
| Example 115 | 0.010 | 1.04 | 2.80 | 1.24 |
| Example 116 | 0.015 | 0.75 | 5.59 | 2.55 |
| Example 117 | 0.009 | 0.989 | 3.22 | 1.31 |
| Example 118 | 0.031 | 3.24 | 1.53 | 4.15 |
| Example 119 | 0.011 | 3.24 | 1.53 | 3.17 |
| Example 120 | 0.023 | 2.58 | 1.87 | 3.91 |
| Example 121 | 0.011 | 1.94 | 0.70 | 2.16 |
| Example 122 | 0.020 | 5.31 | 5.19 | 4.22 |
| Example 123 | 0.014 | 0.20 | 0.345 | 1.05 |
| Example 124 | 0.067 | 4.32 | 11.43 | nd |
| Example 132 | 0.029 | 0.701 | 0.253 | 0.568 |
| Example 133 | 0.066 | 3.27 | 1.86 | 1.02 |
| Example 134 | 0.046 | 4.50 | 1.33 | 1.24 |
| Example 135 | 0.028 | 6.10 | 1.15 | 3.37 |
| Example 136 | 0.050 | 9.43 | 1.56 | 3.26 |
| Example 137 | 0.032 | 1.01 | 0.385 | 1.40 | nd means "not determined".

Example 139

Tablet Formulation

| Item | Ingredients | Mg/Tablet | | | | | |
|---|---|---|---|---|---|---|---|
| 1 | Compound A * | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

* Compound A represents a compound of the invention.

Manufacturing Procedure:
1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

Example 140

Capsule Formulation

| Item | Ingredients | mg/Capsule | | | | |
|---|---|---|---|---|---|---|
| 1 | Compound A * | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

Compound A represents a compound of the invention.

Manufacturing Procedure:
1. Mix items 1, 2 and 3 in a suitable mixer for 15 minutes.
2. Add items 4 & 5 and mix for 3 minutes.
3. Fill into a suitable capsule.

Example 141

Injection Solution/Emulsion Preparation

| Item | Ingredient | mg/mL |
|---|---|---|
| 1 | Compound A * | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

Example 142

Injection Solution/Emulsion Preparation

| Item | Ingredient | mg/mL |
|---|---|---|
| 1 | Compound A * | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

What is claimed is:
1. A compound of formula (I):

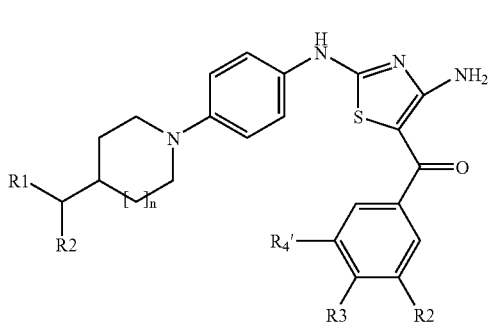

wherein,
n is 0 or 1;
$R^1$ and $R^2$ are each independently selected from the group consisting of H, lower alkyl, $CO_2R^5$, $SO_2R^6$, and $COR^6$;
or alternatively, $R^1$ and $R^2$ can form a ring having a total of 5–7 ring atoms, said ring comprising carbon atoms, said carbon atoms optionally being replaced by one or two heteroatoms, and said ring atoms optionally being substituted by $OR^6$;
$R^3$ is selected from the group consisting of H, lower alkyl, O-lower alkyl, halogen, OH, CN, $NO_2$, and COOH;
$R^4$ is selected from the group consisting of H, lower alkyl, cycloalkyl, O-lower alkyl, halogen, $NO_2$, S-lower alkyl, $CF_3$, $NR^5R^6$, $CONR^7R^8$, $CO_2R^6$, OH, and CN;
or alternatively, $R^3$ and $R^4$, together with the two carbon atoms and bond between them from the benzene ring to which $R^3$ and $R^4$ are attached, can form a ring having 5–7 ring atoms, said 5–7 atom ring comprising carbon atoms, said carbon atoms optionally being replaced by one or two heteroatoms, and said ring atoms optionally being substituted by $C_1$–$C_4$ alkyl and $CO_2R^6$;
$R^{4'}$ is H or halogen;
$R^5$ and $R^6$ are each independently selected from the group consisting of H, lower alkyl, cycloalkyl, heterocycle, aryl, and aryl substituted by lower alkoxy, halogen, or CN;
$R^7$ and $R^8$ are each independently selected from the group consisting of H, lower alkyl, lower alkyl substituted by $OR^5$, and $NR^5R^6$;
or alternatively, the group $NR^7R^8$ can form a ring having a total of 5–7 ring atoms, said ring atoms comprising in addition to the nitrogen to which $R^7$ and $R^8$ are bonded, carbon ring atoms, said carbon ring atoms optionally being replaced by one or two heteroatoms, and said ring atoms being optionally substituted by $C_1$–$C_4$ alkyl, $COR^6$, $CONR^5R^6$, or $CO_2R^6$; or
a pharmaceutically acceptable salt or ester thereof.

2. The compound of claim 1, where n is 1.
3. The compound of claim 1, where $R^1$ is selected from the group consisting of H, lower alkyl, and $CO_2R^5$.
4. The compound of claim 1, where $R^2$ is selected from the group consisting of H, lower alkyl, and $CO_2R^5$.
5. The compound of claim 1, where $R^1$ and $R^2$ form a ring having a total of 5–6 ring atoms.
6. The compound of claim 1, where $R^3$ is selected from the group consisting of H, lower alkyl, and O-lower alkyl.
7. The compound of claim 1, where $R^4$ is selected from the group consisting of H, lower alkyl, and O-lower alkyl.
8. The compound of claim 1, where $R^3$ and $R^4$ form a ring having a total of 5–6 ring atoms.
9. The compound of claim 1, where $R^5$ is selected from the group consisting of H, lower alkyl, and cycloalkyl.
10. The compound of claim 1, where $R^6$ is selected from the group consisting of H, lower alkyl, and cycloalkyl.
11. The compound of claim 1, where $R^7$ is H or lower alkyl.
12. The compound of claim 1, where $R^8$ is H or lower alkyl.
13. The compound of claim 1, where $R^7$ and $R^8$ form a ring having a total of 5–6 ring atoms.
14. The compound of claim 1, selected from the group consisting of:
{2-Amino-5-[4-(4-pyrrolidin-1-yl-piperidin-1-yl)-phenylamino]-4H-pyrrol-3-yl}-(3-fluoro-4-methoxy-phenyl)-methanone (Example 23)
{4-Amino-2-[4-(4-pyrrolidin-1-yl-piperidin-1-yl)-phenylamino]-thiazol-5-yl}-(3-fluoro-phenyl)-methanone (Example 24)
{4-Amino-2-[4-(4-pyrrolidin-1-yl-piperidin-1-yl)-phenylamino]-thiazol-5-yl}-benzo[1,3]dioxol-5-yl-methanone (Example 25)
{4-Amino-2-[4-(4-pyrrolidin-1-yl-piperidin-1-yl)-phenylamino]-thiazol-5-yl}-(2,3-dihydro-benzo[1,4]dioxin-6-yl)-methanone (Example 26)

{4-Amino-2-[4-(4-pyrrolidin-1-yl-piperidin-1-yl)-phenylamino]-thiazol-5-yl}-(3-methoxy-phenyl)-methanone (Example 27)

{4-Amino-2-[4-(4-pyrrolidin-1-yl-piperidin-1-yl)-phenylamino]-thiazol-5-yl}-(4-hydroxy-phenyl)-methanone (Example 28)

[4-Amino-2-(4-[1,4']bipiperidinyl-1'-yl-phenylamino)-thiazol-5-yl]-(4-hydroxy-phenyl)-methanone (Example 29)

[4-Amino-2-(4-[1,4']bipiperidinyl-1'-yl-phenylamino)-thiazol-5-yl]-(3-fluoro-phenyl)-methanone (Example 30)

[4-Amino-2-(4-[1,4']bipiperidinyl-1'-yl-phenylamino)-thiazol-5-yl]-(3-fluoro-4-methoxy-phenyl)-methanone (Example 31) and

[4-Amino-2-(4-[1,4']bipiperidinyl-1'-yl-phenylamino)-thiazol-5-yl]-benzo[1,3]dioxol-5-yl-methanone (Example 32).

15. The compound of claim 1, selected from the group consisting of:

[4-Amino-2-(4-[1,4']bipiperidinyl-1'-yl-phenylamino)-thiazol-5-yl]-(2,3-dihydro-benzo[1,4]dioxin-6-yl)-methanone (Example 33)

[4-Amino-2-(4-[1,4']bipiperidinyl-1'-yl-phenylamino)-thiazol-5-yl]-(3-methoxy-phenyl)-methanone (Example 34)

{4-Amino-2-[4-(3-hydroxy-[1,4']bipiperidinyl-1'-yl)-phenylamino]-thiazol-5-yl}-(3-fluoro-phenyl)-methanone (Example 35)

{4-Amino-2-[4-(3-hydroxy-[1,4']bipiperidinyl-1'-yl)-phenylamino]-thiazol-5-yl}-(3-fluoro-4-methoxy-phenyl)-methanone (Example 36)

{4-Amino-2-[4-(3-hydroxy-[1,4']bipiperidinyl-1'-yl)-phenylamino]-thiazol-5-yl}-benzo[1,3]dioixol-5-yl-methanone (Example 37)

{4-Amino-2-[4-(3-hydroxy-[1,4']bipiperidinyl-1'-yl)-phenylamino]-thiazol-5-yl}-(2,3-dihydro-benzo[1,4]dioxin-6-yl)-methanone (Example 38)

{4-Amino-2-[4-(3-hydroxy-[1,4']bipiperidinyl-1'-yl)-phenylamino]-thiazol-5-yl}-(2,3-dihydro-benzo[1,4]dioxin-6-yl)-methanone (Example 39)

{4-Amino-2-[4-(3-hydroxy-[1,4']bipiperidinyl-1'-yl)-phenylamino]-thiazol-5-yl}-4-hydroxy-phenyl)-methanone (Example 40)

{4-Amino-2-[4-(4-dimethylamino-piperidin-1-yl)-phenylamino]-thiazol-5-yl}-(3-fluoro-phenyl)-methanone (Example 41) and {4-Amino-2-[4-(4-dimethylamino-piperidin-1-yl)-phenylamino]-thiazol-5-yl}-(3-fluoro-4-methoxy-pheny)-methanone (Example 42).

16. The compound of claim 1, selected from the group consisting of:

{4-Amino-2-[4-(4-dimethylamino-piperidin-1-yl)-phenylamino]-thiazol-5-yl}-benzo[1,3]dioxol-5-yl-methanone (Example 43)

{4-Amino-2-[4-(4-dimethylamino-piperidin-1-yl)-phenylamino]-thiazol-5-yl}-(2,3-dihydro-benzo[1,4]dioxin-6-yl)-methanone (Example 44)

{4-Amino-2-[4-(4-dimethylamino-piperidin-1-yl)-phenylamino]-thiazol-5-yl}-(3-methoxy-phenyl)-methanone (Example 45)

{4-Amino-2-[4-(4-dimethylamino-piperidin-1-yl)-phenylamino]-thiazol-5-yl}-(4-hydroxy-phenyl)-methanone (Example 46)

4-{4-Amino-2-[4-(4-dimethylamino-piperidin-1-yl)-phenylamino]-thiazole-5-carbonyl}-benzonitrile (Example 47)

{4-Amino-2-[4-(4-dimethylamino-piperidin-1-yl)-phenylamino]-thiazol-5-yl}-(4-nitro-phenyl)-methanone (Example 48)

{4-Amino-2-[4-(4-dimethylamino-piperidin-1-yl)-phenylamino]-thiazol-5-yl}-(3-hydroxy-phenyl)-methanone (Example 50)

4-{4-Amino-2-[4-(3-hydroxy-[1,4']bipiperidinyl-1'-yl)-phenylamino]-thiazole-5-carbonyl}-benzonitrile (Example 51) and {4-Amino-2-[4-(3-hydroxy-[1,4']bipiperidinyl-1'-yl)-phenylamino]-thiazol-5-yl}-(4-nitro-phenyl)-methanone (Example 52).

17. The compound of claim 1, selected from the group consisting of:

{4-Amino-2-[4-(4-pyrrolidin-1-yl-piperidin-1-yl)-phenylamino]-thiazol-5-yl}-(4-nitro-phenyl)-methanone (Example 53)

4-{4-Amino-2-[4-(4-pyrrolidin-1-yl-piperidin-1-yl)-phenylamino]-thiazole-5-carbonyl}-benzonitrile (Example 54)

4-[4-Amino-2-(4-[1,4']bipiperidinyl-1'-yl-phenylamino)-thiazole-5-carbonyl]-benzonitrile (Example 55)

[4-Amino-2-(4-[1,4']bipiperidinyl-1'-yl-phenylamino)-thiazol-5-yl]-(4-nitro-phenyl)-methanone (Example 56)

[4-Amino-2-(4-[1,4']bipiperidinyl-1'-yl-phenylamino)-thiazol-5-yl]-(3,5-difluoro-phenyl)-methanone (Example 57)

[4-Amino-2-(4-[1,4']bipiperidinyl-1'-yl-phenylamino)-thiazol-5-yl]-(4-chloro-phenyl)-methanone (Example 58)

[4-Amino-2-(4-[1,4']bipiperidinyl-1'-yl-phenylamino)-thiazol-5-yl]-(3,4-difluoro-phenyl)-methanone (Example 59)

[4-Amino-2-(4-[1,4']bipiperidinyl-1'-yl-phenylamino)-thiazol-5-yl]-(3,4-dichloro-phenyl)-methaonone (Example 60) [4-Amino-2-(4-[1,4']bipiperidinyl-1'-yl-phenylamino)-thiazol-5-yl]-(4-fluoro-phenyl)-methanone (Example 61) and

[4-Amino-2-(4-[1,4']bipiperidinyl-1'-yl-phenylamino)-thiazol-5-yl]-(4-chloro-3-nitro-phenyl)-methanone (Example 62).

18. The compound of claim 1, selected from the group consisting of:

4-[4-Amino-2-(4-[1,4']bipiperidinyl-1'-yl-phenylamino)-thiazole-5-carbonyl]-benzoic acid (Example 63)

3-[4-Amino-2-(4-[1,4']bipiperidinyl-1'-yl-phenylamino)-thiazole-5-carbonyl]-benzonitrile (Example 64)

[4-Amino-2-(4-[1,4']bipiperidinyl-1'-yl-phenylamino)-thiazol-5-yl]-(3-hydroxy-phenyl)-methanone (Example 65)

{4-Amino-2-[4-(4-pyrrolidin-1-yl-piperidin-1-yl)-phenylamino]-thiazol-5-yl}-(3,5-difluoro-phenyl)-methanone (Example 66)

{4-Amino-2-[4-(4-pyrrolidin-1-yl-piperidin-1-yl)-phenylamino]-thiazol-5-yl}-(4-chloro-phenyl-methanone (Example 67)

{4-Amino-2-[4-(4-pyrrolidin-1-yl-piperidin-1-yl)-phenylamino]-thiazol-5-yl}-(3,4-difluoro-phenyl)-methanone (Example 68)

{4-Amino-2-[4-(4-pyrrolidin-1-yl-piperidin-1-yl)-phenylamino]-thiazol-5-yl}-(3,4-dichloro-phenyl)-methanone (Example 69)

{4-Amino-2-[4-(4-pyrrolidin-1-yl-piperidin-1-yl)-phenylamino]-thiazol-5-yl}-(4-fluoro-phenyl)-methanone (Example 70)

{4-Amino-2-[4-(4-pyrrolidin-1-yl-piperidin-1-yl)-phenylamino]-thiazol-5-yl}-(4-chloro-3-nitro-phenyl)-methanone (Example 71) and 3-{4-Amino-2-[4-(4-pyrrolidin-1-yl-piperidin-1-yl)-phenylamino]-thiazole-5-carbonyl}-benzonitrile (Example 72).

19. The compound of claim 1, selected from the group consisting of: {4-Amino-2-[4-(3-hydroxy-[1,4']bipiperidinyl-1'-yl)-phenylamino]-thiazol-5-yl}-(3,5-difluoro-phenyl)-methanone (Example 73)

{4-Amino-2-[4-(3-hydroxy-[1,4']bipiperidinyl-1'-yl)-phenylamino]-thiazol-5-yl}-(4-chloro-phenyl)-methanone (Example 74)

{4-Amino-2-[4-(3-hydroxy-[1,4']bipiperidinyl-1'-yl)-phenylamino]-thiazol-5-yl}-(3,5-difluoro-phenyl)-methanone (Example 75)

{4-Amino-2-[4-(3-hydroxy-[1,4']bipiperidinyl-1'-yl)-phenylamino]-thiazol-5-yl}-(3,4-difluoro-phenyl)-methanone (Example 76)

{4-Amino-2-[4-(3-hydroxy-[1,4']bipiperidinyl-1'-yl)-phenylamino]-thiazol-5-yl}-(4-fluoro-phenyl)-methanone (Example 77)

{4-Amino-2-[4-(3-hydroxy-[1,4']bipiperidinyl-1'-yl)-phenylamino]-thiazol-5-yl}-(4-chloro-3-nitro-phenyl)-methanone (Example 78)

4-{4-Amino-2-[4-(3-hydroxy-[1,4']bipiperidinyl-1'-yl)-phenylamino]-thiazole-5-carbonyl}-benzoic acid (Example 79)

3-{4-Amino-2-[4-(3-hydroxy-[1,4']bipiperidinyl-1'-yl)-phenylamino]-thiazole-5-carbonyl}-benzonitrile (Example 80)

{4-Amino-2-[4-(3-hydroxy-[1,4']bipiperidinyl-1'-yl)-phenylamino]-thiazol-5-yl}-(3-hydroxy-phenyl)-methanone (Example 81) and {4-Amino-2-[4-(4-dimethylamino-piperidin-1-yl)-phenylamino]-thiazol-5-yl}-(3,5-difluoro -phenyl)-methanone(Example 82).

20. The compound of claim 1, selected from the group consisting of:

{4-Amino-2-[4-(4-dimethylamino-piperidin-1-yl)-phenylamino]-thiazol-5-yl}-(4-chloro-phenyl)-methanone (Example 83)

{4-Amino-2-[4-(4-dimethylamino-piperidin-1-yl)-phenylamino]-thiazol-5-yl}-(3,4-difluoro-phenyl)-methanone (Example 84)

{4-Amino-2-[4-(4-dimethylamino-piperidin-1-yl)-phenylamino]-thiazol-5-yl}-(3,4-difluoro-phenyl)-methanone (Example 85)

{4-Amino-2-[4-(4-dimethylamino-piperidin-1-yl)-phenylamino]-thiazol-5-yl}-(4-fluoro-phenyl)-methanone (Example 86)

{4-Amino-2-[4-(4-dimethylamino-piperidin-1-yl)-phenylamino]-thiazol-5-yl}-(4-chloro-3-nitro-phenyl)-methanone (Example 87)

3-{4-Amino-2-[4-(4-dimethylamino-piperidin-1-yl)-phenylamino]-thiazole-5-carbonyl}-benzonitrile (Example 88)

[4-Amino-2-(4-[1,4']bipiperidinyl-1'-yl-phenylamino)-thiazol-5-yl]-(3-nitro-phenyl)-methanone (Example 89)

{4-Amino-2-[4-(4-pyrrolidin-1-yl-piperidin-1-yl)-phenylamino]-thiazol-5-yl}-(3-nitro-phenyl)-methanone (Example 90)

{4-Amino-2-[4-(3-hydroxy-[1,4']bipiperidinyl-1'-yl)-phenylamino]-thiazol-5-yl}-(3-nitro-phenyl)-methanone (Example 91) and {4-Amino-2-[4-(4-dimethylamino-piperidin-1-yl)-phenylamino]-thiazol-5-yl}-(3-nitro-phenyl)-methanone (Example 92).

21. The compound of claim 1, selected from the group consisting of:

{-4-Amino-2-[4-(4-dimethylamino-piperidin-1-yl)-phenylamino]-thiazole-5-carbonyl}-2-hydroxy-benzamide (Example 93)

5-{4-Amino-2-[4-(4-pyrrolidin-1-yl-piperidin-1-yl)-phenylamino]-thiazole-5-carbonyl}-2-hydroxy-benzamide (Example 94)

{4-Amino-2-[4-(4-pyrrolidin-1-yl-piperidin-1-yl)-phenylamino]-thiazol-5-yl}-(3-hydroxy-phenyl)-methanone (Example 96)

{4-Amino-2-[4-(4-pyrrolidin-1-yl-piperidin-1-yl)-phenylamino]-thiazol-5-yl}-(3-hydroxy-phenyl)-methanone (Example 97)

{4-Amino-2-[4-(4-morpholin-4-yl-piperidin-1-yl)-phenylamino]-thiazol-5-yl}-(2,3-dihydro-benzo[1,4]dioxin-6yl)-methanone (Example 98)

{4-Amino-2-[4-(4-morpholin-4-yl-piperidin-1-yl)-phenylamino]-thiazol-5-yl}-(3-fluoro-phenyl)-methanone (Example 99)

{4-Amino-2-[4-(4-morpholin-4-yl-piperidin-1-yl)-phenylamino]-thiazol-5-yl}-(3-fluoro-4-methoxy-phenyl-methanone (Example 100)

{4-Amino-2-[4-(4-morpholin-4-yl-piperidin-1-yl)-phenylamino]-thiazol-5-yl}-benzo[1,3]dioxol-5yl-methanone (Example 101)

{4-Amino-2-[4-(4-morpholin-4-yl-piperidin-1-yl)-phenylamino]-thiazol-5-yl}-(3-methoxy-pheny)-methanone (Example 102) and {4-Amino-2-[4-(4-morpholin-4-yl-piperidin-1-yl)-phenylamino]-thiazol-5-yl}-(3-hydroxy-phenyl)-methanone (Example 103).

22. The compound of claim 1, selected from the group consisting of:

3-{4-Amino-2-[4-(4-morpholin-4-yl-piperidin-1-yl)-phenylamino]-thiazole-5-carbonyl}-benzonitrile (Example 104)

{4-Amino-2-[4-(4-morpholin-4-yl-piperidin-1-yl)-phenylamino]-thiazol-5-yl}-(3-nitro-phenyl)-methanone (Example 105)

{4-Amino-2-[4-(4-morpholin-4-yl-piperidin-1-yl)-phenylamino]-thiazol-5-yl}-(4-methoxy-3-nitro-phenyl)-methanone (Example 106)

{4-Amino-2-[4-(4-pyrrolidin-1-yl-piperidin-1-yl)-phenylamino]-thiazol-5-yl}-(4-methoxy-3-nitro-phenyl)-methanone (Example 107)

[4-Amino-2-(4-[1,4']bipiperidinyl-1'-yl-phenylamino)-thiazol-5-yl]-(4-methoxy-3-nitro-phenyl)-methanone (Example 108)

{4-Amino-2-[4-(4-pyrrolidin-1-yl-piperidin-1-yl)-phenylamino]-thiazol-5-yl}-tolyl-methanone (Example 109)

{4-Amino-2-[4-(4-dimethylamino-piperidin-1-yl)-phenylamino]-thiazol-5-yl}-tolyl-methanone (Example 110)

[4-Amino-2-(4-[1,4']bipiperidinyl-1'-yl-phenylamino)-thiazol-5-yl]-tolyl-methanone (Example 111)

{4-Amino-2-[4-(4-morpholin-4-yl-piperidin-1-yl)-phenylamino]-thiazol-5-yl}-tolyl-methanone, compound with hydrobromide (Example 112) and {4-Amino-2-[4-(4-dimethylamino-piperidin-1-yl)-phenylamino]-thiazol-5-yl}-(4-methoxy-3-nitro-phenyl-methanone (Example 113).

23. The compound of claim 1, selected from the group consisting of:
- {4-Amino-2-[4-(4-pyrrolidin-1-yl-piperidin-1-yl)-phenylamino]-thiazol-5-yl}-(3-ethyl-phenyl)-methanone (Example 114)
- {4-Amino-2-[4-(4-dimethylamino-piperidin-1-yl)-phenylamino]-thiazol-5-yl}-(3-ethyl-phenyl)-methanone (Example 115)
- {4-Amino-2-[4-(4-morpholin-4-yl-piperidin-1-yl)-phenylamino]-thiazol-5-yl}-(3-ethyl-phenyl)-methanone (Example 116)
- [4-Amino-2-(4-[1,4']bipiperidinyl-1'-yl-phenylamino)-thiazol-5-yl]-(3-ethyl-phenyl)-methanone (Example 117)
- {4-Amino-2-[4-(4-pyrrolidin-1-yl-piperidin-1-yl)-phenylamino]-thiazol-5-yl}-(3-ethyl-phenyl)-methanone (Example 118)
- {4-Amino-2-[4-(4-pyrrolidin-1-yl-piperidin-1-yl)-phenylamino]-thiazol-5-yl}-(3-cyclopropyl-phenyl)-methanone (Example 119)
- {4-Amino-2-[4-(4-dimethylamino-piperidin-1-yl)-phenylamino]-thiazol-5-yl}-(3-cyclopropy-phenyl)-methanone (Example 120)
- {4-Amino-2-[4-(4-pyrrolidin-1-yl-piperidin-1-yl)-phenylamino]-thiazol-5-yl}-(3-fluoro-4-methyl-phenyl)-methanone (Example 121)
- {4-Amino-2-[4-(4-pyrrolidin-1-yl-piperidin-1-yl)-phenylamino]-thiazol-5-yl}-(3-ethyl-4-fluoro-phenyl)-methanone (Example 122) and
- {4-Amino-2-[4-(4-pyrrolidin-1-yl-piperidin-1-yl)-phenylamino]-thiazol-5-yl}-(4-hydroxy-3-propyl-phenyl)-methanone (Example 123).

24. The compound of claim 1, selected from the group consisting of:
- 6-(4-Amino-2-{4-[ethyl-(3-pyrrolidin-1-yl-propyl)-amino]-phenylamino}-thiazole-5-carbonyl)-1-H-indole-2-carboxylic acid ethyl ester (Example 124)
- {4-Amino-2-[4-(3-ethylamino-pyrrolidin-1-yl)-phenylamino]-thiazol-5-yl}-(3-fluoro-phenyl)-methanone (Example 132)
- {4-Amino-2-[4-(3-ethylamino-pyrrolidin-1-yl)-phenylamino]-thiazol-5-yl}-(3-fluoro-4-methoxy-phenyl)-methanone (Example 133)
- {4-Amino-2-[4-(3-ethylamino-pyrrolidin-1-yl)-phenylamino]-thiazol-5-yl}-(3-methoxy-phenyl)-methanone (Example 134)
- {4-Amino-2-[4-(4-ethylamino-piperidin-1-yl)-phenylamino]-thiazol-5-yl}-(3-methoxy-phenyl)-methanone (Example 135)
- {4-Amino-2-[4-(4-ethylamino-piperidin-1-yl)-phenylamino]-thiazol-5-yl}-(3-fluoro-4-methoxy-phenyl)-methanone (Example 136) and
- {4-Amino-2-[4-(4-ethylamino-piperidin-1-yl)-phenylamino]-thiazol-5-yl}-(3-fluoro-phenyl)-methanone (Example 137).

25. The compound of claim 1, selected from the group consisting of:
- {2-Amino-5-[4-(4-pyrrolidin-1-yl-piperidin-1-yl)-phenylamino]-4H-pyrrol-3-yl}-(3-fluoro-4-methoxy-phenyl)-methanone (Example 23)
- {4-Amino-2-[4-(4-pyrrolidin-1-yl-piperidin-1-yl)-phenylamino]-thiazol-5-yl}-(2,3-dihydro-benzo[1,4]dioxin-6-yl)-methanone (Example 26)
- [4-Amino-2-(4-[1,4']bipiperidinyl-1'-yl-phenylamino)-thiazol-5-yl]-(3-fluoro-phenyl)-methanone (Example 30)
- [4-Amino-2-(4-[1,4']bipiperidinyl-1'-yl-phenylamino)-thiazol-5-yl]-(2,3-dihydro-benzo[1,4]dioxin-6-yl)-methanone (Example 33)
- [4-Amino-2-(4-[1,4']bipiperidinyl-1'-yl-phenylamino)-thiazol-5-yl]-(3-methoxy-phenyl)-methanone (Example 34)
- {4-Amino-2-[4-(3-hydroxy-[1,4']bipiperidinyl-1'-yl)-phenylamino]-thiazol-5-yl}-(3-fluoro-4-methoxy-phenyl)-methanone (Example 36)
- {4-Amino-2-[4-(4-dimethylamino-piperidin-1-yl)-phenylamino]-thiazol-5-yl}-benzo[1,3]dioxol-5-yl-methanone (Example 43)
- {4-Amino-2-[4-(4-dimethylamino-piperidin-1-yl)-phenylamino]-thiazol-5-yl}-(3-methoxy-phenyl)-methanone (Example 45)
- {4-Amino-2-[4-(4-dimethylamino-piperidin-1-yl)-phenylamino]-thiazol-5-yl}-(3-hydroxy-phenyl)-methanone (Example 50)
- {4-Amino-2-[4-(4-pyrrolidin-1-yl-piperidin-1-yl)-phenylamino]-thiazol-5-yl}-(3-nitro-phenyl)-methanone (Example 90)
- {4-Amino-2-[4-(3-hydroxy-[1,4']bipiperidinyl-1'-yl)-phenylamino]-thiazol-5-yl}-3-nitro-phenyl)-methanone (Example 91)
- [4-Amino-2-(4-[1,4']bipiperidinyl-1'-yl-phenylamino)-thiazol-5-yl]-(3-ethyl-phenyl)-methanone (Example 117) and
- {4-Amino-2-[4-(3-ethylamino-pyrrolidin-1-yl)-phenylamino]-thiazol-5-yl}-(3-fluoro-phenyl)-methanone (Example 132).

26. A pharmaceutical composition comprising as an active ingredient an effective amount of a compound of claim 1 or a pharmaceutically acceptable salt or ester thereof, and a pharmaceutically acceptable carrier or excipient.

27. The pharmaceutical composition of claim 26, which is suitable for parenteral administration.

* * * * *

UNITED STATES PATENT AND TRADEMARK OFFICE
CERTIFICATE OF CORRECTION

| | |
|---|---|
| PATENT NO. | : 7,211,576 B2 |
| APPLICATION NO. | : 11/098563 |
| DATED | : May 1, 2007 |
| INVENTOR(S) | : Ding et al. |

Page 1 of 1

It is certified that error appears in the above-identified patent and that said Letters Patent is hereby corrected as shown below:

IN THE CLAIMS:

• Claim 1, Column 151, lines 41-55, formula (I) reads:

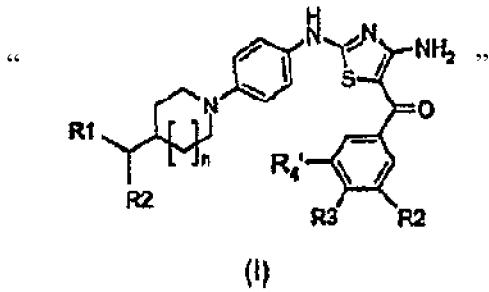

Formula (I) should read:

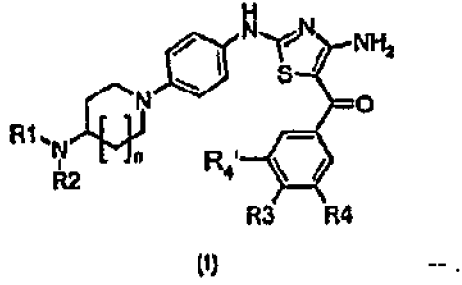

• Claim 21, Column 156, line 6: "{-4-Amino-2-[4-(4-dimethylamino-piperidin-1-yl)-" should read -- 5-{4-Amino-2-[4-(4-dimethylamino-piperidin-1-yl) -- .

Signed and Sealed this

Twenty-eighth Day of August, 2007

JON W. DUDAS
*Director of the United States Patent and Trademark Office*